United States Patent
Cha et al.

(10) Patent No.: US 12,284,914 B2
(45) Date of Patent: Apr. 22, 2025

(54) ORGANIC LIGHT-EMITTING COMPOUND AND ORGANIC LIGHT-EMITTING DIODE COMPRISING SAME

(71) Applicant: SFC CO., LTD., Cheongju-si (KR)

(72) Inventors: Soon-Wook Cha, Goyang-si (KR); Yoona Shin, Seoul (KR); Jea-Geon Lim, Cheongju-si (KR); Sang-Woo Park, Seoul (KR); Ji-Hwan Kim, Anyang-si (KR); Jung-Ho Yoo, Seosan-si (KR); Young-Hwan Park, Cheongju-si (KR)

(73) Assignee: SFC CO., LTD., Cheongju-si (KR)

( * ) Notice: Subject to any disclaimer, the term of this patent is extended or adjusted under 35 U.S.C. 154(b) by 660 days.

(21) Appl. No.: 15/771,418

(22) PCT Filed: Oct. 26, 2016

(86) PCT No.: PCT/KR2016/012063
§ 371 (c)(1),
(2) Date: Apr. 27, 2018

(87) PCT Pub. No.: WO2017/082556
PCT Pub. Date: May 18, 2017

(65) Prior Publication Data
US 2018/0351112 A1    Dec. 6, 2018

(30) Foreign Application Priority Data
Nov. 12, 2015    (KR) .................. 10-2015-0158893

(51) Int. Cl.
*H10K 85/60*    (2023.01)
*C07B 59/00*    (2006.01)
(Continued)

(52) U.S. Cl.
CPC ....... *H10K 85/6574* (2023.02); *C07B 59/002* (2013.01); *C07D 209/82* (2013.01);
(Continued)

(58) Field of Classification Search
CPC .... H01L 51/5012–5044; C07D 493/10; H10K 85/6574
See application file for complete search history.

(56) References Cited

U.S. PATENT DOCUMENTS 10,693,084 B2 *   6/2020   Park ................... H01L 51/0071
10,741,768 B2 *   8/2020   Lee .................... H01L 51/0054
(Continued)

FOREIGN PATENT DOCUMENTS

KR    1020060113954 A    11/2006
KR      101092006 B1    12/2011
(Continued)

OTHER PUBLICATIONS

Machine Translation of KR 20130077470 A. (Year: 2020).*
(Continued)

*Primary Examiner* — Sean M DeGuire
(74) *Attorney, Agent, or Firm* — STIP Law Group, LLC

(57) ABSTRACT

Disclosed herein are a compound represented by Chemical Formula A or Chemical Formula B and an organic light-emitting diode comprising the same.

11 Claims, 1 Drawing Sheet

(51) Int. Cl.
  *C07D 209/82* (2006.01)
  *C07D 307/91* (2006.01)
  *C07D 307/94* (2006.01)
  *C07D 333/78* (2006.01)
  *C07D 405/14* (2006.01)
  *C07D 407/04* (2006.01)
  *C07D 407/14* (2006.01)
  *C07D 409/04* (2006.01)
  *C07D 409/14* (2006.01)
  *C07D 491/048* (2006.01)
  *C07D 493/10* (2006.01)
  *C07D 495/04* (2006.01)
  *C07D 495/10* (2006.01)
  *C07D 519/00* (2006.01)
  *C09K 11/06* (2006.01)
  *H10K 50/11* (2023.01)
  *H10K 50/15* (2023.01)
  *H10K 50/16* (2023.01)
  *H10K 50/17* (2023.01)

(52) U.S. Cl.
  CPC ......... *C07D 307/91* (2013.01); *C07D 307/94* (2013.01); *C07D 333/78* (2013.01); *C07D 405/14* (2013.01); *C07D 407/04* (2013.01); *C07D 407/14* (2013.01); *C07D 409/04* (2013.01); *C07D 409/14* (2013.01); *C07D 491/048* (2013.01); *C07D 493/10* (2013.01); *C07D 495/04* (2013.01); *C07D 495/10* (2013.01); *C07D 519/00* (2013.01); *C09K 11/06* (2013.01); *H10K 85/6572* (2023.02); *C09K 2211/1018* (2013.01); *H10K 50/11* (2023.02); *H10K 50/15* (2023.02); *H10K 50/16* (2023.02); *H10K 50/17* (2023.02); *H10K 50/171* (2023.02); *H10K 85/622* (2023.02); *H10K 85/633* (2023.02); *Y02B 20/00* (2013.01)

(56) References Cited

U.S. PATENT DOCUMENTS

| | | | | |
|---|---|---|---|---|
| 10,790,450 | B2* | 9/2020 | Pyo | C07D 493/10 |
| 10,797,259 | B2* | 10/2020 | Cha | C07D 307/91 |
| 2002/0132134 | A1* | 9/2002 | Hu | H01L 51/0052 |
| | | | | 428/690 |
| 2007/0015005 | A1* | 1/2007 | Chen | C07F 5/027 |
| | | | | 428/690 |
| 2016/0093813 | A1* | 3/2016 | Stoessel | H10K 85/6572 |
| | | | | 438/46 |
| 2016/0308147 | A1* | 10/2016 | Parham | C07D 405/04 |
| 2016/0351816 | A1* | 12/2016 | Kim | C09K 11/02 |
| 2016/0351817 | A1* | 12/2016 | Kim | H01L 51/006 |
| 2016/0351818 | A1* | 12/2016 | Kim | H01L 51/0052 |
| 2018/0141957 | A1* | 5/2018 | Park | C07D 491/048 |
| 2020/0127209 | A1* | 4/2020 | Cha | H01L 51/00 |

FOREIGN PATENT DOCUMENTS

| | | | | |
|---|---|---|---|---|
| KR | 1020130077470 A | 7/2013 | | |
| KR | 101429035 B1 | 8/2014 | | |
| KR | 1020150009370 A | 1/2015 | | |
| KR | 1020150034390 A | 4/2015 | | |
| KR | 1020150045809 A | 4/2015 | | |
| KR | 1020150113642 A | 10/2015 | | |
| KR | 1020150130206 A | 11/2015 | | |
| KR | 1020160126873 A | 11/2016 | | |
| WO | WO-2014185751 A1 * | 11/2014 | ............... | C07F 5/02 |
| WO | WO2015022051 A1 | 2/2015 | | |
| WO | WO2015090504 A2 | 6/2015 | | |

OTHER PUBLICATIONS

Jeon, et al. "Fluorenobenzofuran as the core structure of high triplet energy host materials for green phosphorescent organic light-emitting diodes." Journal of Materials Chemistry 22.21 (2012): 10537-10541.*
International Search Report of PCT/KR2016/012063, Jan. 26, 2017, English Translation.
Office Action from Korean Intellectual Property Office, May 16, 2017.
Office Action from Korean Intellectual Property Office, Sep. 15, 2017.

* cited by examiner

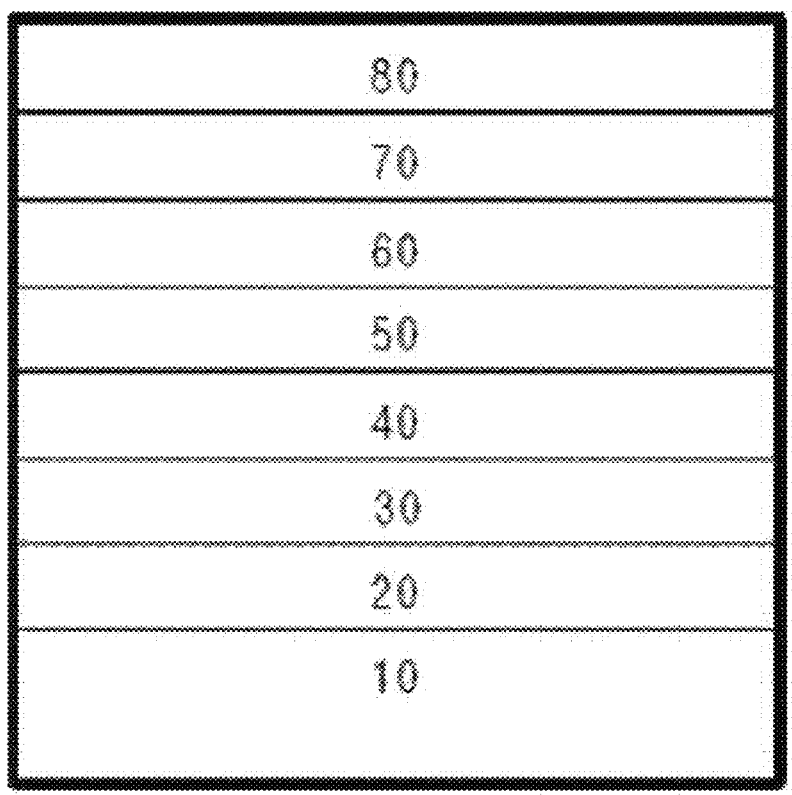

ORGANIC LIGHT-EMITTING COMPOUND AND ORGANIC LIGHT-EMITTING DIODE COMPRISING SAME

CROSS-REFERENCE TO RELATED APPLICATIONS

This application is the U.S. National Phase under 35 U.S.C. § 371 of International Application No. PCT/KR2016/012063 filed on Oct. 26, 2016, which in turn claims the benefit of Korean Application No. 10-2015-0158893, filed on Nov. 12, 2015, the disclosures of which are incorporated by reference into the present application.

TECHNICAL FIELD

The present disclosure relates to a novel compound for organic light-emitting diodes and an organic light-emitting diode comprising the same and, more particularly, to a compound for organic light-emitting diodes, which shows excellent diode characteristics including low-voltage operation and luminance efficiency when used as a fluorescent host, and an organic light-emitting diode comprising the same.

BACKGROUND ART

Organic light-emitting diodes (OLEDs), based on self-luminescence, enjoy the advantage of having a wide viewing angle and being able to be made thinner and lighter than liquid crystal displays (LCDs). In addition, an OLED display exhibits a very fast response time. Accordingly, OLEDs find applications in the full color display field or the illumination field.

In general, the term "organic light-emitting phenomenon" refers to a phenomenon in which electrical energy is converted to light energy by means of an organic material. An OLED using the organic light phenomenon has a structure usually comprising an anode, a cathode, and an organic material layer interposed therebetween. In this regard, the organic material layer may be, for the most part, of a multilayer structure consisting of different materials, for example, a hole injecting layer, a hole transport layer, a light-emitting layer, an electron transport layer, and an electron injecting layer, in order to improve the efficiency and stability of the organic light-emitting diode. In the organic light-emitting diode having such a structure, when a voltage is applied between the two electrodes, a hole injected from the anode migrates to the organic layer while an electron is released from the cathode and moves toward the organic layer. In the luminescent zone, the hole and the electron recombine to produce an exciton. When the exciton returns to the ground state from the excited state, the molecule of the organic layer emits light. Such an organic light-emitting diode is known to have characteristics such as self-luminescence, high luminance, high efficiency, low driving voltage, a wide viewing angle, high contrast, and high-speed response.

Materials used as organic layers in OLEDs may be divided into luminescent materials and charge transport materials, for example, a hole injection material, a hole transport material, an electron injection material, and an electron transport material. As for the luminescent materials, there are two main families of OLED: those based on small molecules and those employing polymers. The light-emitting mechanism forms the basis for classification of the luminescent materials as fluorescent or phosphorescent materials, which use excitons in singlet and triplet states, respectively.

Meanwhile, when a single material is employed as the luminescent material, intermolecular actions cause the wavelength of maximum luminescence to shift toward a longer wavelength, decreasing color purity or attenuating light with the consequent reduction in efficiency of the diode. In this regard, a host-dopant system may be used as a luminescent material so as to increase the color purity and the light emission efficiency through energy transfer.

This is based on the principle whereby, when a dopant is smaller in energy band gap than a host accounting for the light-emitting layer, the addition of a small amount of the dopant to the host generates excitons from the light-emitting layer so that the excitons are transported to the dopant, emitting light at high efficiency. Here, light of desired wavelengths can be obtained depending on the kinds of dopant because the wavelength of the host moves to the wavelength range of the dopant.

With regard to related arts pertaining to host compounds in the light-emitting layer, reference may be made to Korean Patent No. 10-1092006 (Dec. 9, 2011), which discloses an OLED comprising a luminescent medium layer containing a compound in which an anthracene structure has substituted phenyl groups attached respectively to opposite ends thereof, and Korean Patent No. 10-2006-0113954 A (Nov. 3, 2006), which describes on OLED comprising a luminescent medium layer containing an asymmetric anthracene derivative of a certain structure.

In spite of various kinds of compounds prepared for use in luminescent media layers inclusive of the related art, there is still the continued need to develop organic layer materials that enable low-voltage operation and are stable and of high efficiency.

DETAILED DESCRIPTION OF THE INVENTION

Technical Problem

Accordingly, a first purpose of the present disclosure is to provide a compound for organic light-emitting diodes, which can be used in a light-emitting layer of an organic light-emitting diode and shows excellent diode characteristics including low-voltage operation and luminance efficiency.

A second purpose of the present disclosure is to provide an organic light-emitting diode comprising the compound.

Technical Solution

In order to achieve the first purpose, the present disclosure provides an organic light-emitting compound represented by the following [Chemical Formula A] or [Chemical Formula B]:

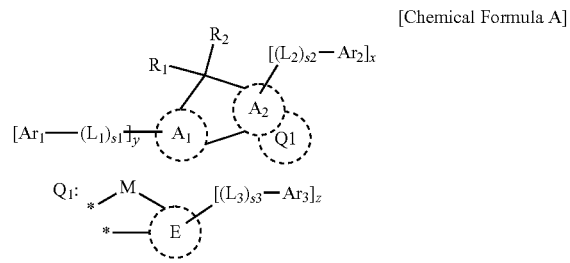

[Chemical Formula A]

-continued

[Chemical Formula B]

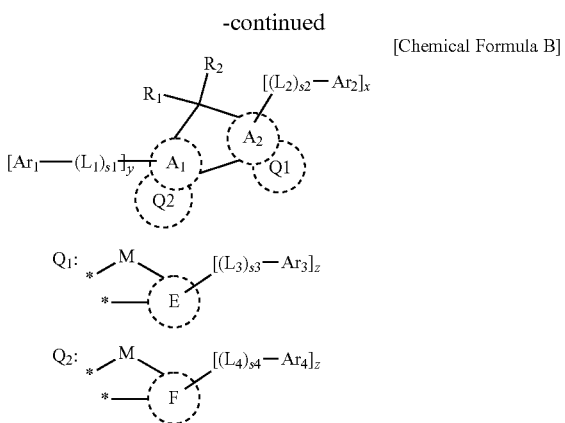

wherein,
$A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms, wherein two adjacent carbon atoms of the aromatic ring $A_1$ and two adjacent carbon atoms of the aromatic ring $A_2$ form a 5-membered fused ring together with the carbon atom having substituents $R_1$ and $R_2$ linked thereto;

linkers $L_1$ to $L_4$ may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$R_1$ to $R_9$, and $Ar_1$ to $Ar_4$ may be the same or different, and are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 1 to 30 carbon atoms, a cyano, a nitro, and a halogen, with the proviso that $R_1$ and $R_2$ may be bonded to each other to form a mono- or polycyclic aliphatic or aromatic ring, which may be a heterocyclic ring bearing a heteroatom selected from among N, O, P, Si, S, Ge, Se, and Te as a ring member;

s1 to s4 are each independently an integer of 1 to 3, with the proviso that when any of them is 2 or greater, the corresponding linkers $L_1$ to $L_4$ may be the same or different, x is an integer of 1 or 2, and y and z may be the same or different and are each independently an integer of 0 to 3; and two adjacent carbon atoms of the $A_2$ ring moiety of Chemical Formula A may occupy respective positions * of Structural Formula $Q_1$ to form a fused ring, and two adjacent carbon atoms of the $A_1$ ring moiety of Chemical Formula B may occupy respective positions * of structural Formula $Q_2$ to form a fused ring, and two adjacent carbon atoms of the $A_2$ ring moiety of Chemical Formula B may occupy respective positions * of Structural Formula $Q_1$ to form a fused ring, wherein the term 'substituted' in the expression 'substituted or unsubstituted' used in Chemical Formulas A and B means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

In order to accomplish the second purpose, the present disclosure provides an organic light-emitting diode, comprising a first electrode; a second electrode facing the first electrode; and an organic layer interposed therebetween, wherein the organic layer contains at least one of the compounds of the present disclosure.

Advantageous Effects

Allowing an organic light-emitting diode to be drive at a low voltage and exhibit high luminance efficiency, the organic light-emitting compound represented by Chemical Formula A can be utilized in fabricating a stable and excellent diode.

BRIEF DESCRIPTION OF THE DRAWINGS

FIG. 1 is a diagram of the structure of an organic light-emitting diode according to some embodiments of the present disclosure

MODE FOR CARRYING OUT THE INVENTION

Hereinafter, some embodiments which can be easily performed by those skilled in the art will be described with reference to the accompanying drawings. In the drawings of the disclosure, sizes and dimensions of structures are illustrated by enlarging or reducing as compared with the actual sizes and dimensions to clarify the disclosure, the known configurations are not illustrated to exhibit characteristic configurations, and the disclosure is not limited to the drawings.

When describing the principle of the embodiments of the present disclosure in detail, details of well-known functions and features may be omitted to avoid unnecessarily obscuring the presented embodiments.

In addition, the size and thickness of each configuration illustrated in the drawings are arbitrarily illustrated for the sake of convenience of explanation, and thus the present disclosure may not be necessarily limited to the illustration. Further, in the drawings, the thickness of layers and regions are illustrated in enlargement for clarity. For the sake of explanation, thicknesses of certain layers and regions are exaggerated.

Throughout the specification, when a portion may "include" a certain constituent element, unless explicitly described to the contrary, it may not be construed to exclude another constituent element but may be construed to further include other constituent elements. Further, throughout the specification, the word "on" means positioning on or below the object portion, but does not essentially mean positioning on the lower side of the object portion based on a gravity direction.

The present disclosure provides as a novel aromatic organic light-emitting compound a compound represented by the following Chemical Formula A or Chemical Formula B:

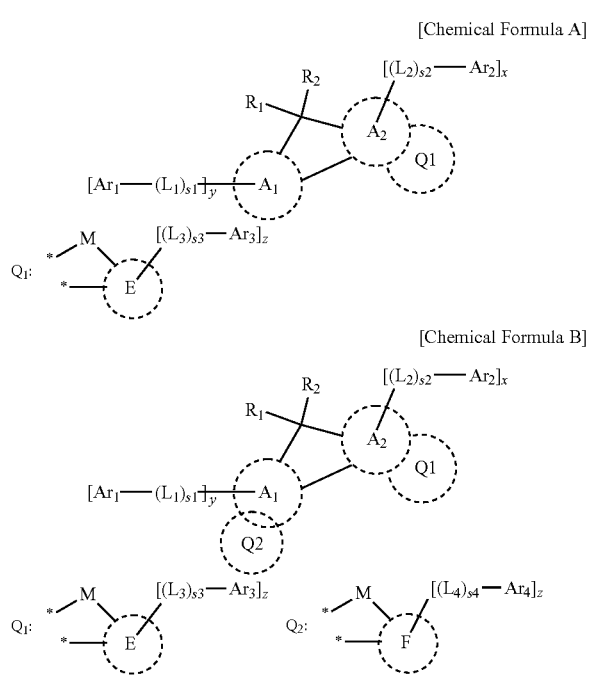

[Chemical Formula A]

[Chemical Formula B]

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms, wherein two adjacent carbon atoms of the aromatic ring $A_1$ and two adjacent carbon atoms of the aromatic ring $A_2$ form a 5-membered fused ring together with the carbon atom having substituents $R_1$ and $R_2$ linked thereto;

linkers $L_1$ to $L_4$ may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$R_1$ to $R_9$, and $Ar_1$ to $Ar_4$ may be the same or different, and are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 1 to 30 carbon atoms, a cyano, a nitro, and a halogen, with the proviso that $R_1$ and $R_2$ may be bonded to each other to form a mono- or polycyclic aliphatic or aromatic ring, which may be a heterocyclic ring bearing a heteroatom selected from among N, O, P, Si, S, Ge, Se, and Te as a ring member;

s1 to s4 are each independently an integer of 1 to 3, with the proviso that when any of them is 2 or greater, the corresponding linkers $L_1$ to $L_4$ may be the same or different, x is an integer of 1 or 2, and y and z may be the same or different and are each independently an integer of 0 to 3; and two adjacent carbon atoms of the $A_2$ ring moiety of Chemical Formula A may occupy respective positions * of Structural Formula $Q_1$ to form a fused ring, and two adjacent carbon atoms of the $A_1$ ring moiety of Chemical Formula B may occupy respective positions * of structural Formula $Q_2$ to form a fused ring, and two adjacent carbon atoms of the $A_2$ ring moiety of Chemical Formula B may occupy respective positions * of Structural Formula $Q_1$ to form a fused ring, wherein the term 'substituted' in the expression 'substituted or unsubstituted' used in Chemical Formulas A and B means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

The expression indicating the number of carbon atoms, such as "a substituted or unsubstituted alkyl of 1 to 24 carbon atoms", "a substituted or unsubstituted aryl of 6 to 24 carbon atoms", etc. means the total number of carbon atoms of, for example, the alkyl or aryl radical or moiety alone, exclusive of the number of carbon atoms of substituents attached thereto. For instance, a phenyl group with a butyl at the para position falls within the scope of an aryl of 6 carbon atoms, even though it is substituted with a butyl radical of 4 carbon atoms.

As used herein, the term "aryl" as a substituent used in the compounds of the present disclosure means an organic radical derived from an aromatic hydrocarbon by removing a hydrogen atom and may further include a fused ring that is formed by adjacent substituents on the organic radical.

Concrete examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, at least one hydrogen atom of which may be substituted by a deuterium atom, a halogen atom, a hydroxy, a nitro, a cyano, a silyl, an amino (—NH$_2$, —NH(R), or —N(R')(R") wherein R' and R" are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, or a heteroarylalkyl of 2 to 24 carbon atoms.

The substituent heteroaryl used in the compound of the present disclosure refers to a cyclic aromatic system of 2 to 24 carbon atoms bearing one to three heteroatoms selected from among N, O, P, and S. In the aromatic system, two or more rings may be fused. One or more hydrogen atoms on the heteroaryl may be substituted with the same substituents as on the aryl.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the substituent alkoxy useful in the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative among examples of the substituent silyl useful in the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atoms of the silyl may be substituted by the same substituent as in the aryl.

The compound represented by Chemical Formula A or B of the present invention has the structural feature that if Structural Formula $Q_1$ is connected to the $A_2$ ring in Chemical Formula A, the linker $L_2$ moiety containing $Ar_2$ must be bonded to the $A_2$ ring and that if Structural Formula $Q_2$ and $Q_1$ are connected respectively to $A_1$ and $A_2$ rings in Chemical Formula B, the linker $L_2$ moiety containing $Ar_2$ must be bonded to the $A_2$ ring.

In Chemical Formula A or B, $A_1$, $A_2$, E, and F may be the same or different and each be independently substituted or unsubstituted aromatic hydrocarbon rings of 6 to 50 carbon atoms.

As stated above, when $A_1$, $A_2$, E, and F in Chemical Formula A or B are each independently substituted or unsubstituted aromatic hydrocarbon rings of 6 to 50 carbon atoms, the substituted or unsubstituted aromatic hydrocarbon rings of 6 to 50 carbon atoms may be the same or different and each be independently selected from among compounds represented by Structural Formulas 10 to 21:

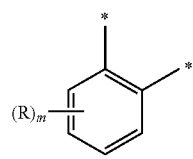

[Structural Formula 10]

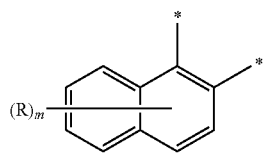

[Structural Formula 11]

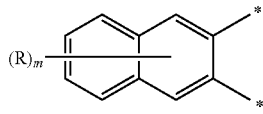

[Structural Formula 12]

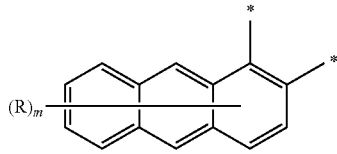

[Structural Formula 13]

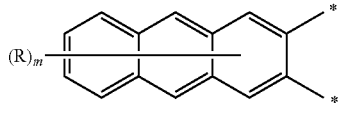

[Structural Formula 14]

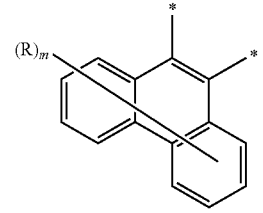

[Structural Formula 15]

-continued

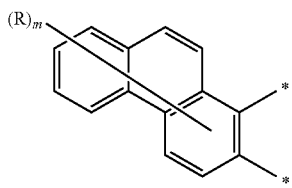
[Structural Formula 16]

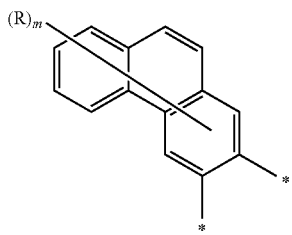
[Structural Formula 17]

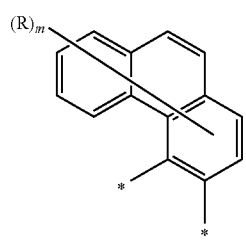
[Structural Formula 18]

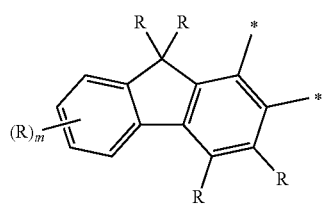
[Structural Formula 19]

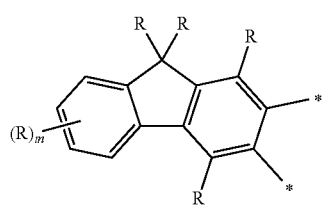
[Structural Formula 20]

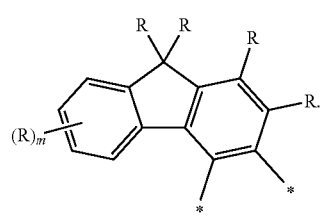
[Structural Formula 21]

wherein
"-*" denotes a bonding site for forming a 5-membered ring bearing the carbon atom connected to the substituents $R_1$ and $R_2$ or a bonding site for forming a 5-membered ring bearing M of Structural Formula $Q_1$ and $Q_2$;
when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring;
R's are the same as defined above for $R_1$ and $R_2$, and m is an integer of 1 to 8, with the proviso that when m is 2 or greater or two or more R's exist, the corresponding R's may be the same or different.

According to one embodiment of the present disclosure, the linkers L1 to L4 in Chemical Formula A or B may be a single bond or one selected from among compounds represented by the following Structural Formulas 1 to 9, and s1 to s4 may each be 1 or 2, and x may be 1:

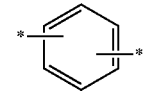
[Structural Formula 1]

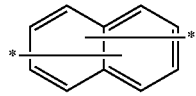
[Structural Formula 2]

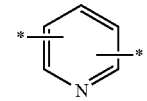
[Structural Formula 3]

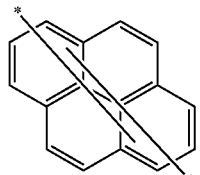
[Structural Formula 4]

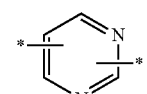
[Structural Formula 5]

[Structural Formula 6]

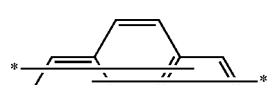
[Structural Formula 7]

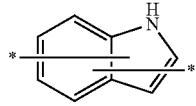
[Structural Formula 8]

In the linkers, each of the unsubstituted carbon atoms of the aromatic ring moiety is bound with a hydrogen atom or a deuterium atom.

In Chemical Formulas A and B according to an embodiment of the present disclosure, $Ar_1$ to $Ar_4$ may each be selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, and a substituted or unsubstituted alkoxy of 1 to 30 carbon atoms, x and y may each be 1, and z may be 0. In a particular embodiment, Ar2 may be a substituted or unsubstituted aryl of 6 to 50 carbon atoms, or a substituted or unsubstituted heteroaryl of 2 to 50 carbon atoms.

In Chemical Formula A or B, $R_1$ and $R_2$ may be the same or different and each be independently a substituted or unsubstituted aryl of 6 to 24 carbon atoms. In this regard, $R_1$ and $R_2$ may be connected to each other to form a ring or may be in a disconnected state without forming a ring.

Concrete examples of the compound represented by Chemical Formula A or B include, but are not limited to, the following compounds represented by Chemical Formulas 1 to 138:

<Chemical Formula 1>

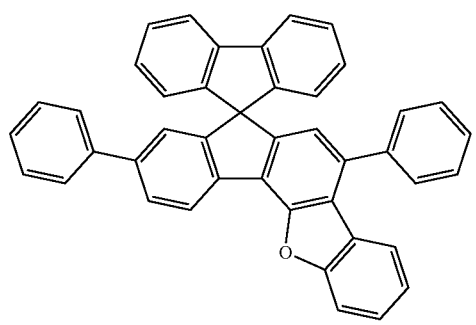

<Chemical Formula 2>

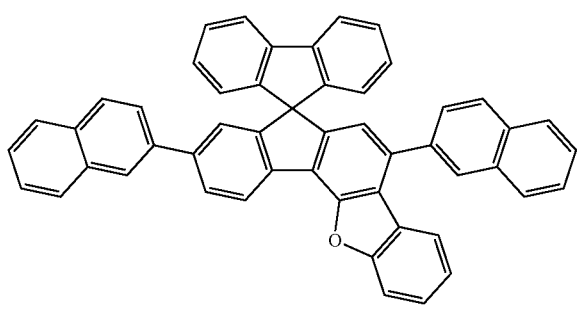

<Chemical Formula 3>

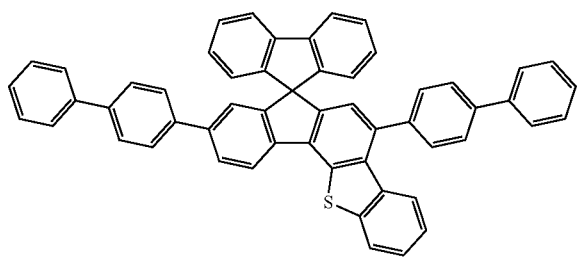

<Chemical Formula 4>

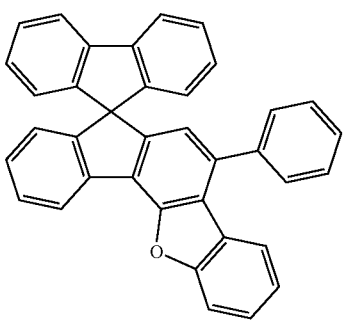

-continued

<Chemical Formula 5>

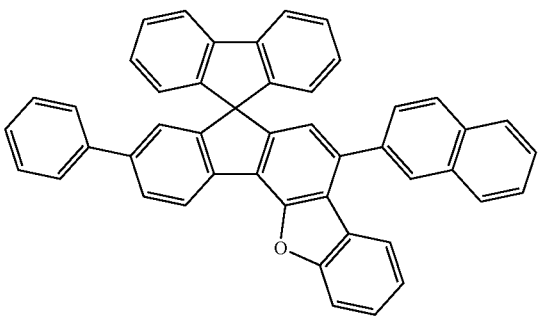

<Chemical Formula 6>

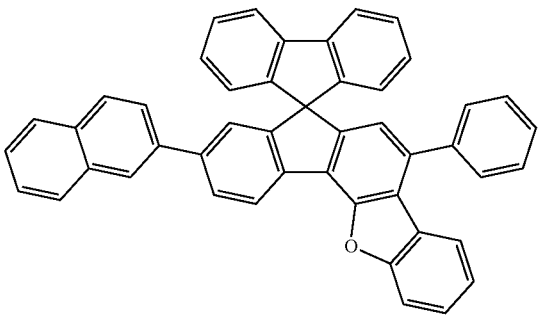

<Chemical Formula 7>

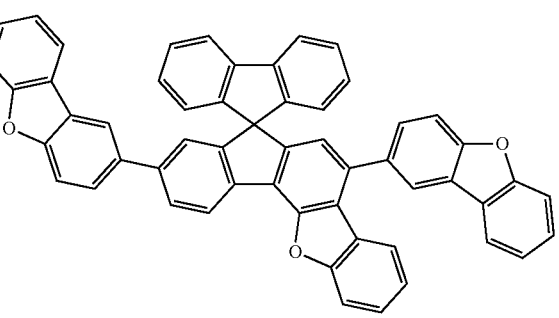

<Chemical Formula 8>

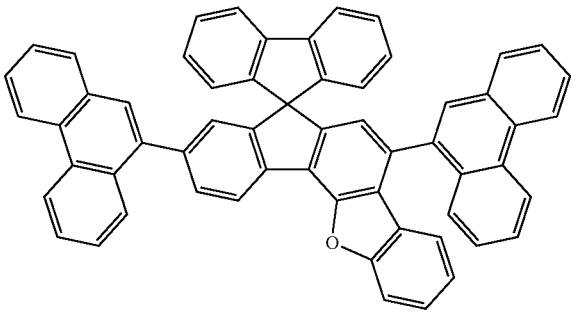

<Chemical Formula 9>
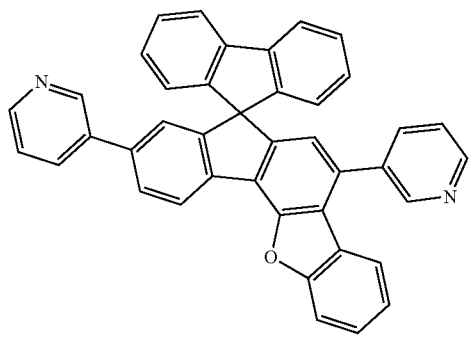
<Chemical Formula 10>
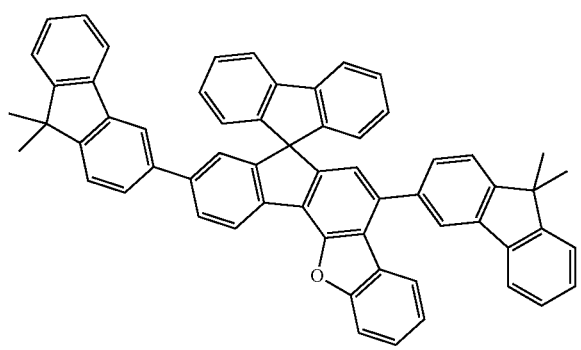
<Chemical Formula 11>
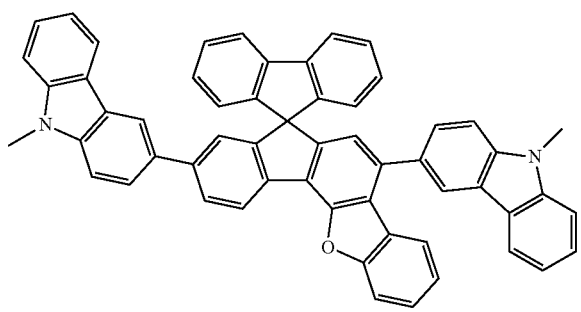
<Chemical Formula 12>
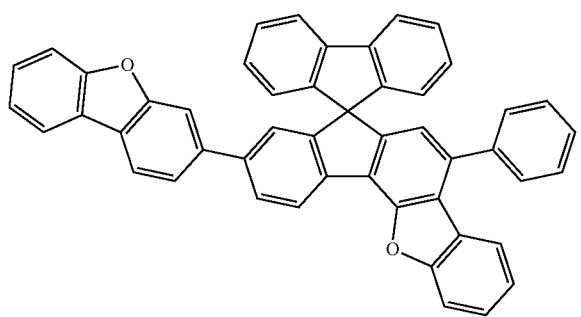
<Chemical Formula 13>
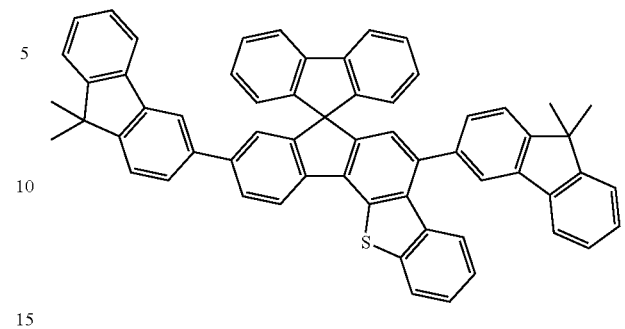
<Chemical Formula 14>
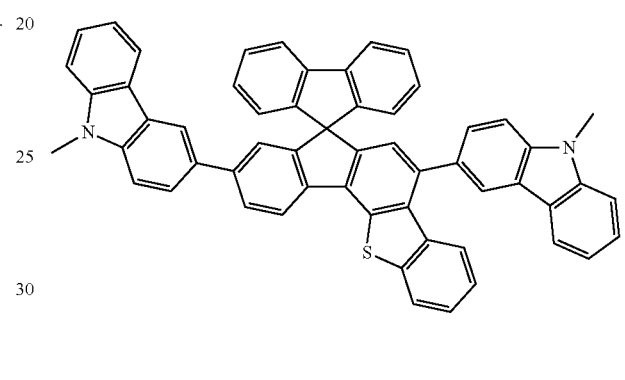
<Chemical Formula 15>
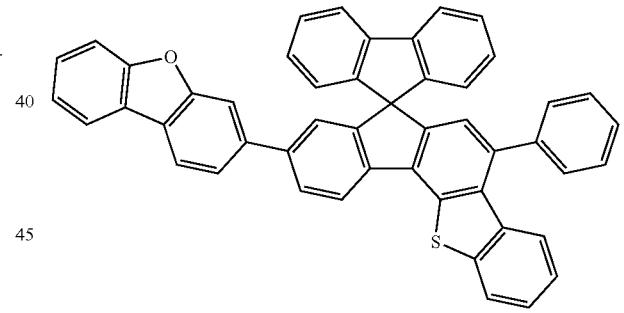
<Chemical Formula 16>
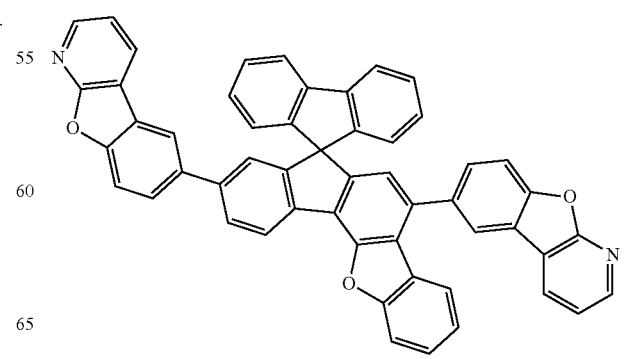

<Chemical Formula 17>
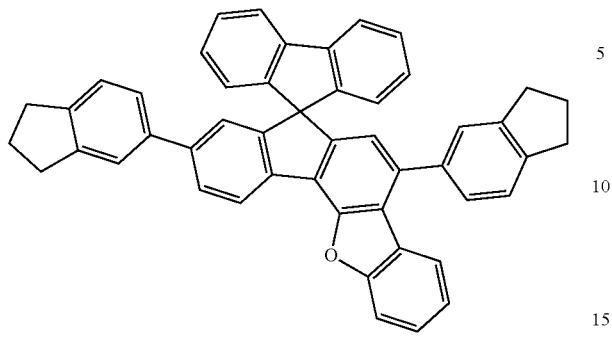
<Chemical Formula 18>
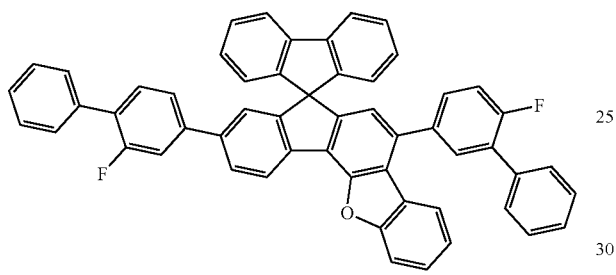
<Chemical Formula 19>
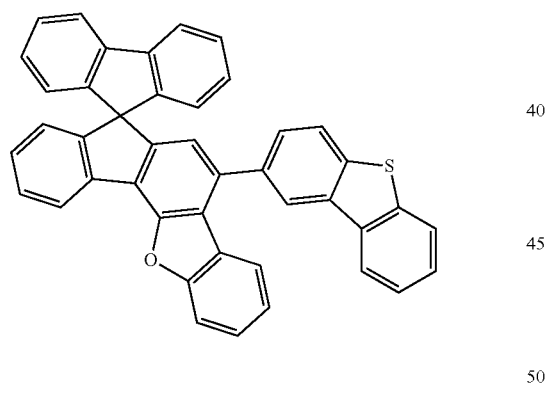
<Chemical Formula 20>
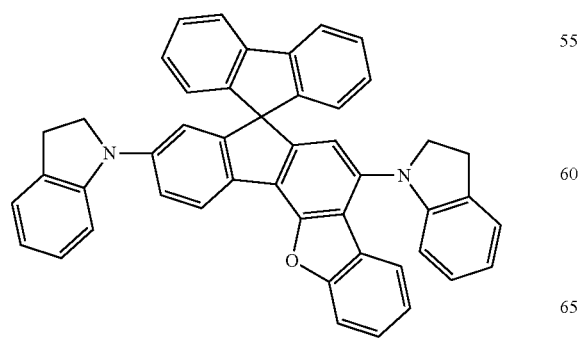
<Chemical Formula 21>
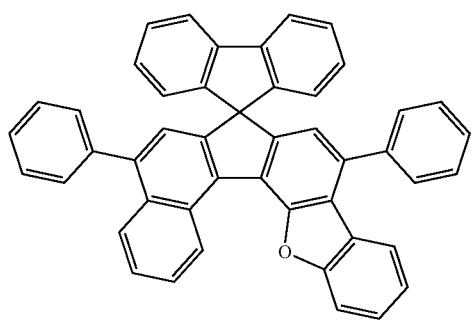
<Chemical Formula 22>
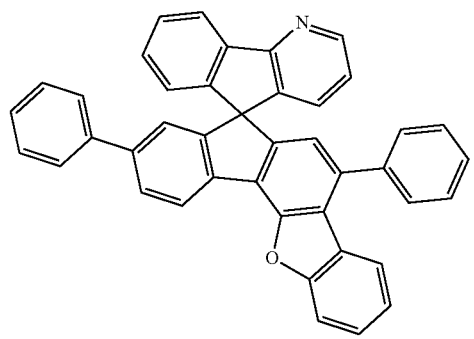
<Chemical Formula 23>
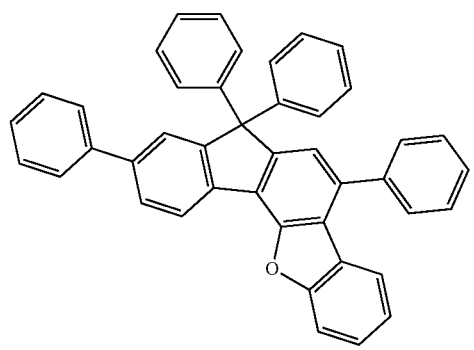
<Chemical Formula 24>
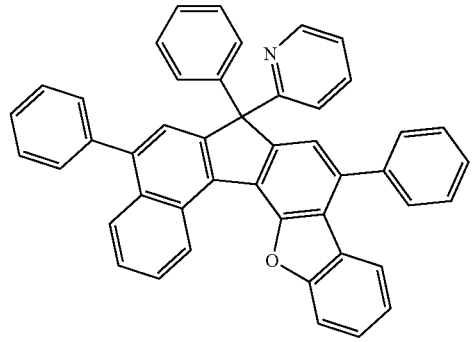

<Chemical Formula 25>
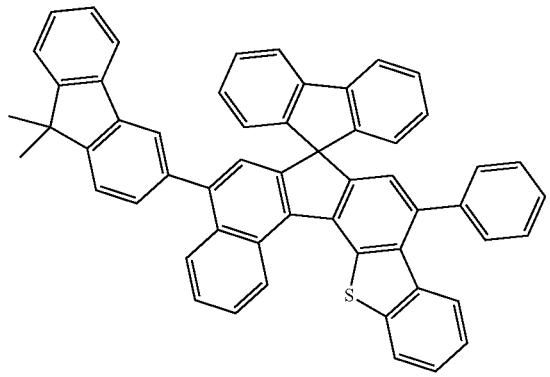
<Chemical Formula 26>
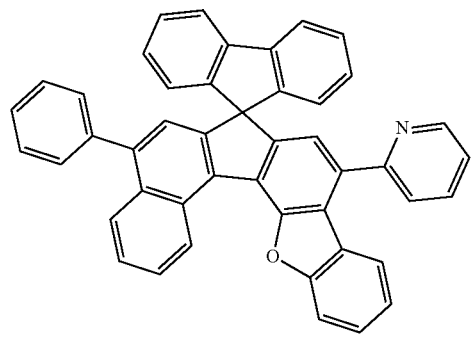
<Chemical Formula 27>
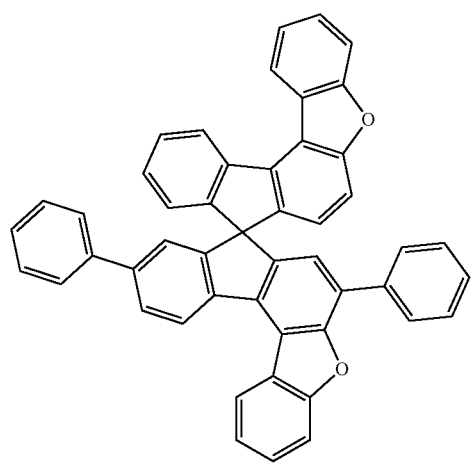
<Chemical Formula 28>
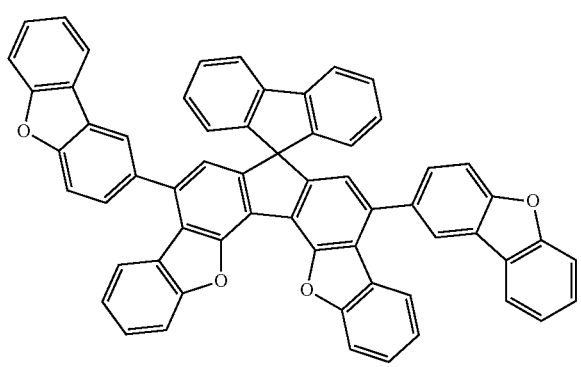
<Chemical Formula 29>
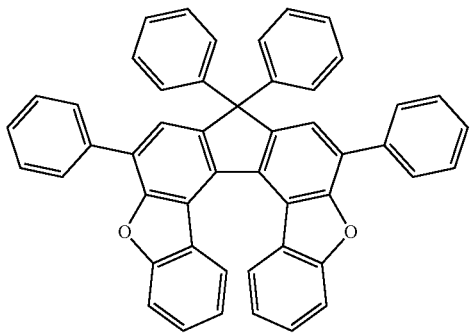
<Chemical Formula 30>
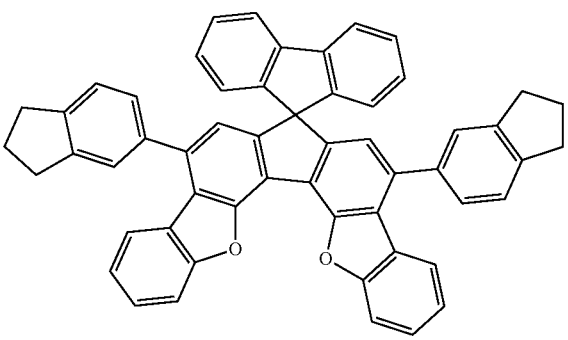
<Chemical Formula 31>
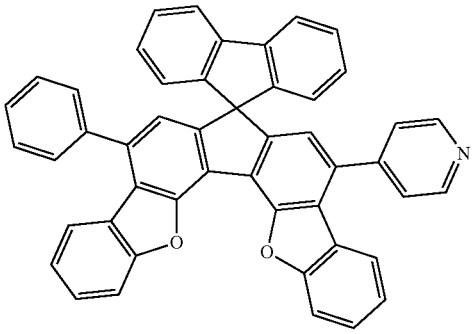
<Chemical Formula 32>
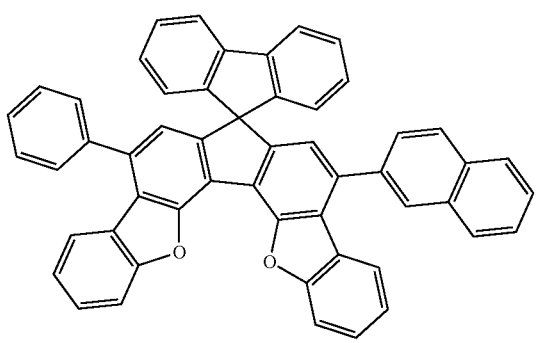

<Chemical Formula 33>
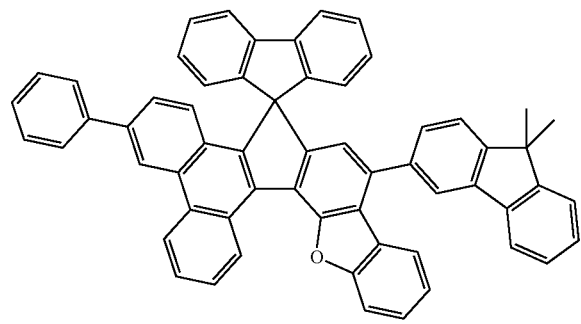
<Chemical Formula 34>
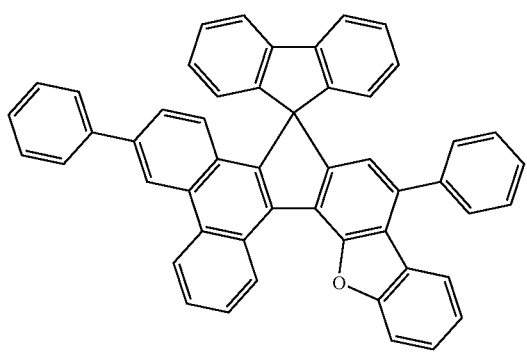
<Chemical Formula 35>
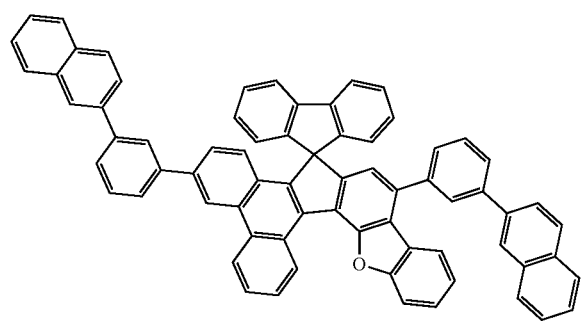
<Chemical Formula 36>
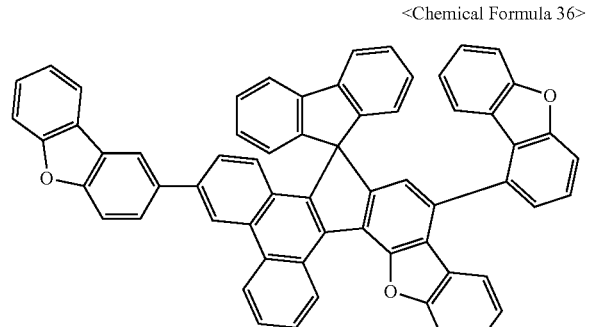
<Chemical Formula 37>
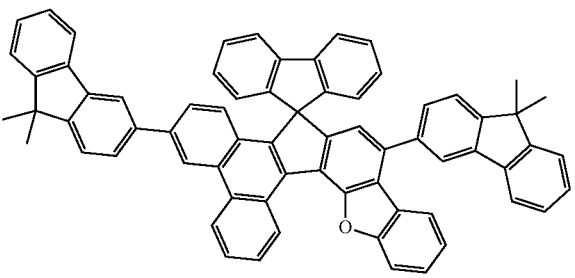
<Chemical Formula 38>
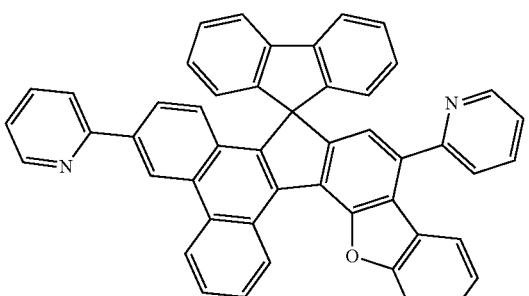
<Chemical Formula 39>
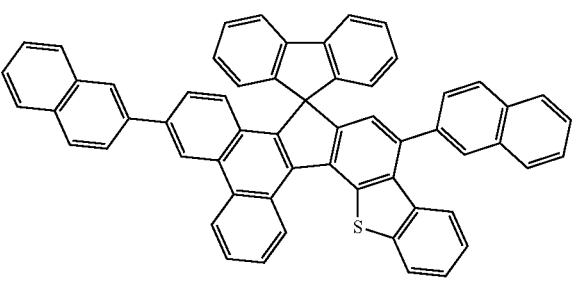
<Chemical Formula 40>
<Chemical Formula 41>
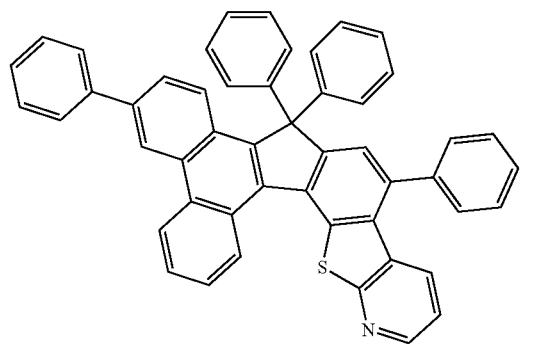

<Chemical Formula 42>
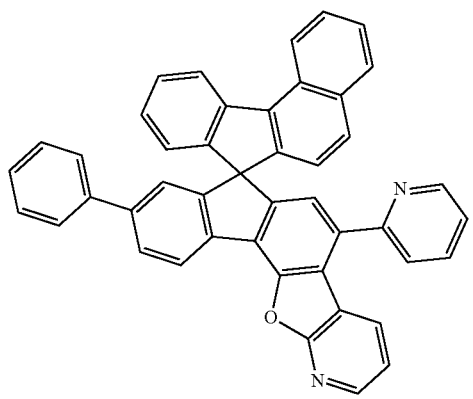
<Chemical Formula 43>
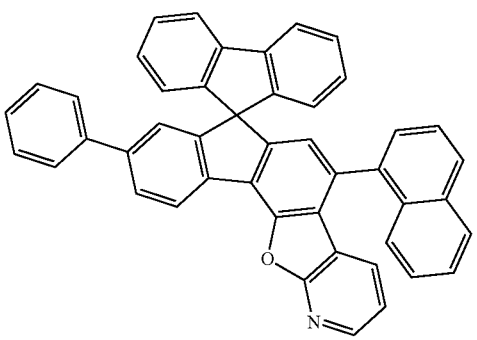
<Chemical Formula 44>
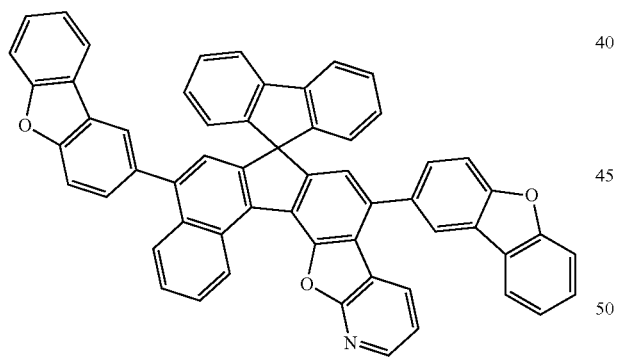
<Chemical Formula 45>
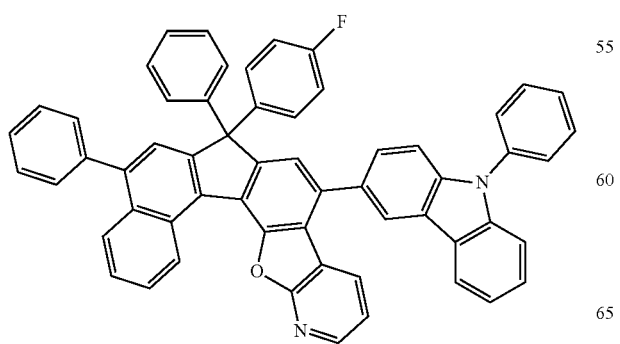
<Chemical Formula 46>
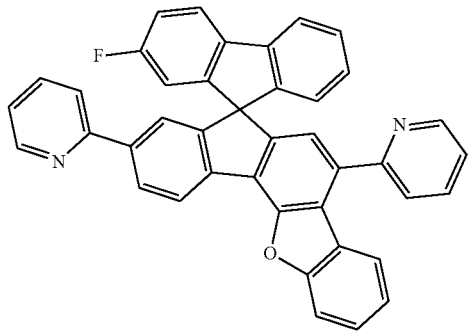
<Chemical Formula 47>
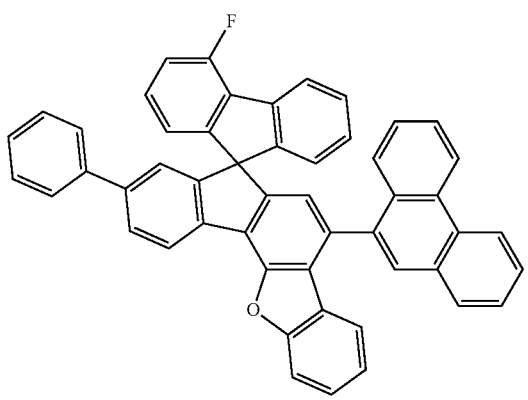
<Chemical Formula 48>
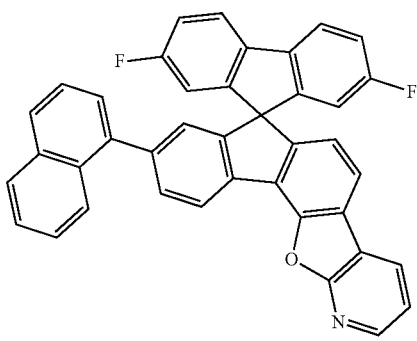
<Chemical Formula 49>
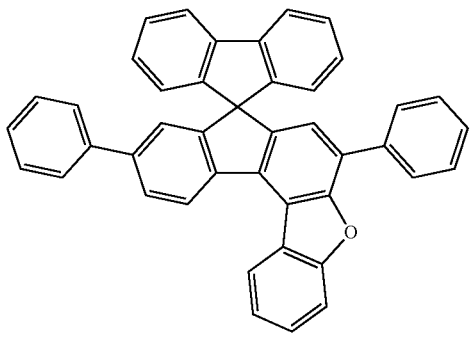

<Chemical Formula 50>
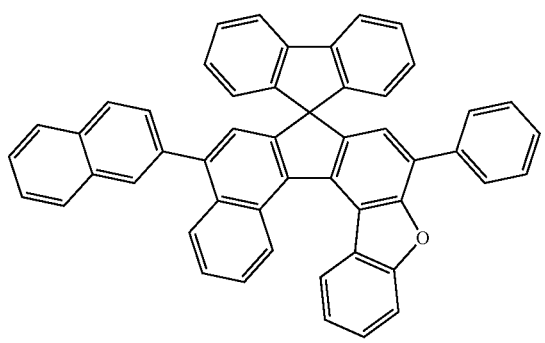
<Chemical Formula 52>
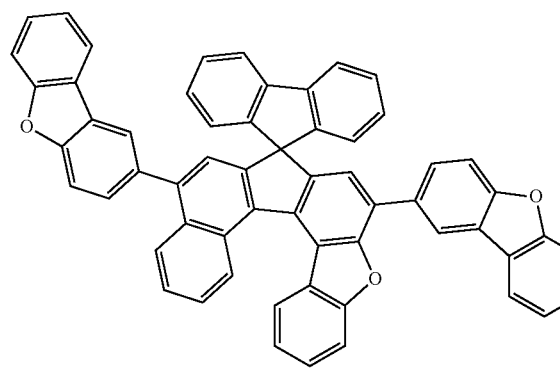
<Chemical Formula 53>
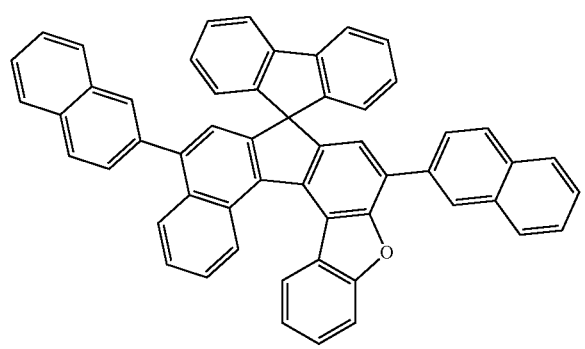
<Chemical Formula 54>
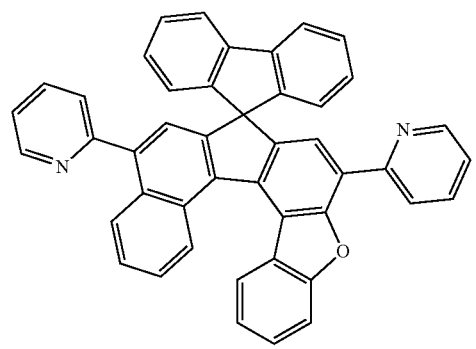
<Chemical Formula 55>
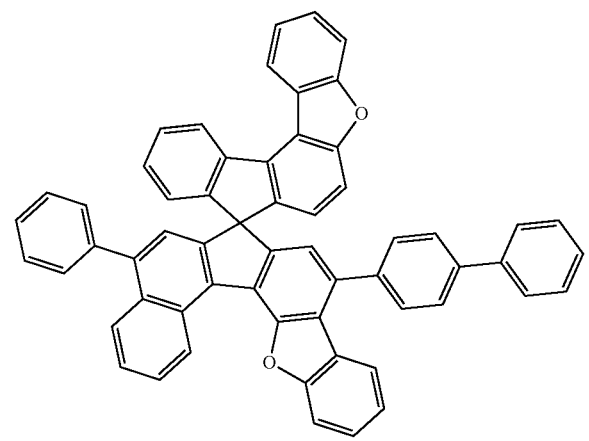
<Chemical Formula 56>
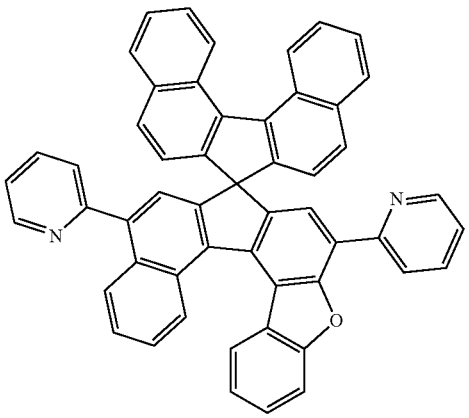
<Chemical Formula 57>
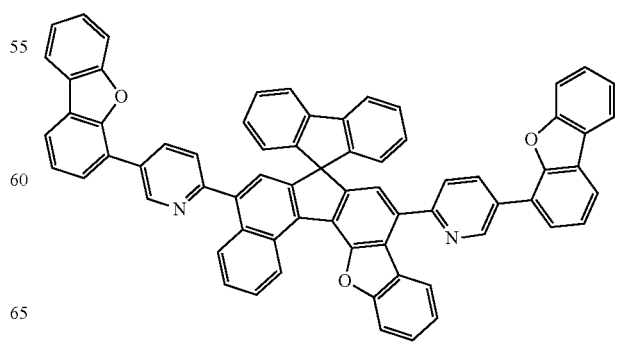

<Chemical Formula 58>
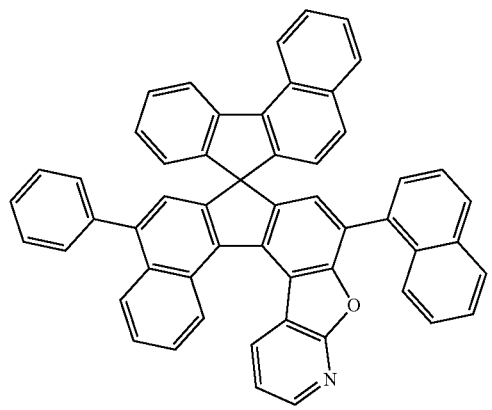
<Chemical Formula 59>
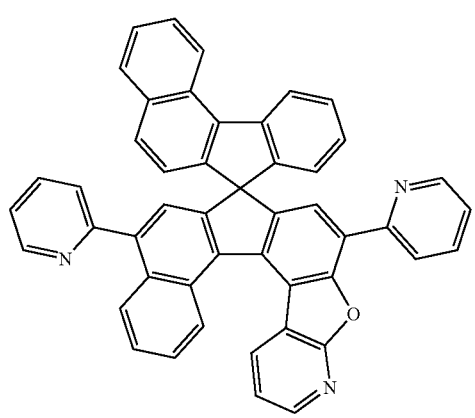
<Chemical Formula 60>
<Chemical Formula 61>
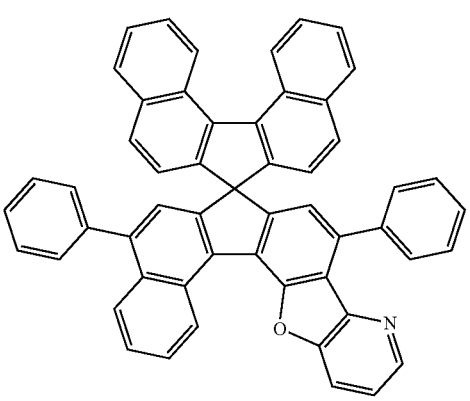
<Chemical Formula 62>
<Chemical Formula 63>
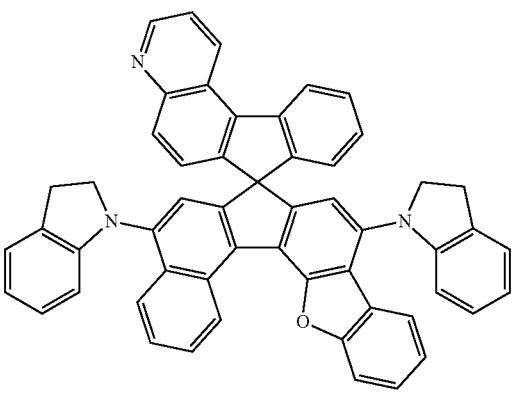
<Chemical Formula 64>
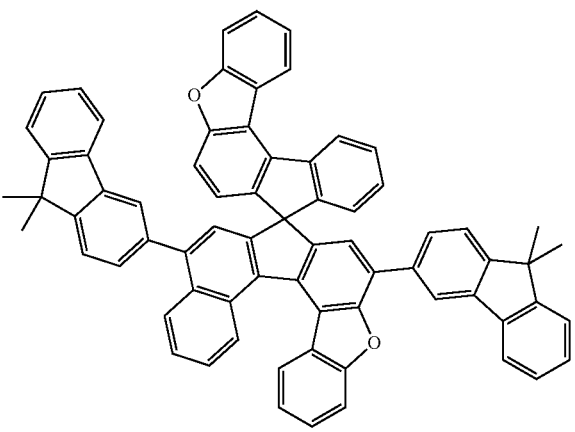

<Chemical Formula 65>
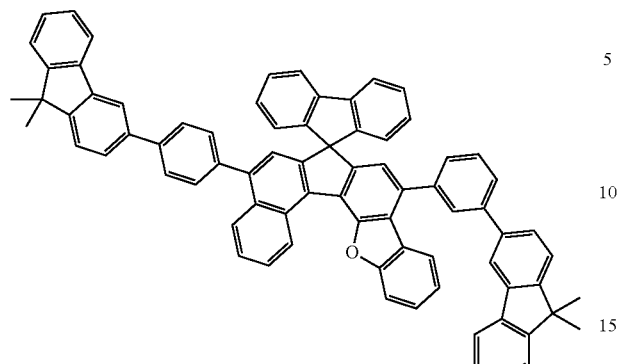
<Chemical Formula 66>
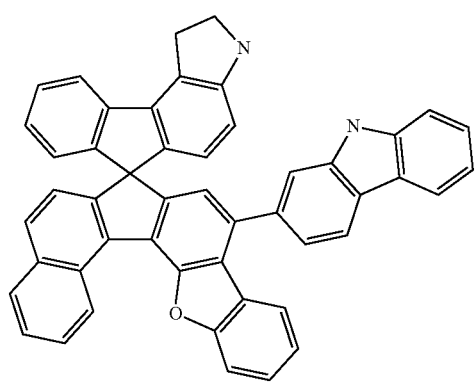
<Chemical Formula 67>
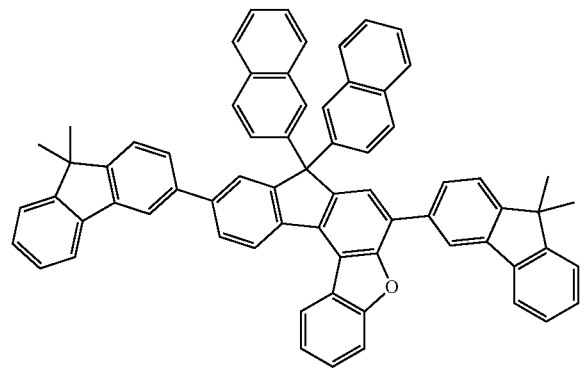
<Chemical Formula 68>
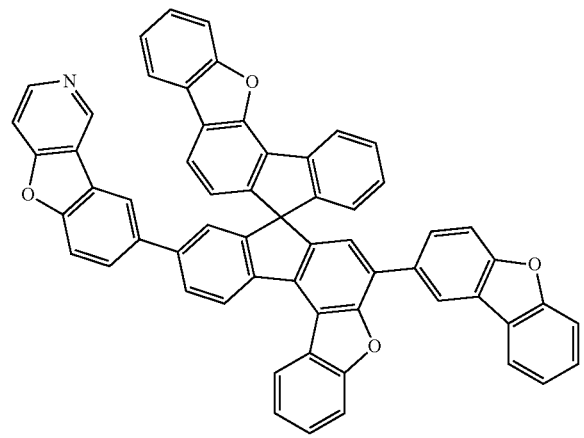
<Chemical Formula 69>
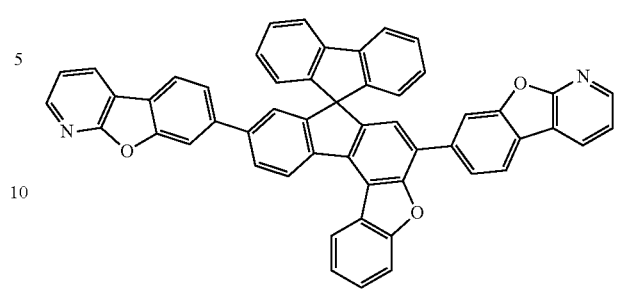
<Chemical Formula 70>
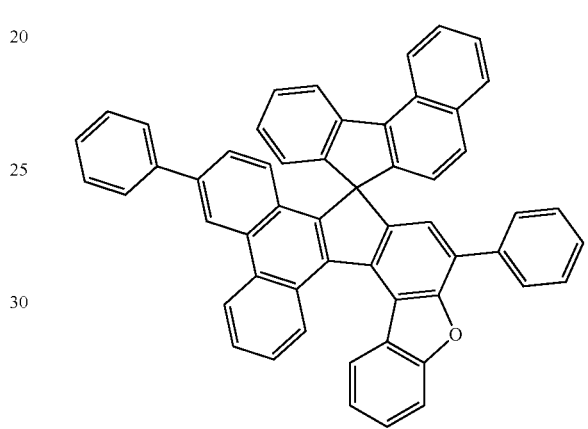
<Chemical Formula 71>
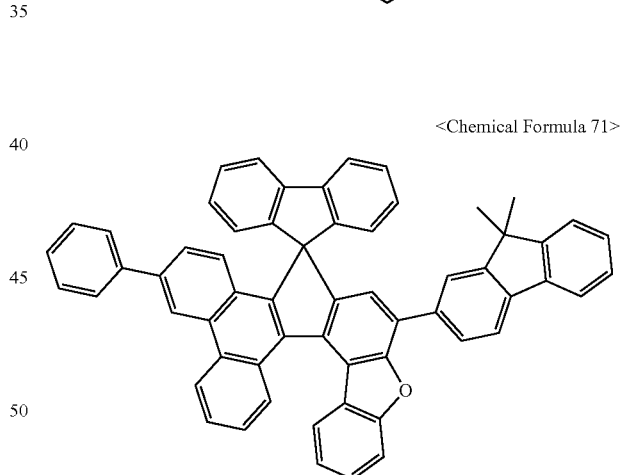
<Chemical Formula 72>
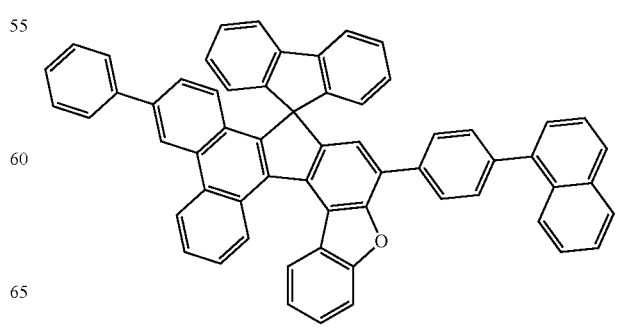

<Chemical Formula 73>
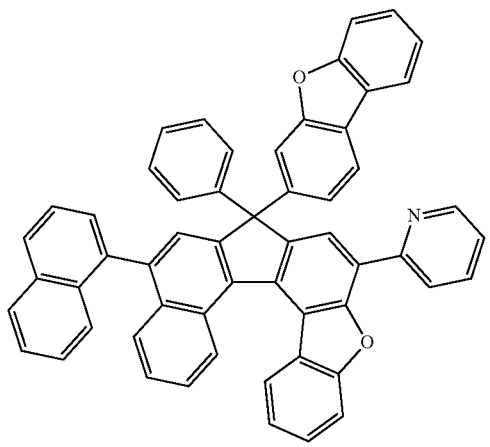
<Chemical Formula 74>
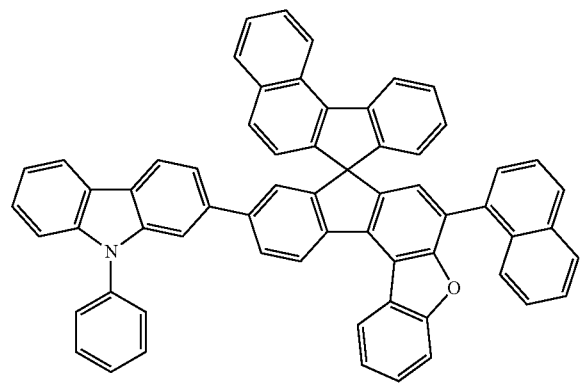
<Chemical Formula 75>
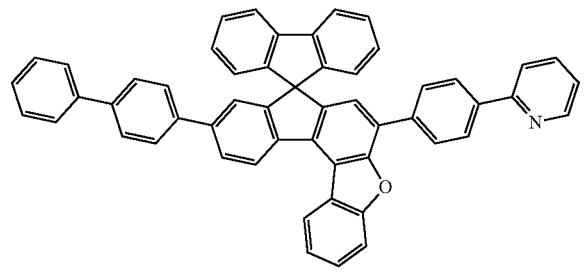
<Chemical Formula 76>
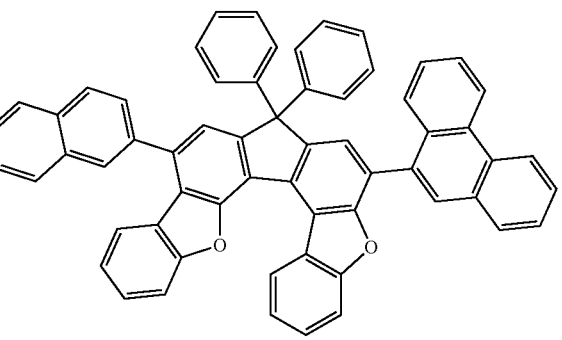
<Chemical Formula 77>
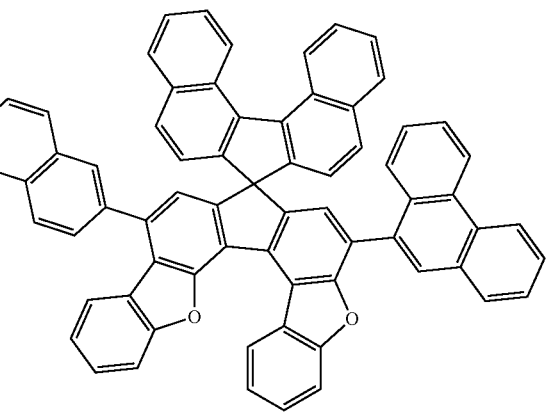
<Chemical Formula 78>
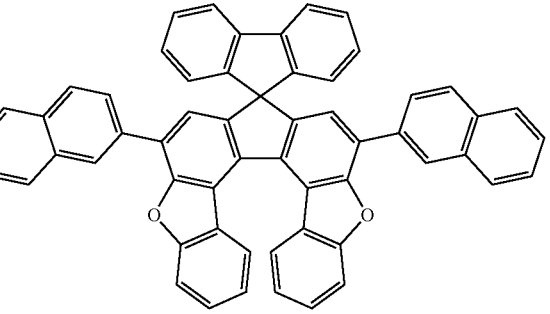
<Chemical Formula 79>
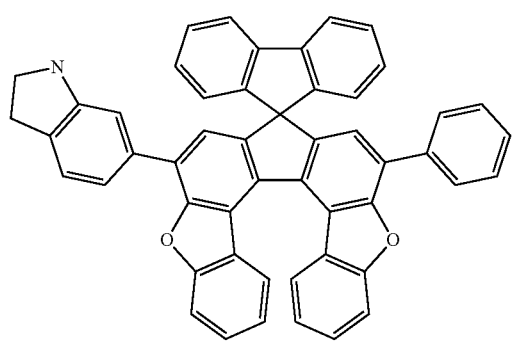
<Chemical Formula 80>

31

-continued

<Chemical Formula 81>

<Chemical Formula 82>

<Chemical Formula 83>

<Chemical Formula 84>

32

-continued

<Chemical Formula 85>

<Chemical Formula 86>

<Chemical Formula 87>

<Chemical Formula 88>

<Chemical Formula 89>
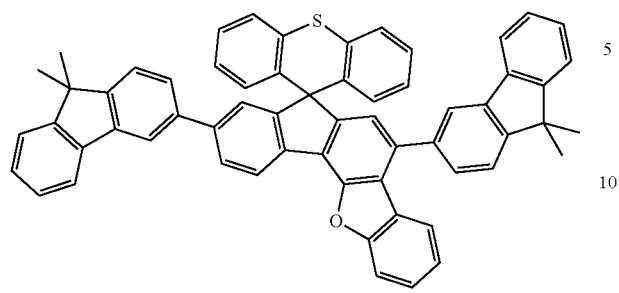
<Chemical Formula 90>
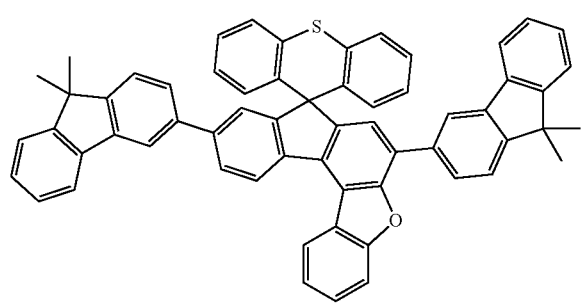
<Chemical Formula 91>
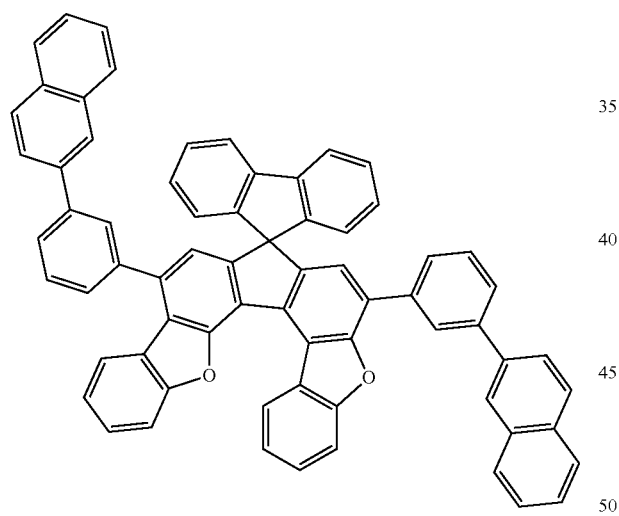
<Chemical Formula 92>
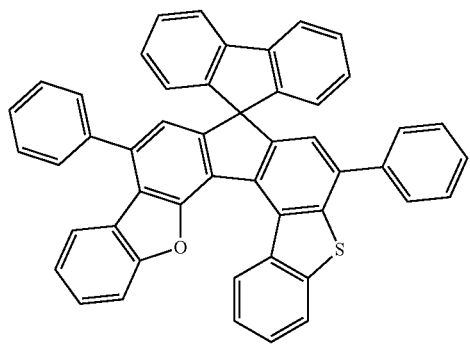
<Chemical Formula 93>
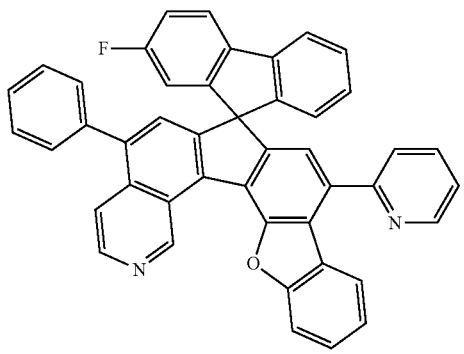
<Chemical Formula 94>
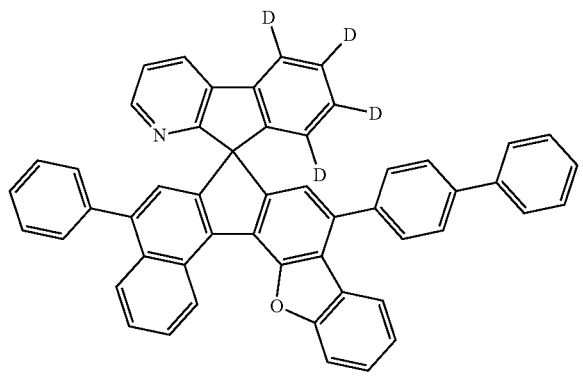
<Chemical Formula 95>
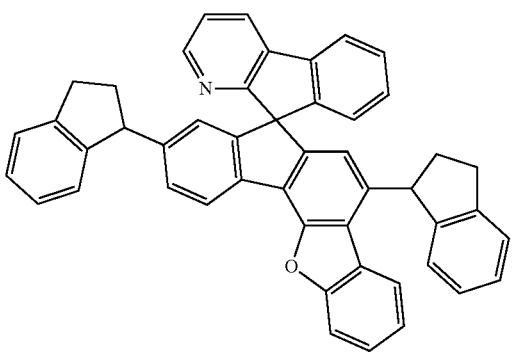
<Chemical Formula 96>
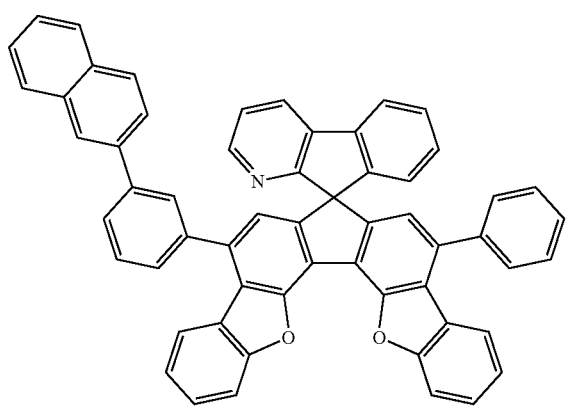

<Chemical Formula 97>
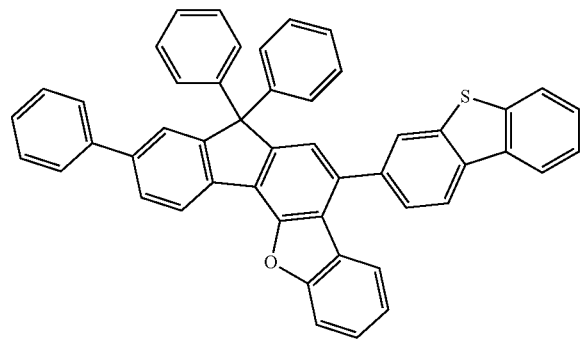
<Chemical Formula 98>
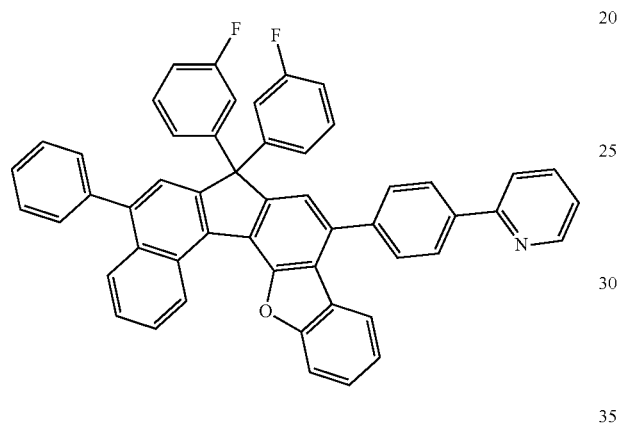
<Chemical Formula 99>
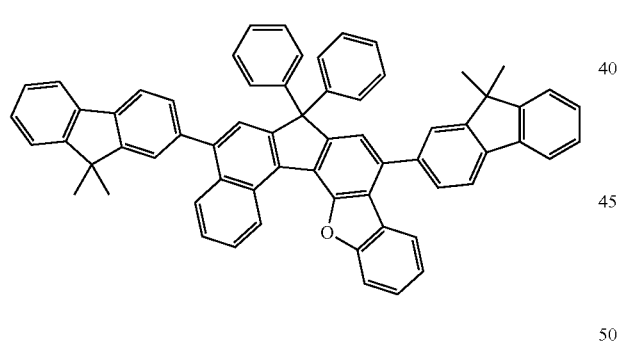
<Chemical Formula 100>
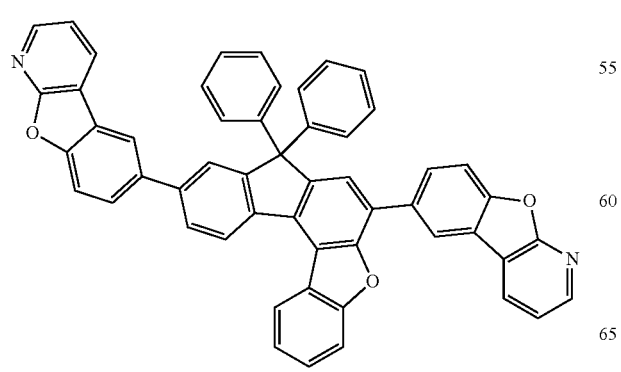
<Chemical Formula 101>
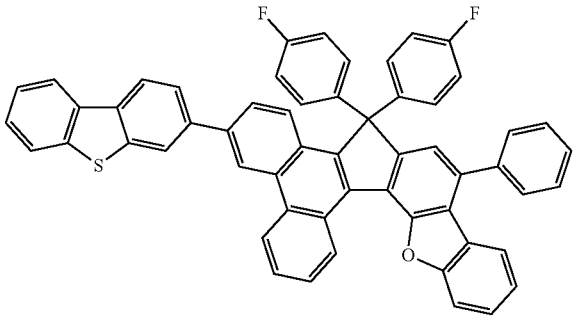
<Chemical Formula 102>
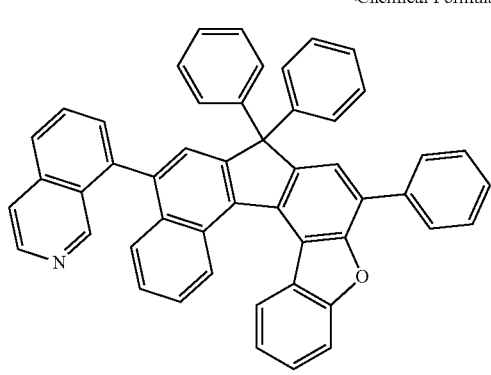
<Chemical Formula 103>
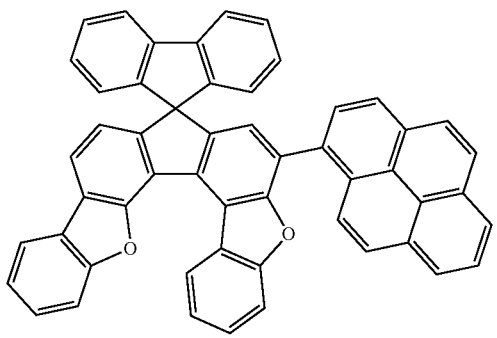
<Chemical Formula 104>
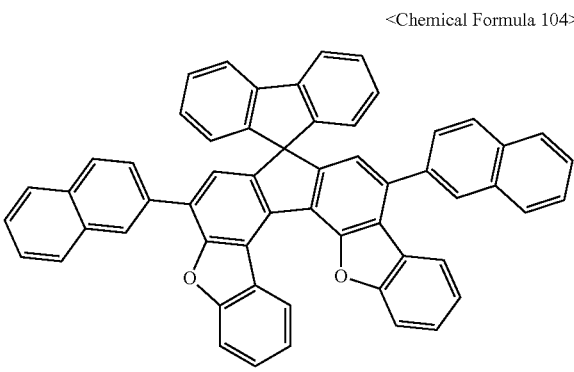

<Chemical Formula 105>
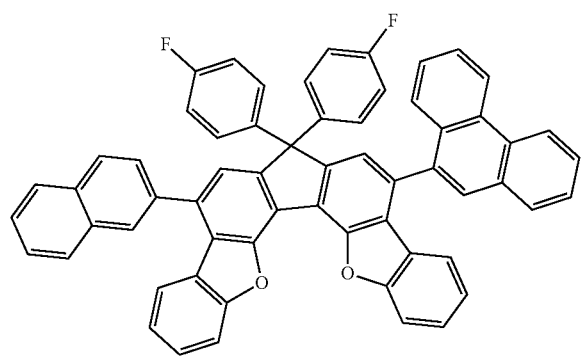
<Chemical Formula 106>
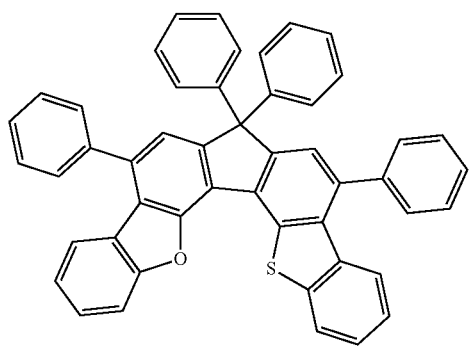
<Chemical Formula 107>
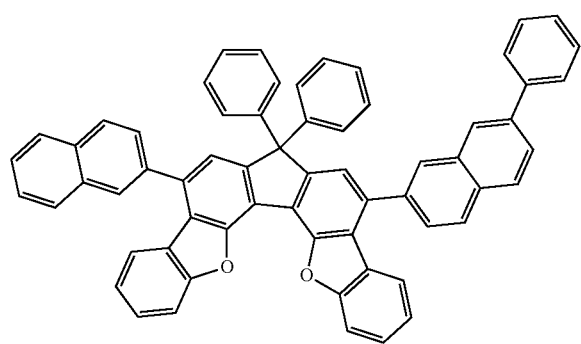
<Chemical Formula 108>
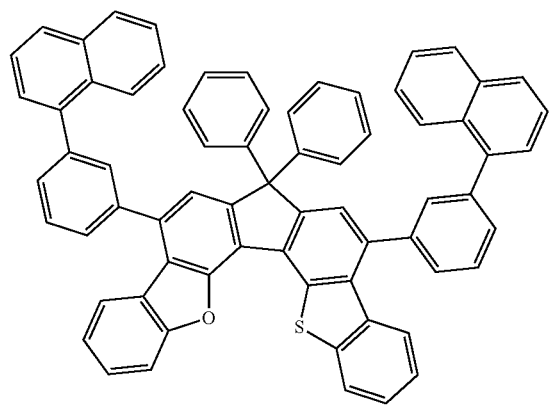
<Chemical Formula 109>
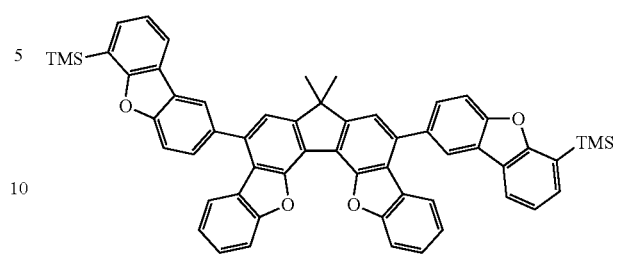
<Chemical Formula 110>
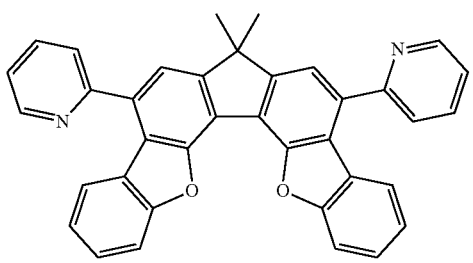
<Chemical Formula 111>
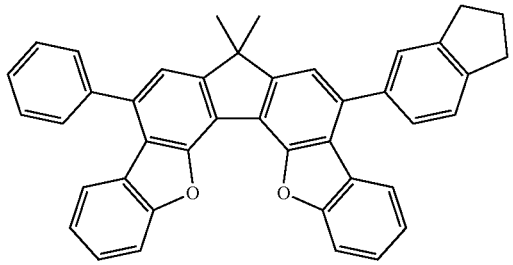
<Chemical Formula 112>
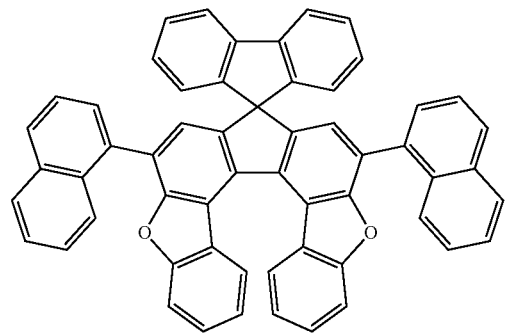
<Chemical Formula 113>
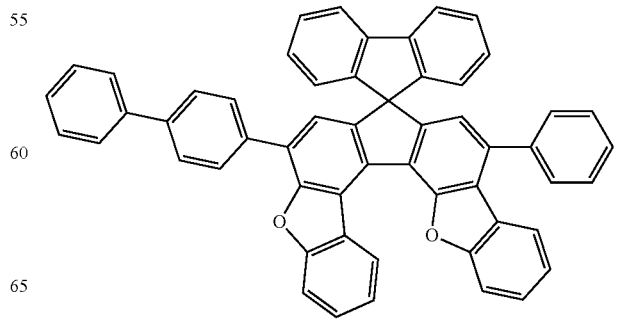

<Chemical Formula 114>
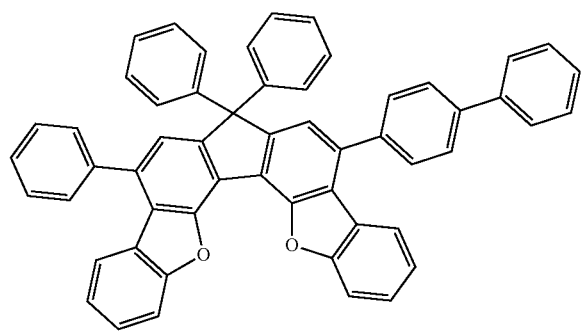
<Chemical Formula 115>
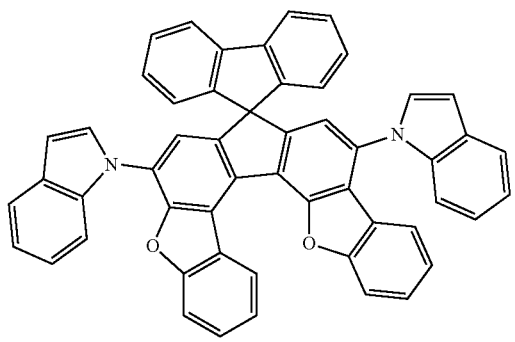
<Chemical Formula 116>
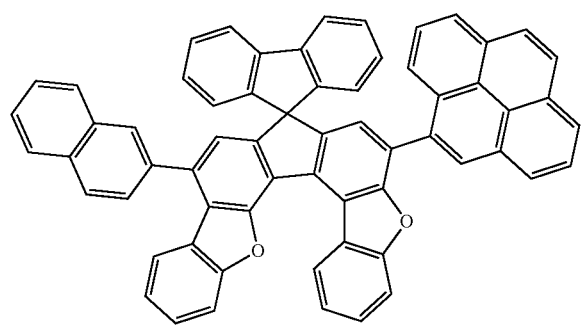
<Chemical Formula 117>
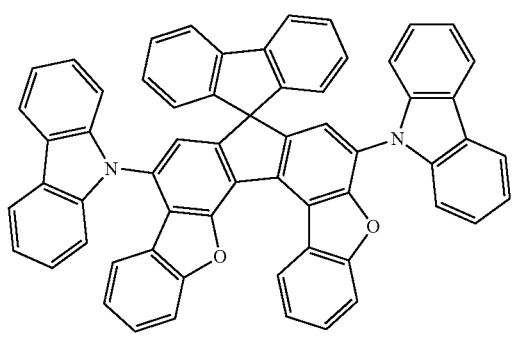
<Chemical Formula 118>
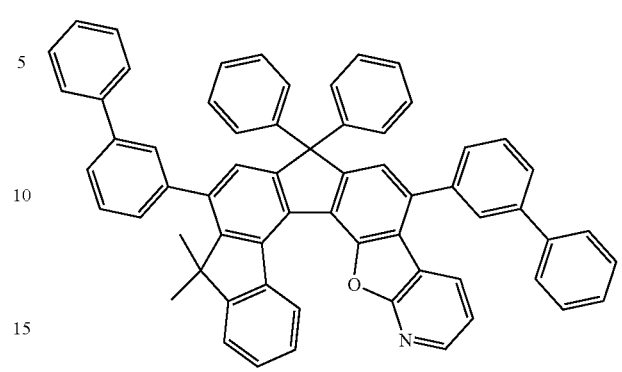
<Chemical Formula 119>
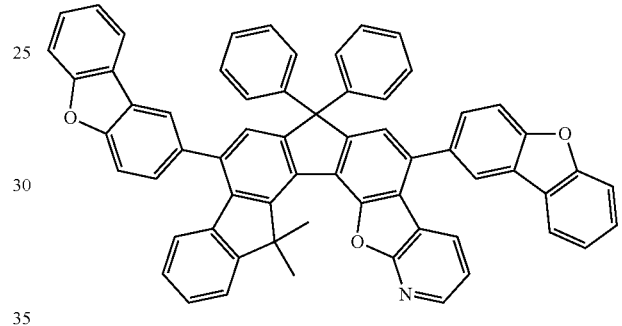
<Chemical Formula 120>
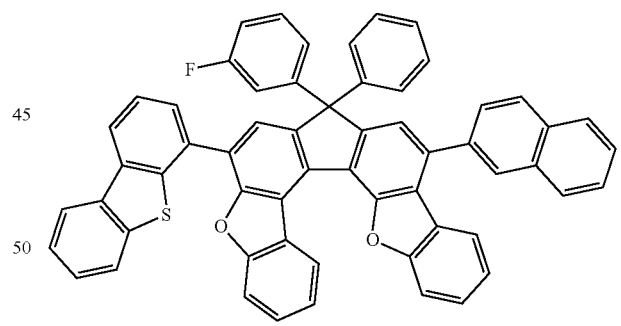
<Chemical Formula 121>
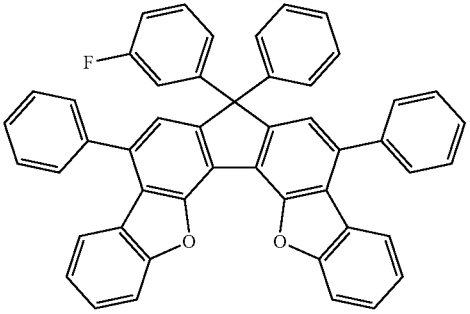

<Chemical Formula 122>

<Chemical Formula 123>

<Chemical Formula 124>

<Chemical Formula 125>

<Chemical Formula 126>

<Chemical Formula 127>

<Chemical Formula 128>

<Chemical Formula 129>

<Chemical Formula 130>
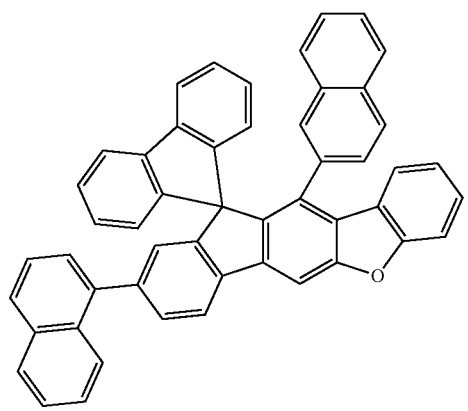
<Chemical Formula 131>
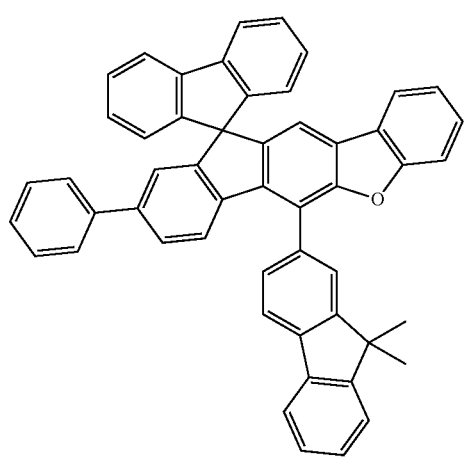
<Chemical Formula 132>
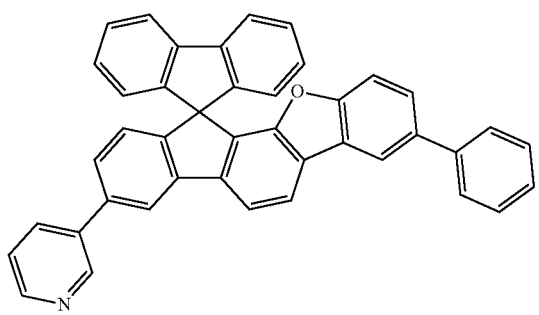
<Chemical Formula 133>
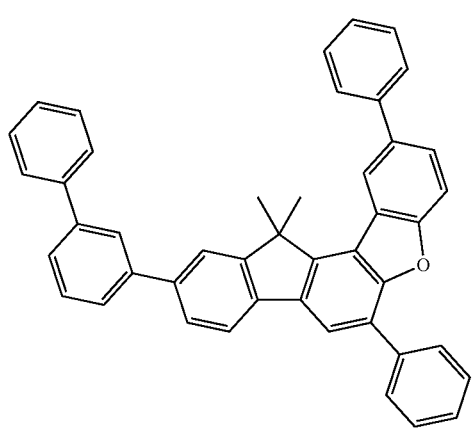
<Chemical Formula 134>
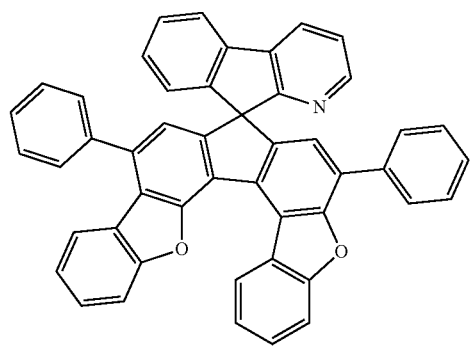
<Chemical Formula 135>
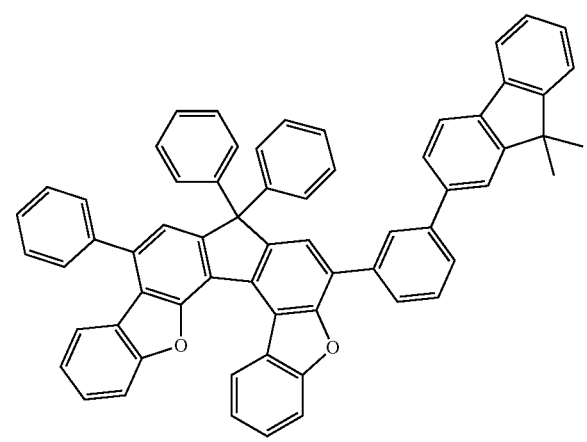
<Chemical Formula 136>
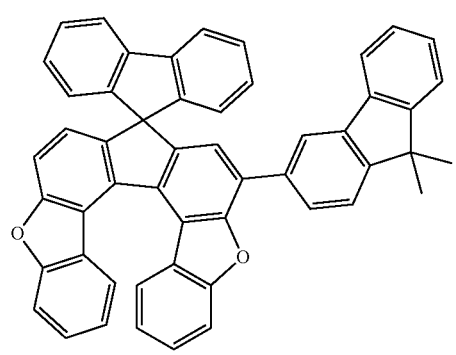

<Chemical Formula 137>

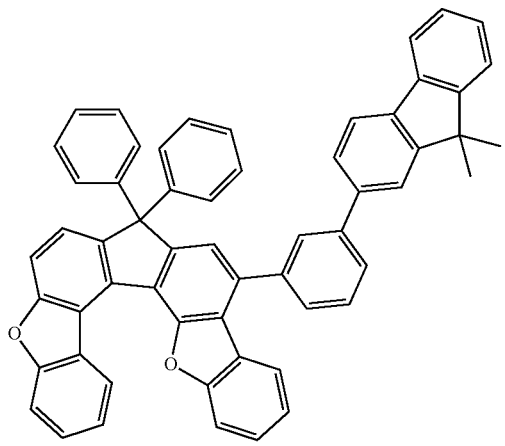

<Chemical Formula 138>

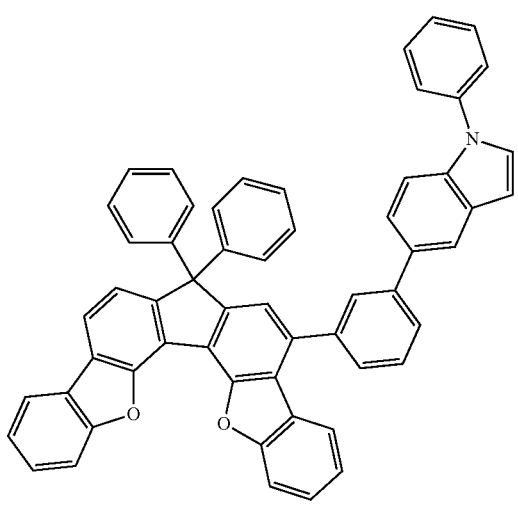

Also, the present disclosure provides an organic light-emitting diode, comprising a first electrode; a second electrode facing the first electrode; and an organic layer interposed therebetween, wherein the organic layer contains at least one of the compounds of the present disclosure.

As used herein, the expression "(the organic layer) contains at least one organic compound" is construed to mean that (the organic layer) may contain one organic compound falling within the scope of the present disclosure or two or more different compounds falling within the scope of the present disclosure.

According to some particular embodiments of the present disclosure, the organic layer containing the compound of the present disclosure may comprise at least one of a hole injecting layer, a hole transport layer, a functional layer capable of both hole injection and hole transport, a light-emitting layer, an electron transport layer, and an electron injecting layer.

In addition, the organic layer interposed between the first electrode and the second electrode may be a light-emitting layer. In this regard, the light-emitting layer may be composed of a host and a dopant, and the compound of Chemical Formula A or B may be used as the host.

Concrete examples of the dopant material used in the light-emitting layer include pyrene compounds, deuterium-substituted pyrene compounds, aryl amines, deuterium-substituted aryl amines, perylene compounds, deuterium-substituted perylene compounds, pyrrole compounds, deuterium-substituted pyrrole compounds, hydrazone compounds, deuterium-substituted hydrazone compounds, carbazole compounds, deuterium-substituted carbazole compounds, stilbene compounds, deuterium-substituted stilbene compounds, starburst-type compounds, deuterium-substituted starburst-type compounds, oxadiazole compounds, deuterium-substituted oxadiazole compounds, coumarin, and deuterium-substituted coumarin, but are not limited thereto.

When the light-emitting layer comprises a host and a dopant, the content of the dopant may range from about 0.01 to 20 parts by weight, based on 100 parts by weight of the host, but is not limited thereto.

Further, one or more layers selected from among a hole injecting layer, a hole transport layer, a functional layer capable of both hole injection and hole transport, a light-emitting layer, an electron transport layer, and an electron injecting layer may be deposited using a single-molecule deposition process or a solution process.

Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

In one embodiment of the present disclosure, a hole transport layer (HTL) may be further deposited between the anode and the organic light-emitting layer while an electron transport layer (ETL) may be further deposited between the cathode and the organic light-emitting layer.

As a material for the hole transport layer, an electron donating molecule with low ionization potential is used. Predominantly, diamine, triamine or tetraamine derivatives having a triphenylamine skeleton are employed. For example, N,N'-bis(3-methylphenyl)-N,N'-diphenyl-[1,1-biphenyl]-4,4'-diamine (TPD) or N,N'-di(naphthalen-1-yl)-N, N'-diphenylbenzidine (a-NPD) may be used.

A hole injecting layer (HIL) may be further deposited beneath the hole transport layer. No particular limitations are imposed on the hole injecting layer material, as long as it is one that is typically used in the art. Examples include CuPc (copperphthalocyanine), and the starburst amines TCTA (4,4',4''-tri(N-carbazolyl)triphenyl-amine), and m-MTDATA (4,4',4''-tris-(3-methylphenylphenyl amino)triphenylamine).

For the electron transport layer, by way of example, the oxadiazole derivatives PBD, BMD, and BND, or Alq$_3$ may be used.

An electron injecting layer (EIL) that functions to facilitate electron injection from the cathode, thus improving the power efficiency of the diode, may be further deposited on the electron transport layer. So long as it is conventionally used in the art, any material can be available for the electron injecting layer without particular limitations. Examples include LiF, NaCl, CsF, Li$_2$O, and BaO.

Below, the organic light-emitting diode of the present disclosure is explained with reference to FIG. 1.

FIG. 1 is a schematic cross-sectional view of the structure of an organic light-emitting diode according to the present disclosure. The organic light-emitting diode comprises an anode 20, a hole transport layer 40, an organic light-emitting layer 50, an electron transport layer 60, and a cathode 80, and optionally a hole injecting layer 30 and an electron injecting layer 70. In addition, one or two intermediate layers may be further formed in the organic light-emitting diode.

Reference is made to FIG. 1 with regard to the organic light-emitting diode of the present disclosure and the fabrication thereof. First, a substrate 10 is coated with an anode electrode material to form an anode 20. So long as it is used in a typical organic EL device, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide ($SnO_2$), or zinc oxide (ZnO), which are transparent and superior in terms of conductivity, may be used.

A hole injecting layer material is applied on the anode electrode 20 by thermal deposition in a vacuum or by spin coating to form a hole injecting layer 30. Subsequently, thermal deposition in a vacuum or by spin coating may also be conducted to form a hole transport layer 40 with a hole transport layer material on the hole injecting layer 30.

Then, an organic light-emitting layer 50 is deposited on the hole transport layer 40, optionally followed by the formation of a hole barrier layer (not shown) on the organic light-emitting layer 50 by deposition in a vacuum or by spin coating. When holes traverse the organic light-emitting layer and are introduced into the cathode, the efficiency and lifespan of the diode are deteriorated. Formed of a material with a low HOMO (Highest Occupied Molecular Orbital) level, the hole barrier layer serves to prevent the introduction of holes into the cathode. Any material that has a higher ionization potential than the light-emitting compound and which is also able to carry electrons may be used for the hole barrier layer without limitations. Representative among hole barrier materials are BAlq, BCP, and TPBI.

Using a vacuum deposition method or a spin-coating method, an electron transport layer 60 may be deposited on the hole barrier layer and may then be overlaid with an electron injection layer 70. A cathode metal is deposited on the electron injection layer 70 by thermal deposition in a vacuum to form a cathode 80, thus obtaining an organic EL diode. Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

In some embodiments of the present disclosure, the light-emitting layer particularly ranges in thickness from 50 to 2,000 Å. In addition, the light-emitting layer may be composed of a host and a dopant wherein the host may be the compound of the present disclosure.

The dopant may be a compound represented by Chemical Formula D1 or D2. In this regard, the light-emitting layer may further contain various dopant materials.

[Chemical Formula D1]

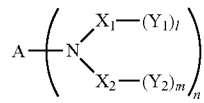

[Chemical Formula D2]

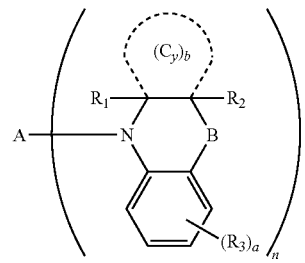

wherein,

A may be any one selected from among a substituted or unsubstituted aryl of 5 to 50 carbon atoms, a substituted or unsubstituted heteroaryl of 3 to 50 carbon atoms bearing O, N, or S as a heteroatom, a substituted or unsubstituted arylene of 6 to 60 carbon atoms, and a substituted or unsubstituted heteroarylene of 2 to 50 carbon atoms bearing O, N, or S as a heteroatom.

In greater detail, A may be a substituted or unsubstituted arylene of 6 to 60 carbon atoms, or a single bond, particularly any one selected from among anthracene, pyrene, phenanthrene, indenophenanthrene, chrysene, naphthacene, picene, triphenylene, perylene, and pentacene, and more particularly a substituent represented by the following Chemical Formulas A1 to A10:

[Chemical Formula A1]

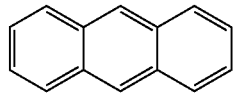

[Chemical Formula A2]

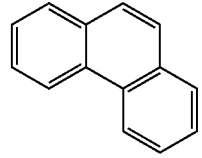

[Chemical Formula A3]

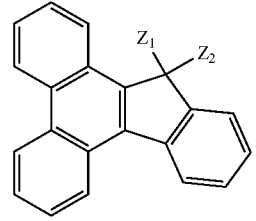

[Chemical Formula A4]

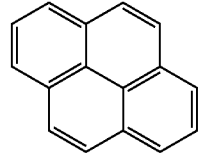

[Chemical Formula A5]

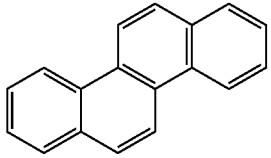

-continued

[Chemical Formula A6]

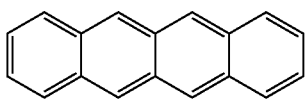

[Chemical Formula A7]

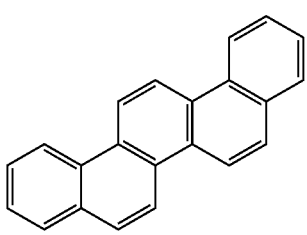

[Chemical Formula A8]

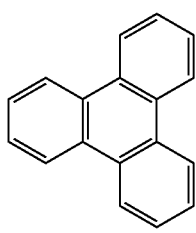

[Chemical Formula A9]

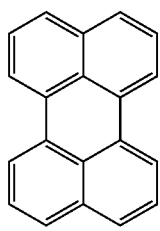

[Chemical Formula A10]

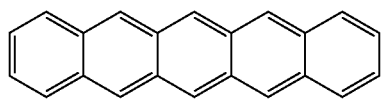

In Chemical Formula A3, $Z_1$ and $Z_2$ may be the same or different and are each independently selected from the group consisting of a hydrogen atom, a deuterium atom, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 6 to 60 carbon atoms, a substituted or unsubstituted arylthio of 6 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms or a (substituted or unsubstituted aryl)amino of 6 to 60 carbon atoms, and a di(substituted or unsubstituted aryl) amino of 6 to 60 carbon atom, with the proviso that $Z_1$ and $Z_2$ may each form a fused ring with an adjacent radical.

In Chemical Formula D1,
$X_1$ and $X_2$ may each be independently a substituted or unsubstituted arylene of 6 to 30 carbon atoms or a single bond, with the proviso that $X_1$ and $X_2$ may bond to each other,
$Y_1$ and $Y_2$ may be the same or different and are each independently selected from the group consisting of a substituted or unsubstituted aryl of 6 to 24 carbon atoms, a substituted or unsubstituted a heteroaryl of 2 to 24 carbon atoms, a substituted or unsubstituted alkyl of 1 to 24 carbon atoms, a substituted or unsubstituted a heteroalkyl of 1 to 24 carbon atoms, a substituted or unsubstituted cycloalkyl of 3 to 24 carbon atoms, a substituted or unsubstituted alkoxy of 1 to 24 carbon atoms, a cyano, a halogen, a substituted or unsubstituted aryloxy of 6 to 24 carbon atoms, a substituted or unsubstituted alkylsilyl of 1 to 40 carbon atoms, a substituted or unsubstituted arylsilyl of 6 to 30 carbon atoms, a germanium, a phosphorus, a boron, a deuterium, and a hydrogen, with the proviso that $Y_1$ and $Y_2$ may each form with an aliphatic, aromatic, heteroaliphatic or heteroaromatic fused ring with an adjacent radical, l and m are each an integer of 1 to 20, and n is an integer of 1 to 4.

In Chemical Formula D2,
$C_y$ is a substituted or unsubstituted cycloalkyl of 3 to 8 carbon atoms and b is an integer of 1 to 4, with the proviso that when b is 2 or greater, the corresponding cycloalkanes may be the same or different and may be in a fused form having a deuterium or an alkyl as a substituent.

B is a single bond or —[C($R_5$)($R_6$)]$_p$— wherein p is an integer of 1 to 3, with the proviso that when p is 2 or greater, the corresponding $R_5$'s and $R_6$'s are individually the same or different;

$R_1$, $R_2$, $R_3$, $R_5$, and $R_6$ may each be independently selected from among a hydrogen atom, a deuterium atom, a halogen atom, a hydroxyl, a cyano, a nitro, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms(alkylthio), a substituted or unsubstituted cycloalkyl of 3 to 60 carbon atoms, a substituted or unsubstituted aryl of 6 to 60 carbon atoms, a substituted or unsubstituted aryloxy of 6 to 60 carbon atoms, a substituted or unsubstituted arylthio of 6 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms or a (substituted or unsubstituted aryl) amino of 6 to 60 carbon atoms, and a di(substituted or unsubstituted aryl)amino of 6 to 60 carbon atoms, a substituted or unsubstituted alkylsilyl of 1 to 40 carbon atoms, a substituted or unsubstituted arylsilyl of 6 to 30 carbon atoms, a germanium, a phosphorus, and a boron, a is an integer of 1 to 4, with the proviso that a is 2 or greater, the corresponding plural $R_3$'s may be the same or different and may be individually in a fused form, and n is an integer of 1 to 4.

The amine radical of Chemical Formulas D1 and D2, which is linked to A, may be represented by any one selected from among, but not limited to, the following Substituents 1 to 52:

[Substituent 1]
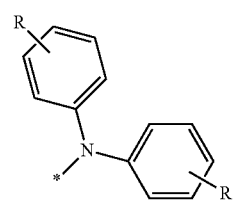
[Substituent 2]
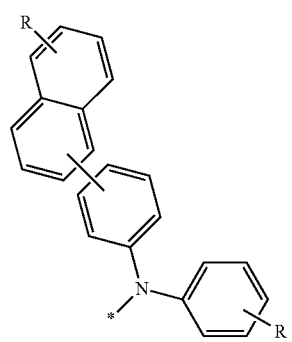
[Substituent 3]
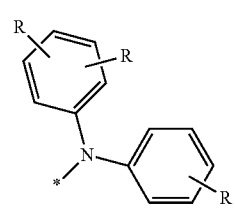
[Substituent 4]
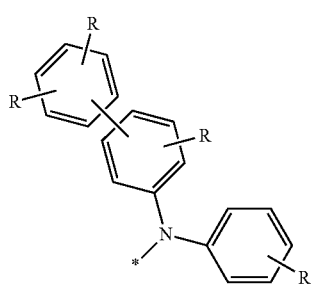
[Substituent 5]
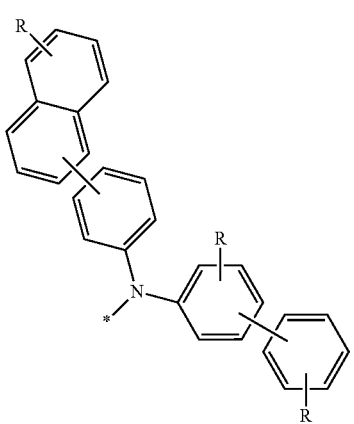
[Substituent 6]
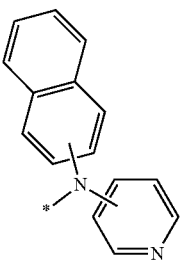
[Substituent 7]
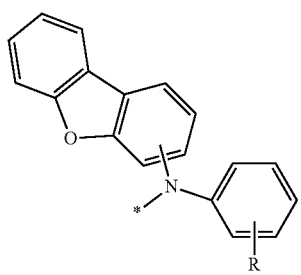
[Substituent 8]
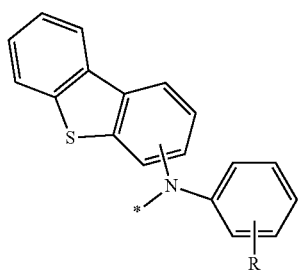
[Substituent 9]
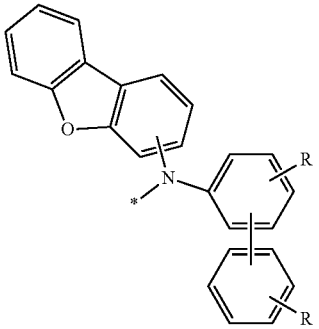
[Substituent 10]
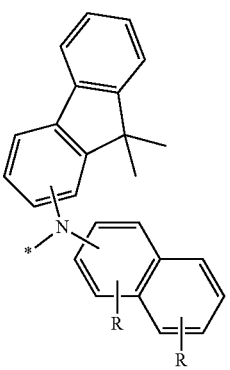

-continued
[Substituent 11]
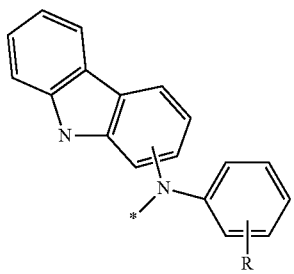
[Substituent 12]
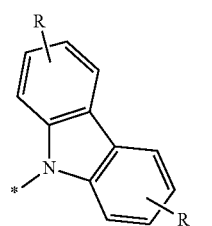
[Substituent 13]
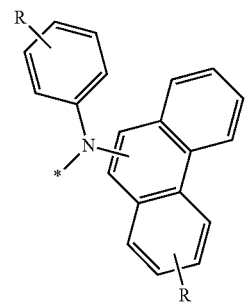
[Substituent 14]
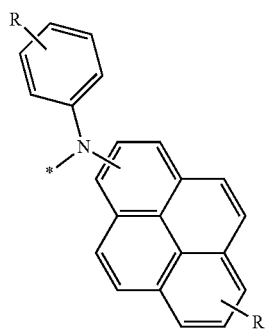
[Substituent 15]
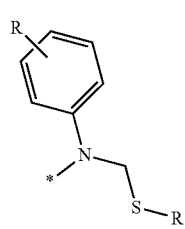
[Substituent 16]
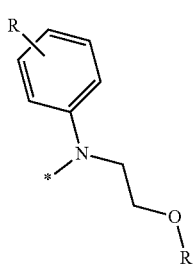
-continued
[Substituent 17]
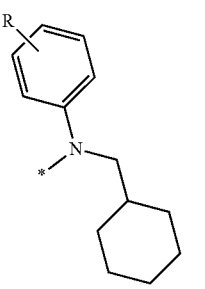
[Substituent 18]
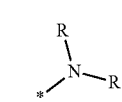
[Substituent 19]
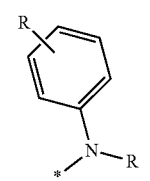
[Substituent 20]
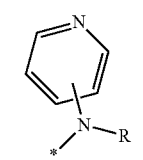
[Substituent 21]
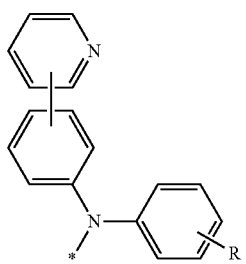
[Substituent 22]
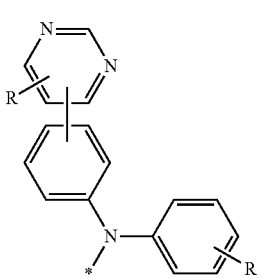
[Substituent 23]
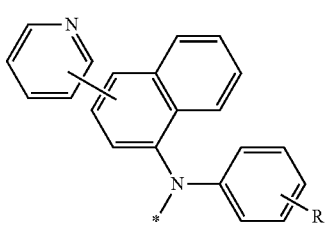

[Substituent 24]
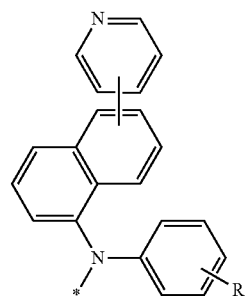
[Substituent 25]
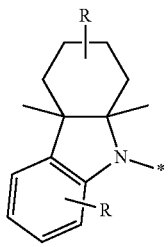
[Substituent 26]
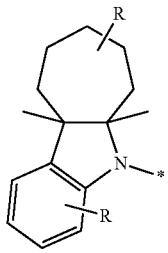
[Substituent 27]
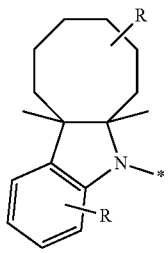
[Substituent 28]
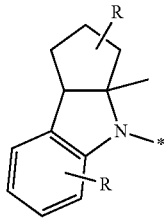
[Substituent 29]
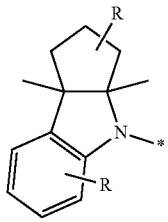
[Substituent 30]
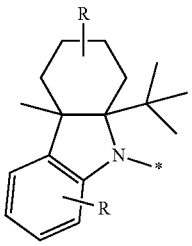
[Substituent 31]
[Substituent 32]
[Substituent 33]
[Substituent 34]

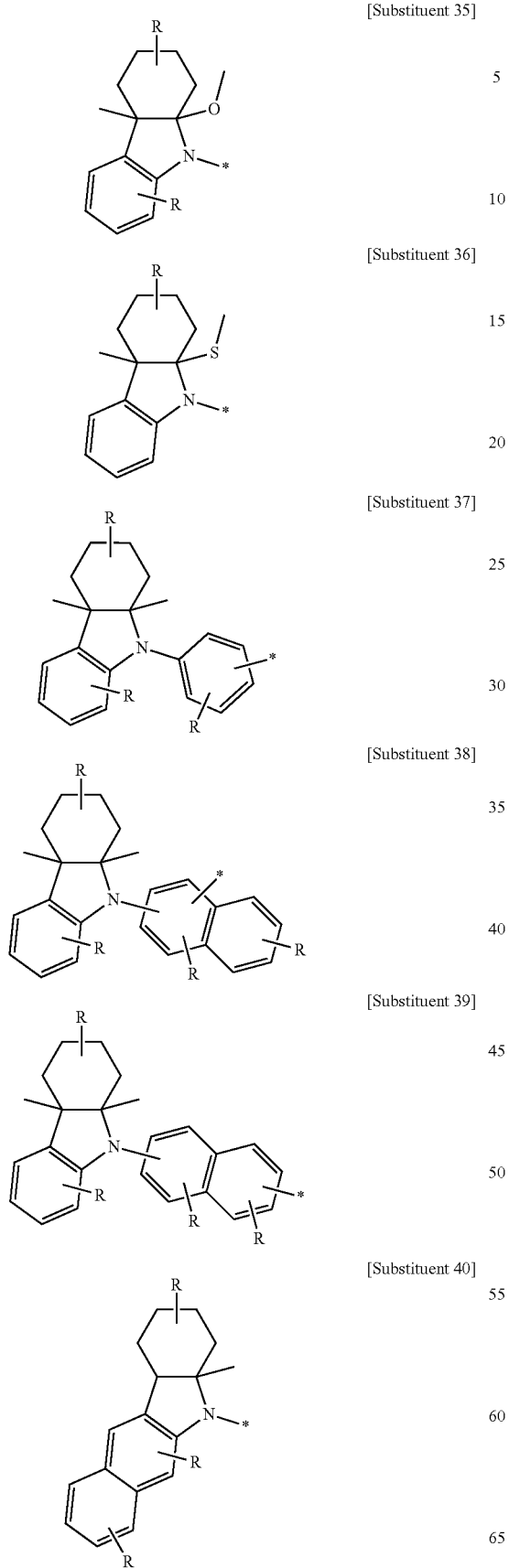
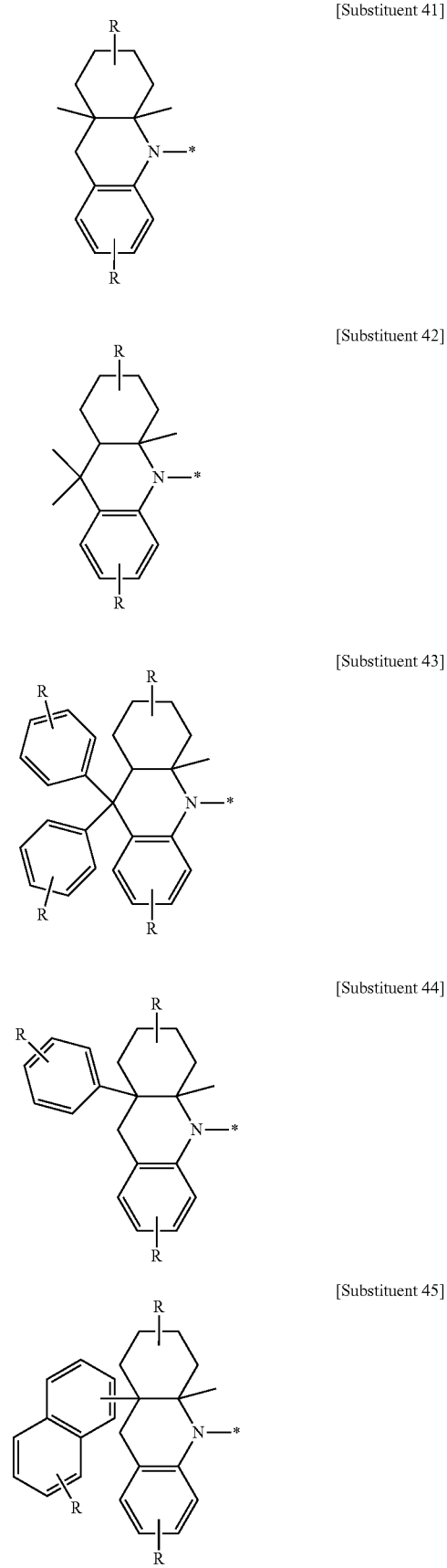

[Substituent 46]

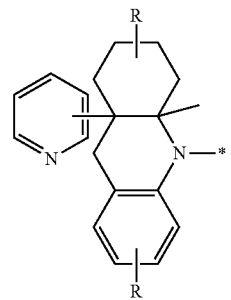

[Substituent 47]

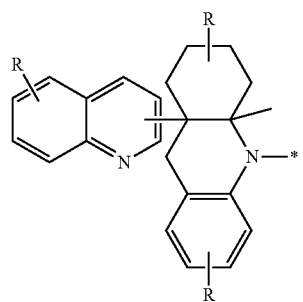

[Substituent 48]

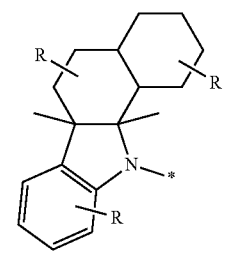

[Substituent 49]

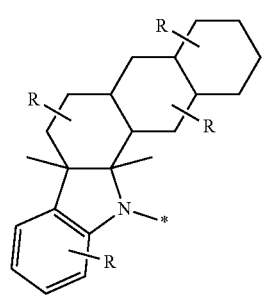

[Substituent 50]

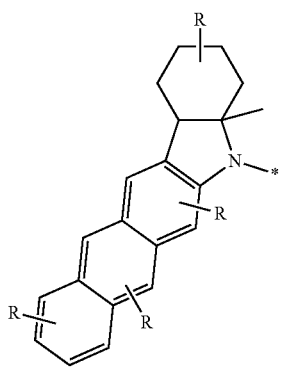

[Substituent 51]

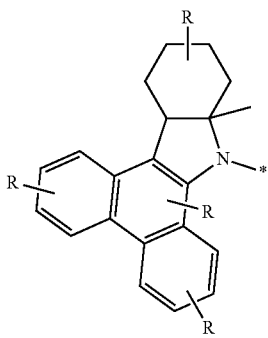

[Substituent 52]

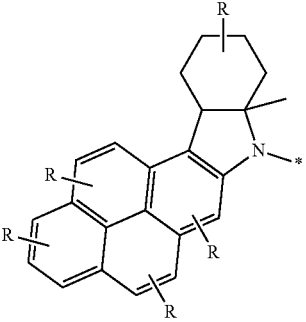

wherein R's may be the same or different and are each independently selected from among a hydrogen atom, a deuterium atom, a halogen atom, a hydroxyl, a cyano, a nitro, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms(alkylthio), a substituted or unsubstituted cycloalkyl of 3 to 60 carbon atoms, a substituted or unsubstituted aryl of 6 to 60 carbon atoms, a substituted or unsubstituted aryloxy of 6 to 60 carbon atoms, a substituted or unsubstituted arylthio of 6 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms or a (substituted or unsubstituted aryl)amino of 6 to 60 carbon atoms, and a di(substituted or unsubstituted aryl)amino of 6 to 60 carbon atoms, a substituted or unsubstituted alkylsilyl of 1 to 40 carbon atoms, a substituted or unsubstituted arylsilyl of 6 to 30 carbon atoms, a germanium, a phosphorous, and a boron, and may individually 1 to 12 substituents which may each form a fused ring with an adjacent radical.

A better understanding of the present disclosure may be obtained through the following examples which are set forth to illustrate, but are not to be construed as limiting the present disclosure.

EXAMPLES

Synthesis Example 1: Synthesis of Compound of Chemical Formula 1

Synthetic Example 1-(1): Synthesis of Intermediate 1-a

As illustrated in the following Reaction Scheme 1, Intermediate 1-a was synthesized:

<Reaction Scheme 1>

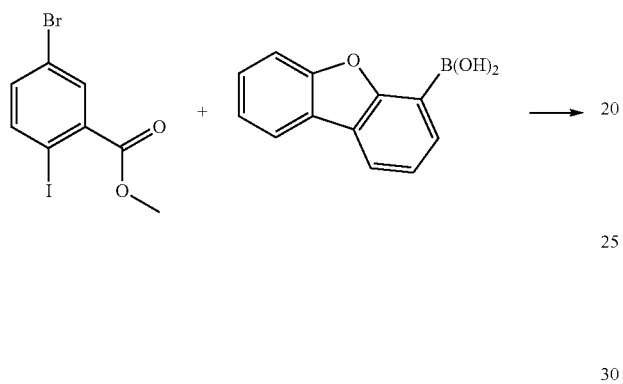

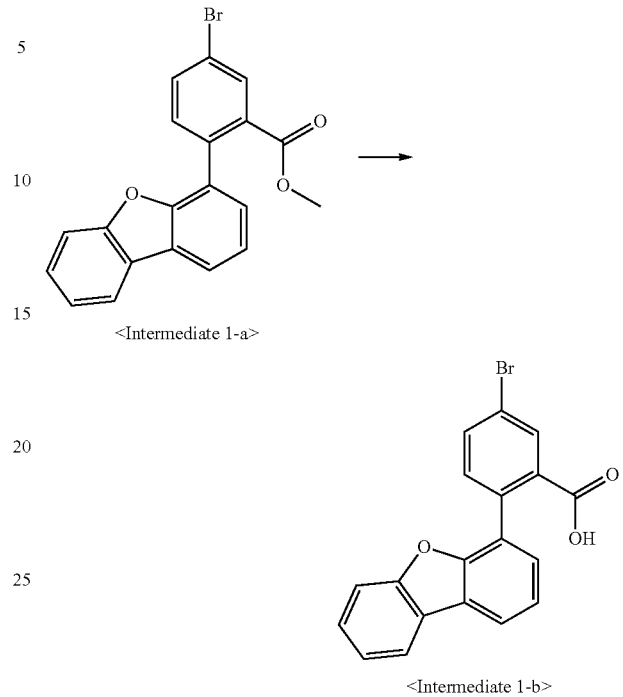

<Intermediate 1-a>

In a 500-mL round-bottom flask reactor, methyl 5-bromo-2-iodobenzoate (25.0 g, 73 mmol), 4-dibenzofuran boronic acid (18.7 g, 88 mmol), tetrakis (triphenylphosphine)palladium (1.7 g, 0.15 mmol), and potassium carbonate (20.2 g, 146.7 mmol) were stirred together with toluene (125 mL), tetrahydrofuran (125 mL), and water (50 mL) for hrs at 80° C. After completion of the reaction, the reaction mixture was cooled to room temperature and extracted with ethyl acetate. The organic layer thus formed was separated, concentrated in a vacuum, and purified by column chromatography to afford Intermediate 1-a. (75.0 g, 60.1%).

Synthesis Example 1-(2): Synthesis of Intermediate 1-b

Intermediate 1-b was synthesized as illustrated in the following Reaction Scheme 2:

In a 500-mL round-bottom flask reactor, <Intermediate 1-a> (17.0 g, 45 mmol), sodium hydroxide (2.14 g, 54 mmol) and ethanol (170 ml) were stirred together for 48 hrs under reflux. After the completion of the reaction was confirmed using thin-layer chromatography, the reaction mixture was cooled to room temperature. The chilled solution was acidified with drops of 2-N HCl, followed by stirring for 30 min. The solid thus formed was filtered and then recrystallized in dichloromethane and n-hexane to afford <Intermediate 1-b>. (14.5 g, 88.6%)

Synthesis Example 1-(3): Synthesis of Intermediate 1-c

Intermediate 1-c was synthesized as illustrated in the following Reaction Scheme 3:

<Reaction Scheme 3>

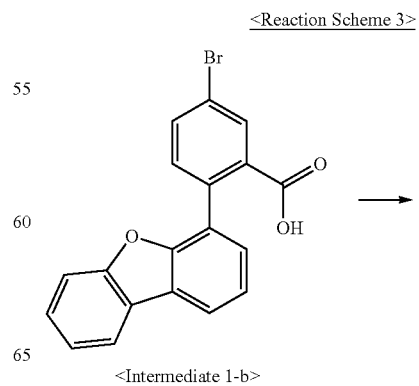

<Intermediate 1-b>

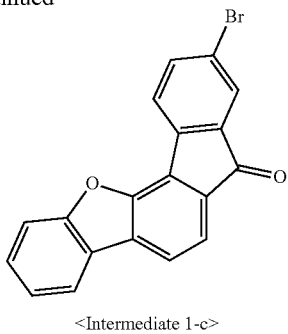

<Intermediate 1-c>

In a 250-mL round-bottom flask reactor, <Intermediate 1-b> (14.5 g, 39 mmol) and methanesulfonic acid (145 ml) were stirred together for 3 hrs at 80° C. After the completion of the reaction was confirmed using thin-layer chromatography, the reaction mixture was cooled to room temperature and dropwise added to ice water (150 ml). After stirring for 30 min, the solid thus formed was filtered and washed with water and methanol to afford <Intermediate 1-c>. (11.50 g, 83.4%)

Synthesis Example 1-(4): Synthesis of Intermediate 1-d

Intermediate 1-d was synthesized as illustrated in the following Reaction Scheme 4:

<Reaction Scheme 4>

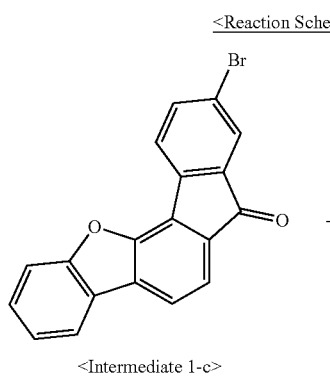

<Intermediate 1-c>

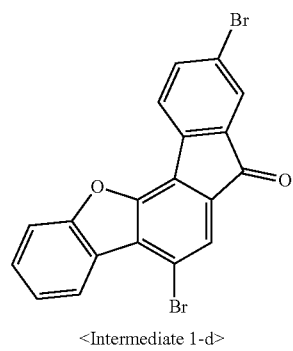

<Intermediate 1-d>

In a 1-L round-bottom flask reactor, <Intermediate 1-c> (11.5 g, 33 mmol> and dichloromethane (300 ml) were stirred together at room temperature. A dilution of bromine (3.4 ml, 66 mmol) in dichloromethane (50 ml) was dropwise added, followed by stirring at room temperature for 8 hrs. After completion of the reaction, the reaction mixture was stirred together with acetone (100 ml). The solid thus formed was filtered and washed with acetone. Recrystallization in monochlorobenzene afforded <Intermediate 1-d>. (11.0 g, 78%)

Synthesis Example 1-(5): Synthesis of Intermediate 1-e

Intermediate 1-e was synthesized as illustrated in the following Reaction Scheme 5:

<Reaction Scheme 5>

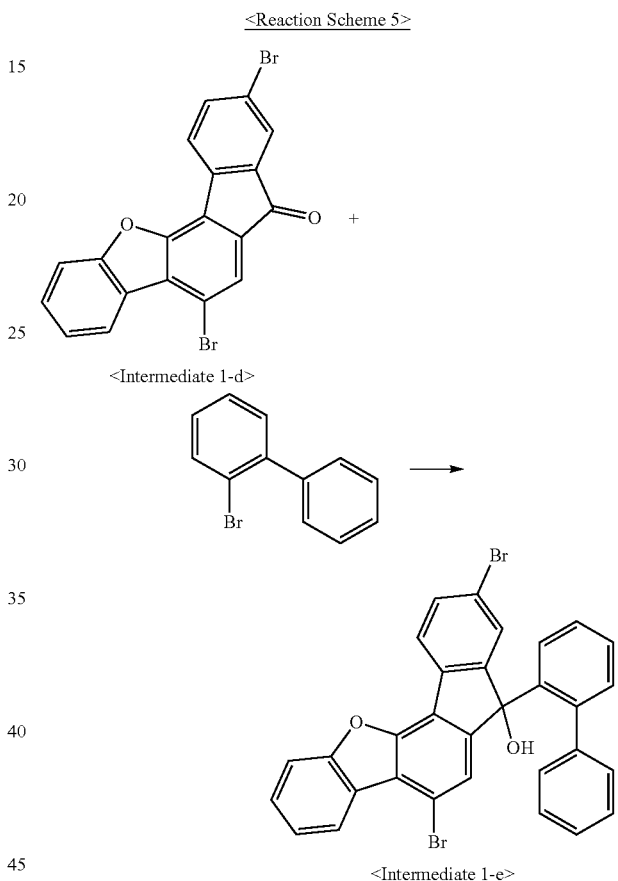

<Intermediate 1-e>

In a 250-ml round-bottom flask reactor, 2-bromobiphenyl (8.4 g, 0.036 mol) and tetrahydrofuran (110 ml) were frozen at −78° C. in a nitrogen atmosphere. At the same temperature, n-butyl lithium (19.3 ml, 0.031 mol) was dropwise added to the reaction solution, which was then stirred for 2 hrs. Thereafter, <Intermediate 1-d> (11.0 g, 0.026 mol) was added little by little to the reaction solution and stirred at room temperature. When the reaction mixture started to change color, the reaction was monitored via TLC. After the reaction was stopped with H₂O (50 ml), extraction was conducted with ethyl acetate and water. The organic layer was separated, concentrated in a vacuum, and recrystallized in acetonirile to afford <Intermediate 1-e> as a solid. (12.2 g, 81.5%)

Synthesis Example 1-(6): Synthesis of Intermediate 1-f

Intermediate 1-f was synthesized as illustrated in the following Reaction Scheme 6:

Reaction Scheme 6

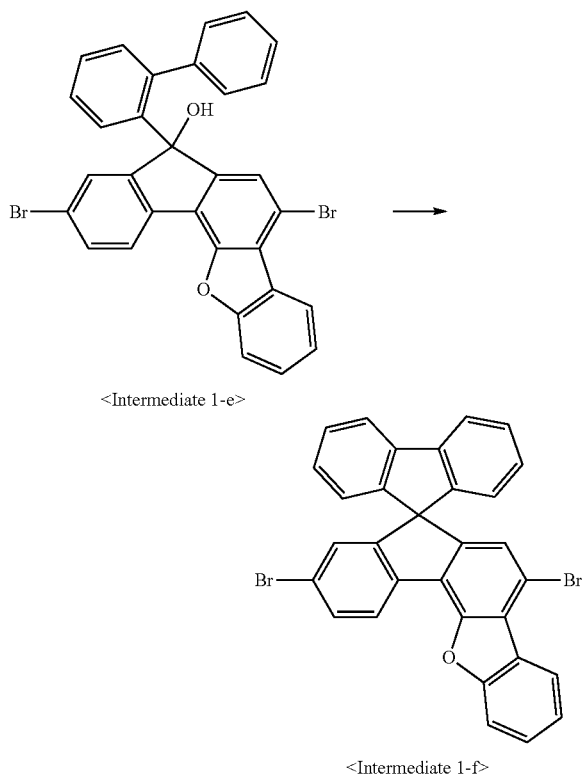

<Intermediate 1-e>

<Intermediate 1-f>

In a 250-ml round-bottom flask reactor, a mixture of <Intermediate 1-e> (12.0 g, 0.021 mol), acetic acid (120 ml), and sulfuric acid (2 ml) was stirred for 5 hrs under reflux. When a precipitate was formed, the completion of the reaction was monitored using thin-layer chromatography. The reaction mixture was then cooled to room temperature and filtered. The filtrate was washed with $H_2O$ and methanol and dissolved in monochlorobenzene. Following silica gel chromatography, the fraction was concentrated and cooled to room temperature to give <Intermediate 1-f>. (10.7 g, 90%)>

Synthesis Example 1-(7): Synthesis of Compound of Chemical Formula 1

The compound of Chemical Formula 1 was synthesized as illustrated in the following Reaction Scheme 7:

Reaction Scheme 7

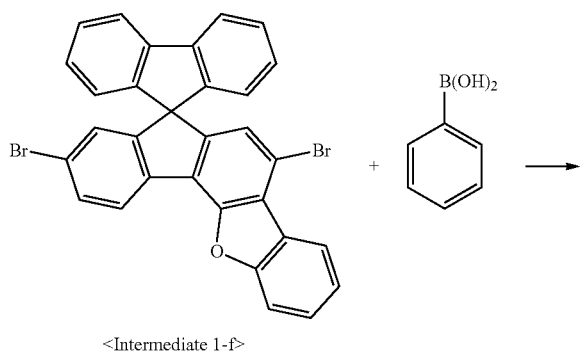

<Intermediate 1-f>

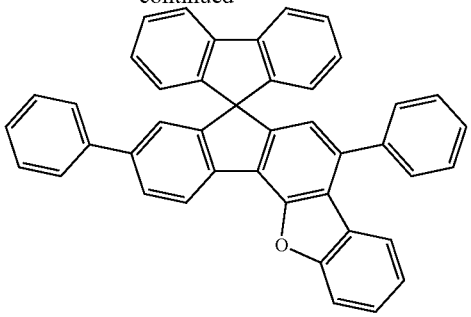

<Chemical Formula 1>

In a 500-ml round bottom flask reactor, <Intermediate 1-f> (10.0 g, 0.017 mol), phenyl boronic acid (4.8 g, 0.039 mol), tetrakis triphenyl phosphine palladium (0.8 g, 0.001 mol), potassium carbonate (9.56 g, 0.069 mol), toluene (120 ml), ethanol (60 ml), and water (45 ml) were stirred together for 2 hrs under reflux. After completion of the reaction, the reaction mixture was cooled to room temperature and concentrated. The concentrate was dissolved in dichloromethane and recrystallized in methanol, followed by hot filtration with toluene. After isolation and purification by column chromatography, recrystallization in dichloromethane and acetone afforded the compound of Chemical Formula 1. (9.9 g, 99%)

MS (MALDI-TOF): m/z 558.2 [$M^+$]

Synthesis Example 2: Synthesis of Compound of Chemical Formula 21

Synthetic Example 2-(1): Synthesis of Intermediate 2-a

Intermediate 2-a was synthesized as illustrated in the following Reaction Scheme 8:

Reaction Scheme 8

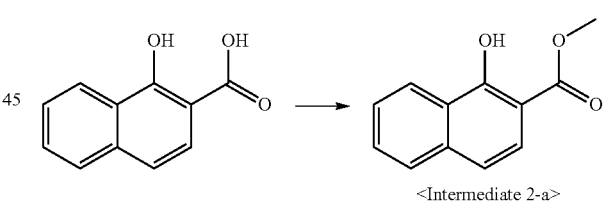

<Intermediate 2-a>

In a 2-L round-bottom flask reactor, 1-hydroxy 2-naphthalic acid (50 g, 266 mmol), methanol (1000 ml), and sulfuric acid (100 ml) were stirred together for 100 hrs under reflux. The completion of the reaction was confirmed by TLC before the reaction mixture was cooled to room temperature. The mixture was concentrated in a vacuum and extracted with dichloromethane and water. The organic layer was isolated, dried over magnesium sulfate, and filtered. The filtrate was concentrated at a reduced pressure and crystallized in an excess of heptane to afford <Intermediate 2-a> (39 g, 72.6%).

Synthetic Example 2-(2): Synthesis of Intermediate 2-b

Intermediate 2-b was synthesized as illustrated in the following Reaction Scheme 9:

Reaction Scheme 9

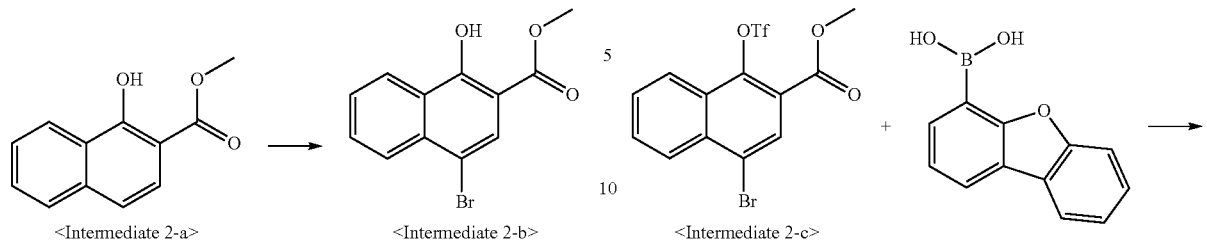

In a 1-L round-bottom flask reactor, <Intermediate 2-a> (39.0 g, 193 mmol) was stirred together with acetic acid (390 ml) at room temperature. A dilution of acetic acid (80 ml) in bromine (11.8 ml, 231 mmol) was added dropwise thereto. The resulting reaction solution was stirred for 5 hrs at room temperature. After completion of the reaction, the precipitates thus formed were filtered and slurried in heptane to afford <Intermediate 2-b> (50 g, 90%).

Synthetic Example 2-(3): Synthesis of Intermediate 2-c

Intermediate 2-c was synthesized as illustrated in the following Reaction Scheme 10:

Reaction Scheme 10

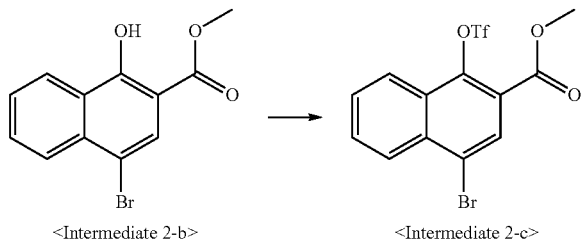

In a 2-L round-bottom flask reactor, <Intermediate 2-b> (50 g, 178 mmol) was stirred together with dichloromethane. Under a nitrogen atmosphere, pyridine (28.1 g, 356 mmol) was added and stirred at room temperature for 20 min. The resulting solution was cooled to 0° C. and then added with drops of trifluoromethanesulfonic anhydride (65.24 g, 231 mmol) under a nitrogen atmosphere. After 3 hrs of stirring, the completion of the reaction was confirmed by TLC. Water (20 ml) was added, and the mixture was stirred for 10 min. The reaction mixture was concentrated in a vacuum, followed by purification through column chromatography to afford <Intermediate 2-c> (45 g, 61%).

Synthetic Example 2-(4): Synthesis of Intermediate 2-d

Intermediate 2-d was synthesized as illustrated in the following Reaction Scheme 11:

Reaction Scheme 11

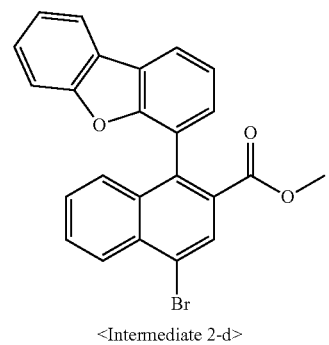

<Intermediate 2-d>

In a 1-L round-bottom flask reactor, a mixture of <Intermediate 2-c> (45.0 g, 0.109 mol), 4-dibenzofuran boronic acid (25.4 g, 0.120 mol), tetrakis (triphenylphosphine)palladium (2.5 g, 0.22 mmol), and potassium carbonate (30.1 g, 0.218 mol) was stirred together with toluene (300 mL), ethanol (130 mL) and water (90 mL) at 80° C. for 5 hrs. After completion of the reaction, the reaction mixture was cooled to room temperature and extracted with ethyl acetate. The organic layer was isolated and concentrated in a vacuum. Purification through column chromatography afforded Intermediate 2-d. (22.0 g, 46.1%)

Synthetic Example 2-(5): Synthesis of Intermediate 2-e

Intermediate 2-e was synthesized as illustrated in the following Reaction Scheme 12:

Reaction Scheme 12

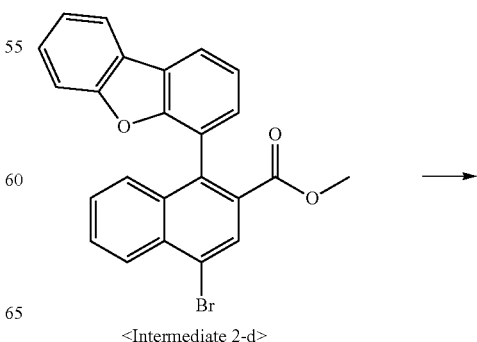

<Intermediate 2-d>

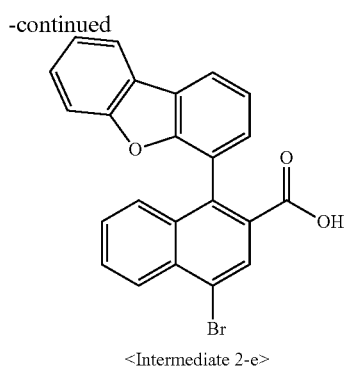

<Intermediate 2-e>

In a 1-L round-bottom flask reactor, <Intermediate 2-d> (22.0 g, 0.051 mol) was stirred together with sodium hydroxide (2.65 g, 0.066 mol) for 48 hrs under reflux. After completion of the reaction, the reaction mixture was cooled to room temperature. The chilled solution was acidified with drops of 2-N HCl, followed by stirring for 30 min. The solid thus formed was filtered and recrystallized in dichloromethane and n-hexane to afford Intermediate 2-e. (17.6 g, 82.7%)

Synthetic Example 2-(6): Synthesis of Intermediate 2-f

Intermediate 2-f was synthesized as illustrated in the following Reaction Scheme 13:

<Reaction Scheme 13>

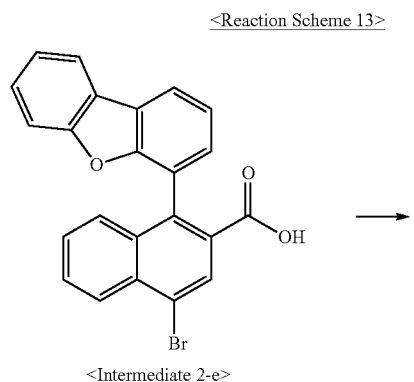

<Intermediate 2-e>

In a 500-mL round-bottom flask reactor, <Intermediate 2-e> (17.6 g, 0.042 mol) and methanesulfonic acid (170 ml) were stirred together for 3 hrs at 80° C. After the completion of the reaction was confirmed using thin-layer chromatography, the reaction mixture was cooled to room temperature and dropwise added to ice water (150 ml). After stirring for 30 min, the precipitates thus formed were filtered and washed with water and methanol. They were dissolved in monochlorobenzene and filtered through a silica gel pad. The filtrate was concentrated by heating and recrystallized in acetone to afford Intermediate 2-f. (12 g, 71%)

Synthetic Example 2-(7): Synthesis of Intermediate 2-g

Intermediate 2-g was synthesized as illustrated in the following Reaction Scheme 14:

<Reaction Scheme 14>

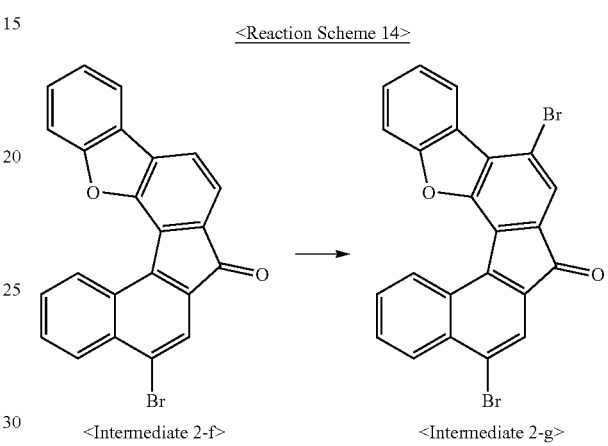

<Intermediate 2-f>    <Intermediate 2-g>

In a 1-L round-bottom flask reactor, Intermediate 2-f (12.0 g, 0.030 mol) and dichloromethane (360 ml) were stirred together at room temperature. A dilution of bromine (3.1 ml, 0.06 mol) in dichloromethane (40 ml) was dropwise added, followed by stirring at room temperature for 12 hrs. After completion of the reaction, methanol (100 ml) was added to induce the formation of precipitates. They were then filtered and washed with methanol. Recrystallization in 1,2-dichlorobenzene and acetone afforded Intermediate 2-g (10.3 g, 71.7%).

Synthetic Example 2-(8): Synthesis of Intermediate 2-h

Intermediate 2-h was synthesized as illustrated in the following Reaction Scheme 15:

<Reaction Scheme 15>

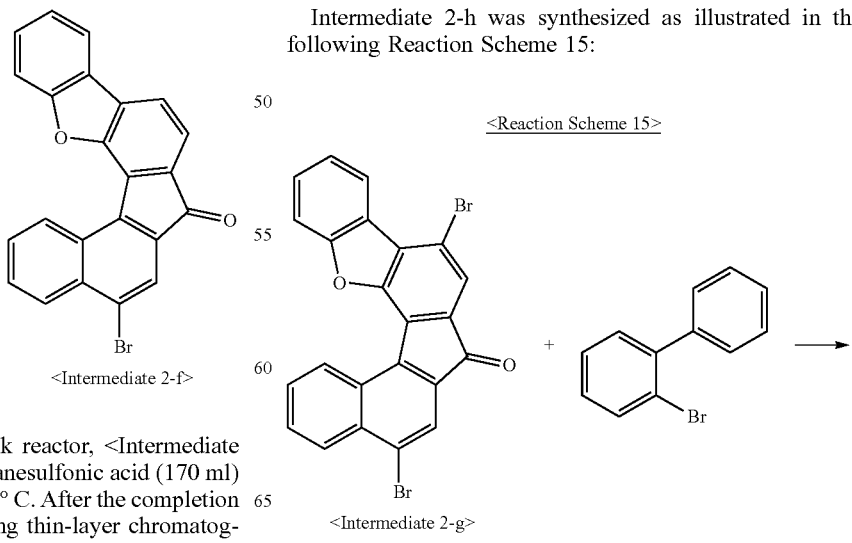

<Intermediate 2-g>

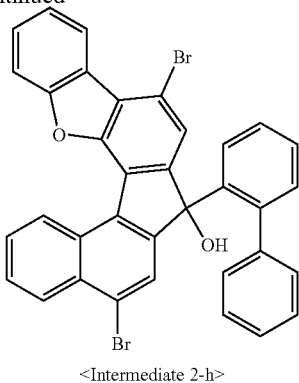

<Intermediate 2-h>

The same procedure was conducted as in Synthesis Example 1-(5), with the exception that <Intermediate 2-g> was used, instead of <Intermediate 1-d>, to produce <Intermediate 2-h>. (10.0 g, 73.4%)

Synthetic Example 2-(9): Synthesis of Intermediate 2-i

Intermediate 2-i was synthesized as illustrated in the following Reaction Scheme 16:

<Reaction Scheme 16>

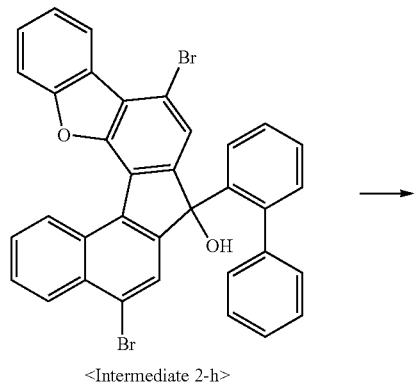

The same procedure was conducted as in Synthesis Example 1-(6), with the exception that <Intermediate 2-h> was used, instead of <Intermediate 1-e>, to produce <Intermediate 2-i>. (6.3 g, 64.8%)

Synthetic Example 2-(10): Synthesis of Compound of Chemical Formula 21

The compound of Chemical Formula 21 was synthesized as illustrated in the following Reaction Scheme 17:

<Reaction Scheme 17>

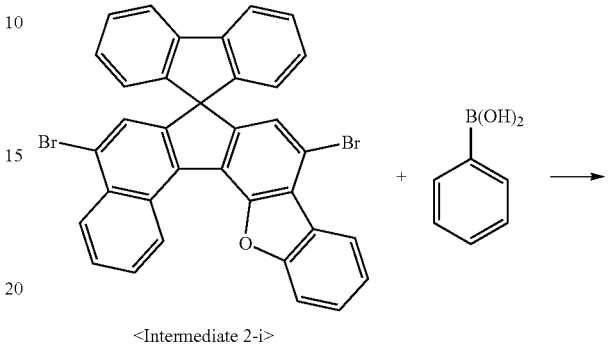

<Intermediate 2-i>

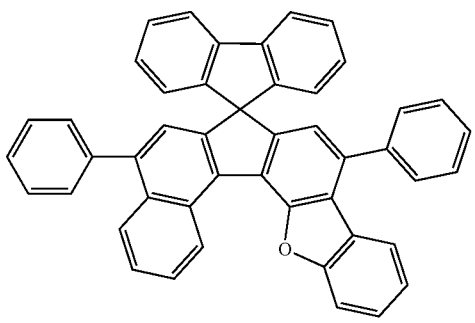

<Chemical Formula 21>

The same procedure was conducted as in Synthesis Example 1-(7), with the exception that <Intermediate 2-i> was used, instead of <Intermediate 1-f>, to produce the compound of <Chemical Formula 21>. (6.0 g, 98%)

MS (MALDI-TOF): m/z 608.21 [M$^+$]

Synthesis Example 3: Synthesis of Compound of Chemical Formula 34

Synthetic Example 3-(1): Synthesis of Intermediate 3-a

Intermediate 3-a was synthesized as illustrated in the following Reaction Scheme 18:

<Reaction Scheme 18>

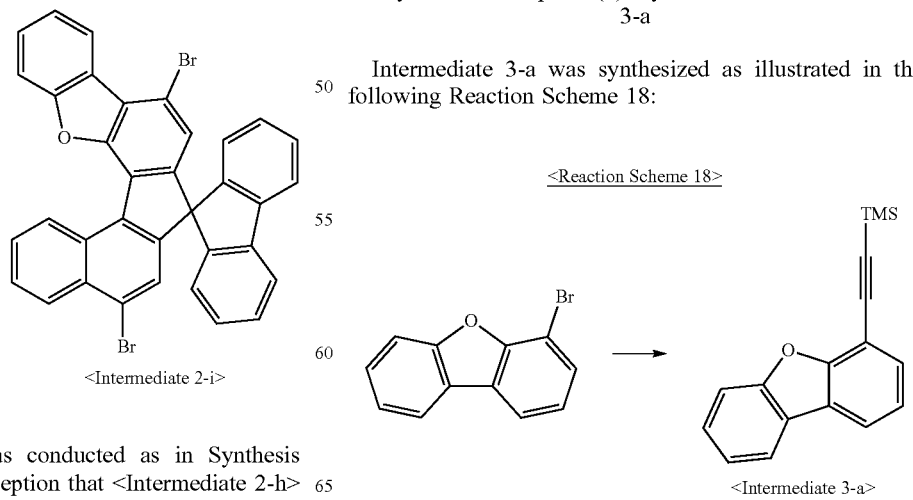

<Intermediate 3-a>

In a 2-L round bottom flask, 4-bromodibenzofuran (100.0 g, 0.405 mol), ethynyl trimethylsilane (47.7 g, 0.486 mol), [1,1'-bis(diphenylphosphino)ferrocene]dichloropalladium (9.92 g, 0.012 mol), copper iodide (2.31 g, 0.012 mol), triphenylphosphine (10.6 g, 0.040 mol), and triethylamine (700 ml) were stirred for 5 hrs under reflux in a nitrogen atmosphere. After completion of the reaction, the reaction mixture was cooled to room temperature and added with heptane (500 ml) to terminate the reaction. Filtration was conducted through a silica gel pad topped with celite. The filtrate was concentrated in a vacuum to afford <Intermediate 3-a> (130 g, 84%).

Synthetic Example 3-(2): Synthesis of Intermediate 3-b

Intermediate 3-b was synthesized as illustrated in the following Reaction Scheme 19:

<Reaction Scheme 19>

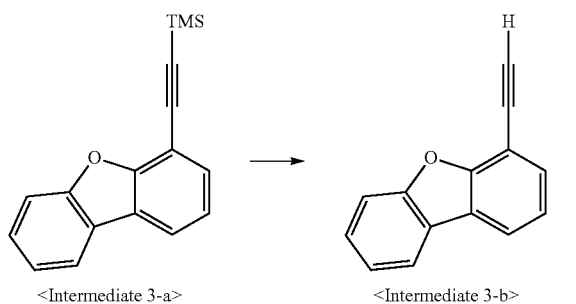

<Intermediate 3-a>        <Intermediate 3-b>

In a 2-L round-bottom flask reactor, <Intermediate 3-a> (130 g, 0.492 mol), potassium carbonate (101.9 g, 0.738 mol), methanol (650 ml), and tetrahydrofuran (650 ml) were stirred together for 2 hrs at room temperature. After completion of the reaction, heptane (500 ml) was added to terminate the reaction. The reaction mixture was filtered and the filtrate was extracted with ethyl acetate and water. The organic layer thus formed was isolated and dried over magnesium sulfate. Filtration and vacuum concentration afforded <Intermediate 3-b> as an oil (82 g, 84%).

Synthetic Example 3-(3): Synthesis of Intermediate 3-c

Intermediate 3-c was synthesized as illustrated in the following Reaction Scheme 20:

<Reaction Scheme 20>

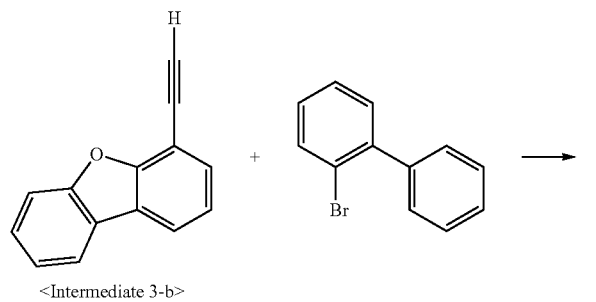

<Intermediate 3-b>

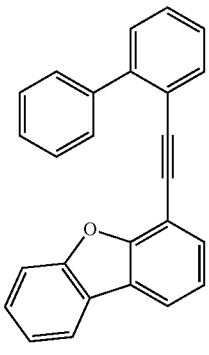

<Intermediate 3-c>

In a 2-L round-bottom flask reactor, 2-bromobiphenyl (66.0 g, 0.283 mol), <Intermediate 3-b> (65.3 g, 0.340 mol), [1,1'-bis(diphenylphosphino)ferrocene]dichloropalladium (6.94 g, 0.008 mol), copper iodide (1.62 g, 0.008 mol), triphenylphosphine (7.4 g, 0.028 mol), and triethylamine (500 ml) were stirred for 5 hrs under reflux in a nitrogen atmosphere. After completion of the reaction, the reaction mixture was cooled to room temperature and added with heptane (500 ml) to terminate the reaction. Filtration was conducted through a silica gel pad topped with celite. The filtrate was concentrated in a vacuum to afford <Intermediate 3-c> (80 g, 82%).

Synthetic Example 3-(4): Synthesis of Intermediate 3-d

Intermediate 3-d was synthesized as illustrated in the following Reaction Scheme 21:

<Reaction Scheme 21>

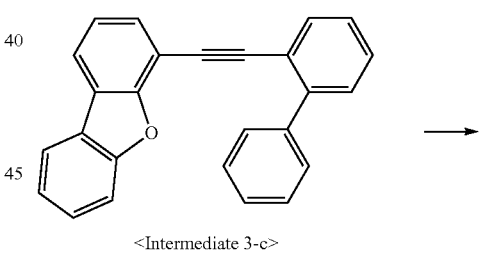

<Intermediate 3-c>

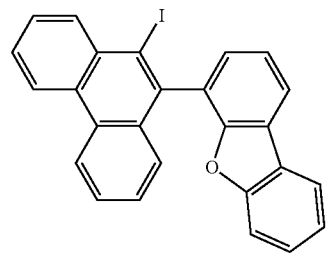

<Intermediate 3-d>

In a 2-L round-bottom flask reactor, a solution of <Intermediate 3-c> (80.0 g, 0.232 mol) in dichloromethane (960 ml) was cooled to −78° C. under a nitrogen atmosphere. Iodine monochloride (278.4 ml, 0.279 mol) was dropwise added to the chilled solution, which was then stirred at room temperature for 12 hrs. After completion of the reaction, the reaction mixture was stirred together with an aqueous saturated sodium thiosulfate solution. Following extraction with dichloromethane and water, the organic layer was isolated, concentrated in a vacuum, and washed with methanol to afford <Intermediate 3-d> as a crystal (67 g, 61.3%).

Synthetic Example 3-(5): Synthesis of Intermediate 3-e

Intermediate 3-e was synthesized as illustrated in the following Reaction Scheme 22:

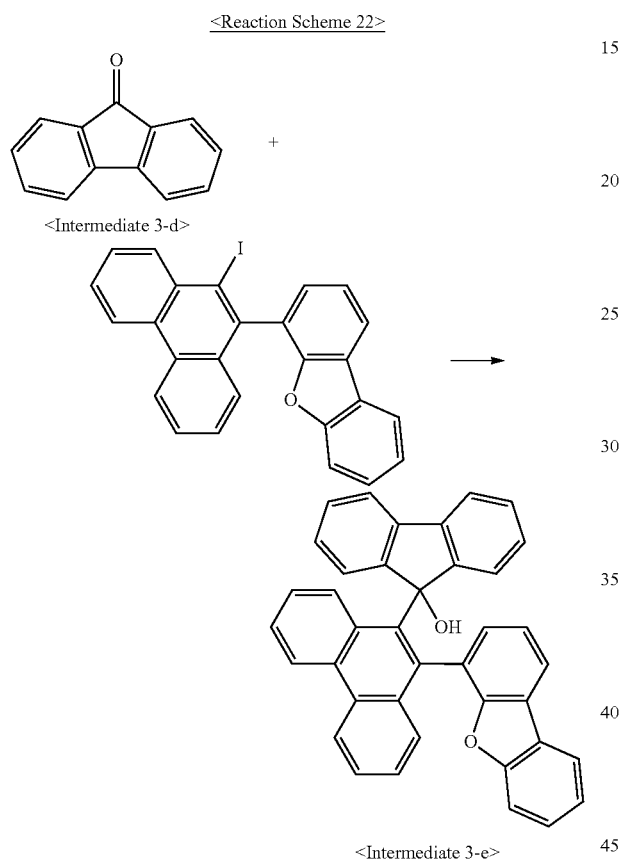

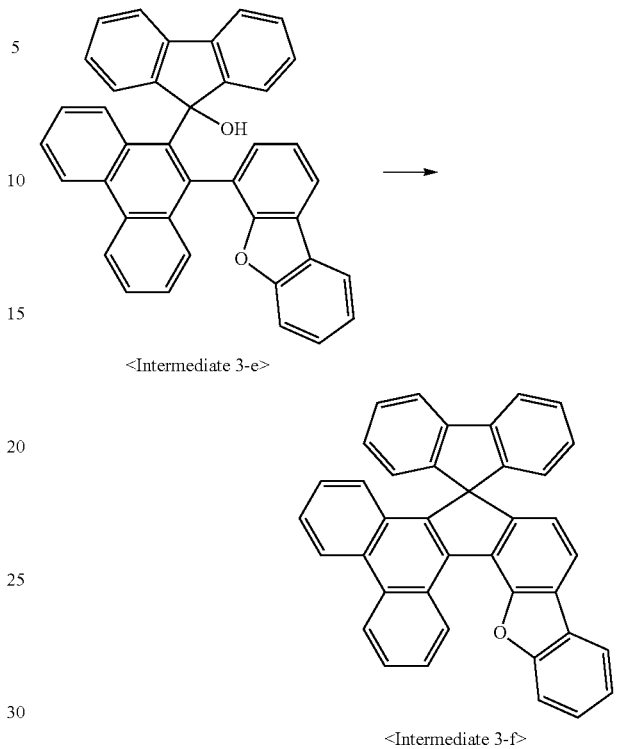

In a 500-mL round-bottom flask reactor, a solution of <Intermediate 3-d> (54.8 g, 0.117 mol) in tetrahydrofuran (150 ml) was cooled to −78° C. under a nitrogen atmosphere. At the same temperature, 1.6 M n-butyl lithium (62.4 ml, 0.1 mol) was dropwise added to the chilled solution and stirred for 1 hr. Then, a solution of 9-fluorenone (15.0 g, 0.083 mol) in tetrahydrofuran (50 ml) was dropwise added before stirring at room temperature for 8 hrs. After completion of the reaction, extraction was performed with ethyl acetate and water. The organic layer thus formed was isolated and dried over magnesium sulfate. Vacuum concentration subsequent to filtration afforded <Intermediate 3-e> as an oil (33.2 g, 76%).

Synthetic Example 3-(6): Synthesis of Intermediate 3-f

Intermediate 3-f was synthesized as illustrated in the following Reaction Scheme 23:

In a 1-L round-bottom flask reactor, <Intermediate 3-e> (33.3 g, 0.063 mol), acetic acid (330 ml), and sulfuric acid (3 ml) were stirred together for 3 hrs under reflux. After the completion of the reaction was confirmed using thin-layer chromatography, the reaction mixture was cooled to room temperature. The precipitates thus formed were filtered and washed with H₂O and methanol to afford <Intermediate 3-f> (28.6 g, 88%).

Synthetic Example 3-(7): Synthesis of Intermediate 3-g

Intermediate 3-g was synthesized as illustrated in the following Reaction Scheme 24:

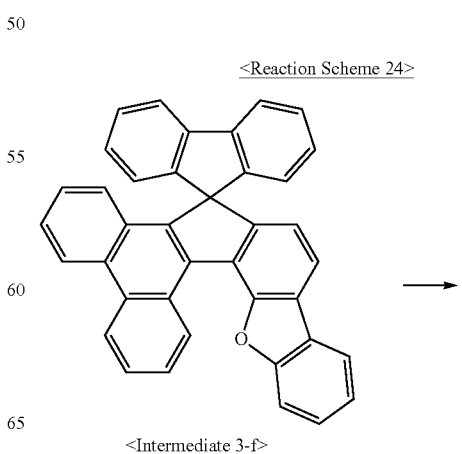

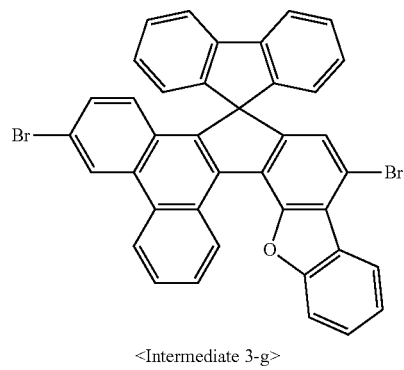

<Intermediate 3-g>

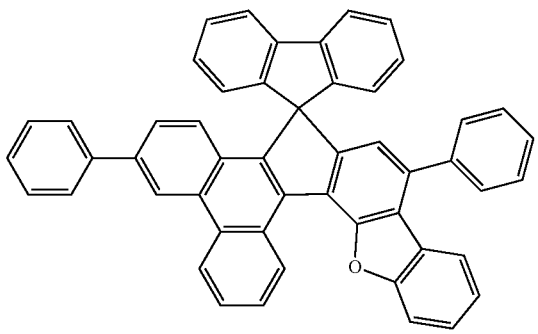

<Chemical Formula 34>

In a 1-L round-bottom flask reactor, a solution of <Intermediate 3-f> (20.0 g, 0.039 mol) in dichloromethane (200 ml) was added with drops of a dilution of bromine (6 ml, 0.118 mol) in dichloromethane (40 ml) while stirring. After completion of the reaction for 12 hrs of stirring at room temperature, the addition of methanol (100 ml) produced precipitates which were then washed with methanol. Recrystallization in 1,2-dichlorobenzene and acetone afforded <Intermediate 3-g> (16 g, 60%).

Synthetic Example 3-(8): Synthesis of Compound of Chemical Formula 34

The compound of Chemical Formula 34 was synthesized as illustrated in the following Reaction Scheme 25:

<Reaction Scheme 25>

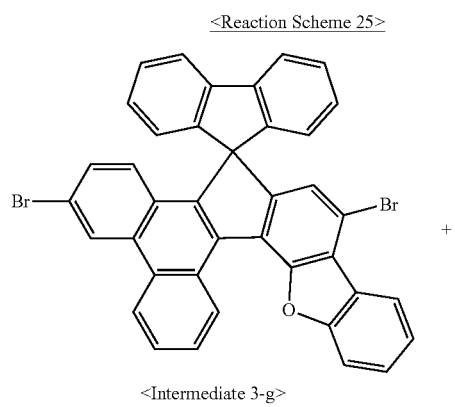

<Intermediate 3-g>

+

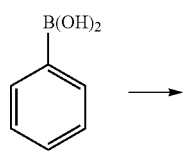

The same procedure was conducted as in Synthesis Example 1-(7), with the exception that <Intermediate 3-g> was used, instead of <Intermediate 1-f>, to produce the compound of <Chemical Formula 34>. (5.2 g, 98.6%)

MS (MALDI-TOF): m/z 658.23 [M$^+$]

Synthesis Example 4: Synthesis of Compound of Chemical Formula 52

Synthetic Example 4-(1): Synthesis of Intermediate 4-a

Intermediate 4-a was synthesized as illustrated in the following Reaction Scheme 26:

<Reaction Scheme 26>

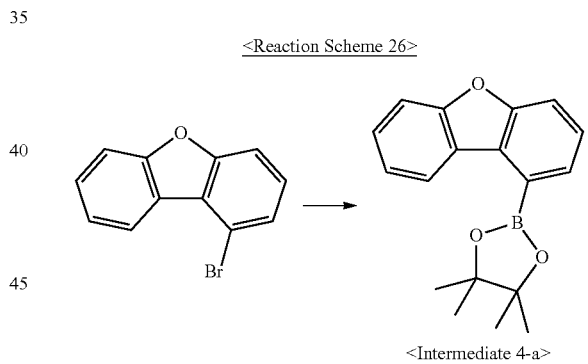

<Intermediate 4-a>

In a 500-mL round-bottom flask reactor, 1-bromodibenzofuran (20.0 g, 0.081 mmol), bis(pinacolato)diboron (26.7 g, 0.105 mol), [1,1'-bis(diphenylphosphino)ferrocene]dichloropalladium (1.3 g, 0.002 mol), potassium acetate (19.9 g, 0.202 mol), and 1,4-dioxane (200 ml) were stirred together for 10 hrs under reflux. After completion of the reaction, filtration was performed through a celite pad. The filtrate was concentrated in a vacuum, purified by column chromatography, and recrystallized in dichloromethane and heptane to afford Intermediate 4-a (17.0 g, 70%).

Synthetic Example 4-(2): Synthesis of Intermediate 4-b

Intermediate 4-b was synthesized as illustrated in the following Reaction Scheme 27:

Reaction Scheme 27

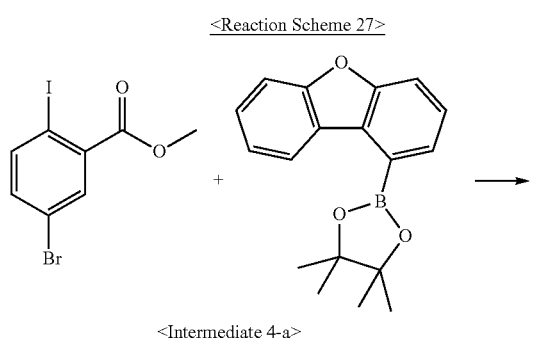

<Intermediate 4-a>

[Structure: Intermediate 4-b]

The same procedure was conducted as in Synthesis Example 1-(1), with the exception that <Intermediate 4-a> was used, instead of 4-dibenzofuranboronic acid, to produce <Intermediate 4-b>. (13.1 g, 68.9%)

Synthetic Example 4-(3): Synthesis of Intermediate 4-c

Intermediate 4-c was synthesized as illustrated in the following Reaction Scheme 28:

Reaction Scheme 28

[Structure: Intermediate 4-b]

→

The same procedure was conducted as in Synthesis Example 1-(2), with the exception that <Intermediate 4-b> was used, instead of <Intermediate 1-a>, to produce <Intermediate 4-c>. (11.0 g, 87%)

Synthetic Example 4-(4): Synthesis of Intermediate 4-d

Intermediate 4-d was synthesized as illustrated in the following Reaction Scheme 29:

Reaction Scheme 29

[Structure: Intermediate 4-c]

→

[Structure: Intermediate 4-d]

The same procedure was conducted as in Synthesis Example 1-(3), with the exception that <Intermediate 4-c> was used, instead of <Intermediate 1-b>, to produce <Intermediate 4-d> (11.0 g, 87%)

Synthetic Example 4-(5): Synthesis of Intermediate 4-e

Intermediate 4-e was synthesized as illustrated in the following Reaction Scheme 30:

Reaction Scheme 30

[Structure: Intermediate 4-c]

[Structure: Intermediate 4-d]

→

-continued

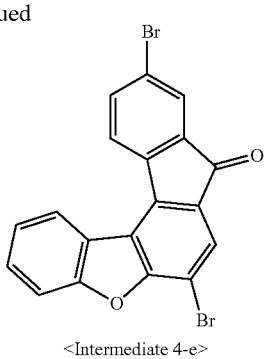
<Intermediate 4-e>

The same procedure was conducted as in Synthesis Example 1-(4), with the exception that <Intermediate 4-d> was used, instead of <Intermediate 1-c>, to produce <Intermediate 4-e> (6.7 g, 60.7%)

Synthetic Example 4-(6): Synthesis of Intermediate 4-f

Intermediate 4-f was synthesized as illustrated in the following Reaction Scheme 31:

<Reaction Scheme 31>

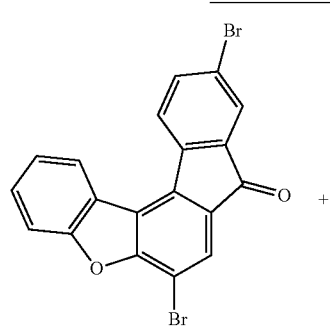
<Intermediate 4-e>

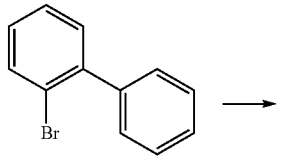

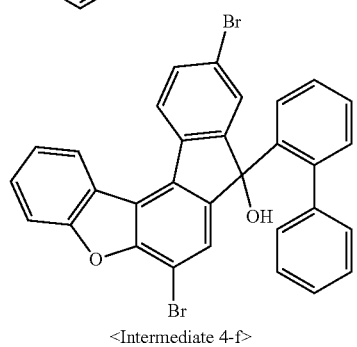
<Intermediate 4-f>

The same procedure was conducted as in Synthesis Example 1-(5), with the exception that <Intermediate 4-e> was used, instead of <Intermediate 1-d>, to produce <Intermediate 4-f> (5.2 g, 55%)

Synthetic Example 4-(7): Synthesis of Intermediate 4-g

Intermediate 4-g was synthesized as illustrated in the following Reaction Scheme 32:

<Reaction Scheme 32>

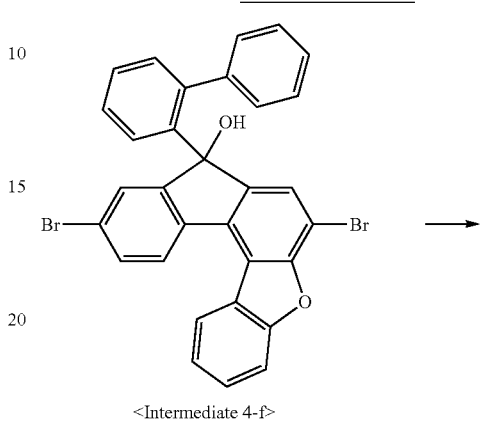
<Intermediate 4-f>

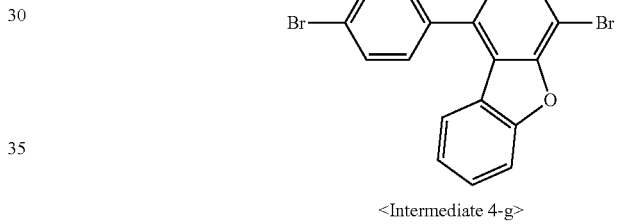
<Intermediate 4-g>

The same procedure was conducted as in Synthesis Example 1-(6), with the exception that <Intermediate 4-f> was used, instead of <Intermediate 1-e>, to produce <Intermediate 4-g>. (4.3 g, 85.3%)

Synthetic Example 4-(8): Synthesis of Compound of Chemical Formula 52

Chemical Formula 52 was synthesized as illustrated in the following Reaction Scheme 33:

<Reaction Scheme 33>

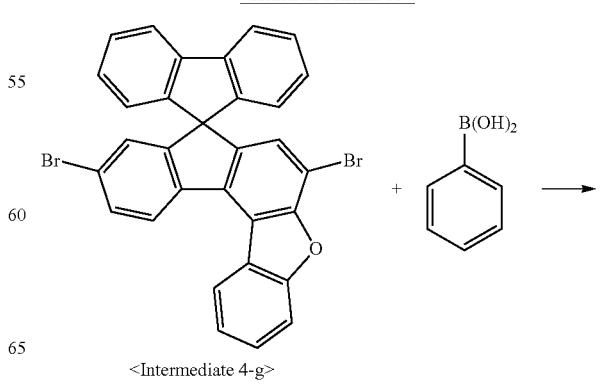
<Intermediate 4-g>

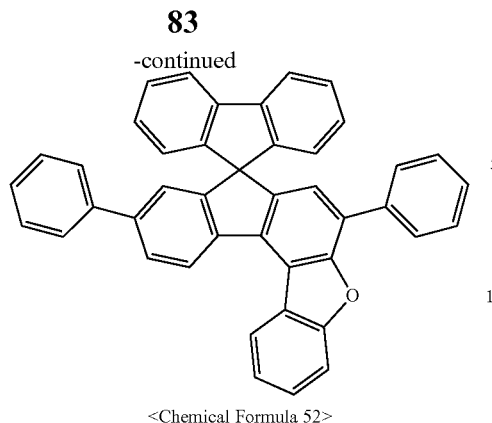

<Chemical Formula 52>

The same procedure was conducted as in Synthesis Example 1-(7), with the exception that <Intermediate 4-g> was used, instead of <Intermediate 1-f>, to produce <Chemical Formula 52>. (2.5 g, 34%)

MS (MALDI-TOF): m/z 558.2 [M$^+$]

Synthesis Example 5: Synthesis of Compound of Chemical Formula 83

Synthetic Example 5-(1): Synthesis of Intermediate 5-a

Intermediate 5-a was synthesized as illustrated in the following Reaction Scheme 34:

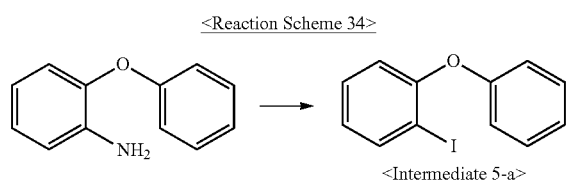 [SMILES: Nc1ccccc1Oc1ccccc1 ; Ic1ccccc1Oc1ccccc1]

<Reaction Scheme 34>

<Intermediate 5-a>

In a 1-L round-bottom flask reactor, a mixture of 2-phenoxyaniline (25.0 g, 0.135 mol), HCl (30 ml), and water (150 ml) was cooled to 0° C. and stirred for 1 hr. At the same temperature, an aqueous solution (75 ml) of sodium nitrite (11.2 g, 0.162 mol) was added and then stirred for 1 hr. An aqueous solution (75 ml) of potassium iodide (44.8 g, 0.270 mol) was dropwise added, taking care not to increase the temperature of the reaction solution above 5° C. Stirring was continued for 5 hrs at room temperature, and after completion of the reaction, the reaction mixture was washed with an aqueous sodium thiosulfate solution and extracted with ethyl acetate and water. The organic layer was separated and concentrated in a vacuum. Purification through column chromatography gave Intermediate 5-a (22.6 g, 56.5%).

Synthetic Example 5-(2): Synthesis of Intermediate 5-b

Intermediate 5-b was synthesized as illustrated in the following Reaction Scheme 35:

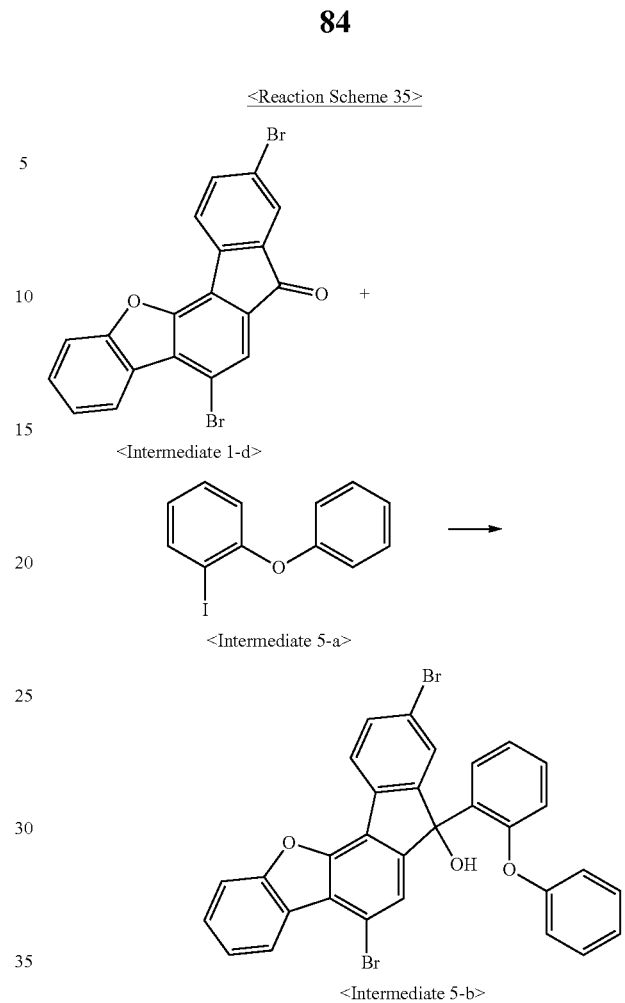

<Reaction Scheme 35>

<Intermediate 1-d>

<Intermediate 5-a>

<Intermediate 5-b>

The same procedure was conducted as in Synthesis Example 1-(5), with the exception that Intermediate 5-a was used, instead of 2-bromobiphenyl, to synthesize Intermediate 5-b (19.6 g, 70.4%).

Synthetic Example 5-(3): Synthesis of Intermediate 5-c

Intermediate 5-c was synthesized as illustrated in the following Reaction Scheme 36:

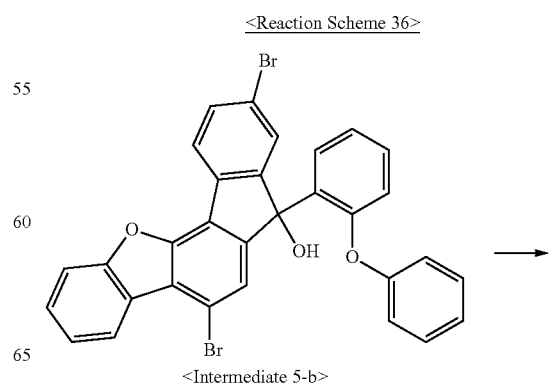

<Reaction Scheme 36>

<Intermediate 5-b>

-continued

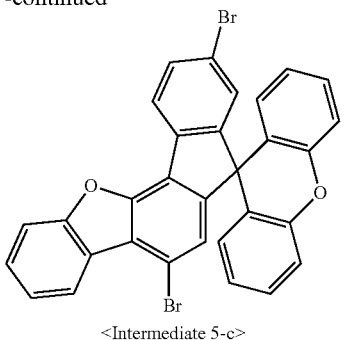
<Intermediate 5-c>

The same procedure was conducted as in Synthesis Example 1-(6), with the exception that Intermediate 5-b was used instead of Intermediate 1-e, to synthesize Intermediate 5-c (14.2 g, 74.7%).

Synthetic Example 5-(4): Synthesis of Compound of Chemical Formula 83

The compound of Chemical Formula 83 was synthesized as illustrated in the following Reaction Scheme 37:

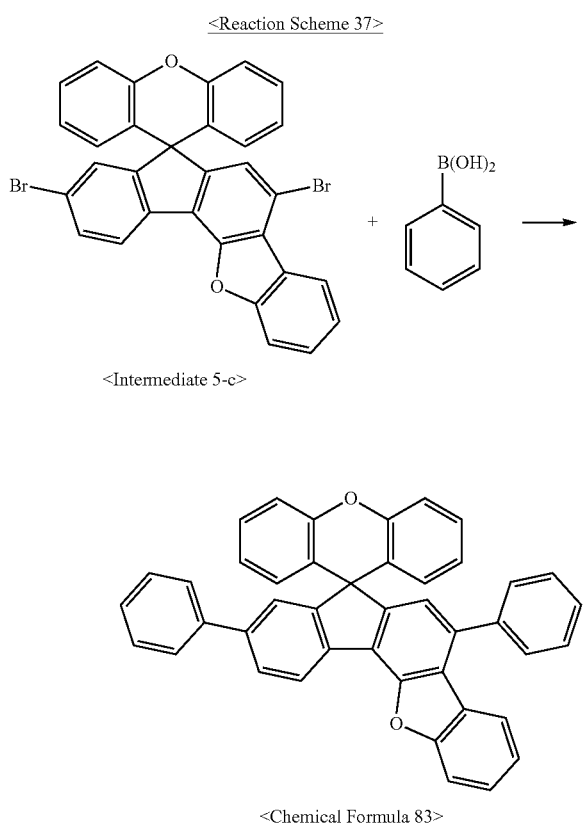 [SMILES: Brc1ccc2c(c1)C1(c3ccccc3Oc3ccccc31)c1cc(Br)c3c(oc4ccccc43)c1-2 ; OB(O)c1ccccc1 ; c1ccc(-c2ccc3c(c2)C2(c4ccccc4Oc4ccccc42)c2cc(-c4ccccc4)c4c(oc5ccccc54)c2-3)cc1]
<Chemical Formula 83>

The same procedure was conducted as in Synthesis Example 1-(7), with the exception that <Intermediate 5-c> was used, instead of <Intermediate 1-f>, to produce <Chemical Formula 83>. (2.4 g, 28%)

MS (MALDI-TOF): m/z 574.19 [M$^+$]

Synthesis Example 6: Synthesis of Compound of Chemical Formula 104

Synthesis Example 6-(1): Synthesis of Intermediate 6-a

Intermediate 6-a was synthesized as illustrated in the following Reaction Scheme 38:

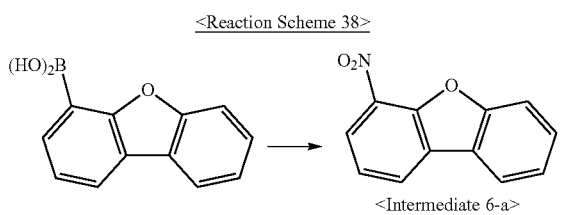 [SMILES: OB(O)c1cccc2c1oc1ccccc12 ; O=[N+]([O-])c1cccc2c1oc1ccccc12]

In a 2-L round-bottom flask reactor, 4-dibenzofuran boronic acid (85.0 g, 0.401 mol), bismuth (III) nitrate pentahydrate (99.2 g, 0.200 mol), and toluene (400 ml) were stirred together at 70° C. for 3 hrs under a nitrogen atmosphere. After completion of the reaction, the reaction mixture was cooled to room temperature, and the precipitates thus formed were filtered and washed with toluene to afford <Intermediate 6-a> (61.5 g, 72%).

Synthesis Example 6-(2): Synthesis of Intermediate 6-b

Intermediate 6-b was synthesized as illustrated in the following Reaction Scheme 39:

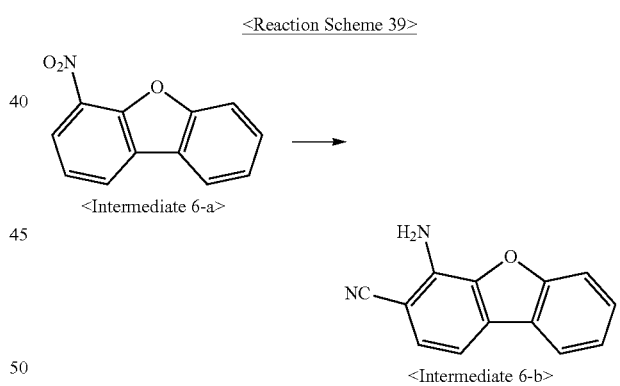

In a 2-L round-bottom flask reactor, ethyl cyanoacetate (202.9 g, 1.794 mol) and dimethylformamide (500 ml) were placed. Potassium hydroxide (67.10 g, 1.196 mol) and potassium cyanide (38.95 g, 0.598 mol) were added thereto, followed by dimethyl formamide (200 ml). The reaction solution was stirred at room temperature. Intermediate 6-a (127.5 g, 0.737 mol) was added little by little to the reaction solution, followed by stirring at 50° C. for 72 hrs. After completion of the reaction, an aqueous sodium hydroxide solution (25%, 200 ml) was added to the reaction solution, which was then stirred for 3 hrs under reflux and cooled to room temperature. Extraction was performed using ethyl acetate and water. The organic layer was isolated and concentrated in a vacuum. Purification through column chromatography afforded Intermediate 6-b (20.0 g, 16%).

Synthesis Example 6-(3): Synthesis of Intermediate 6-c

Intermediate 6-c was synthesized as illustrated in the following Reaction Scheme 40:

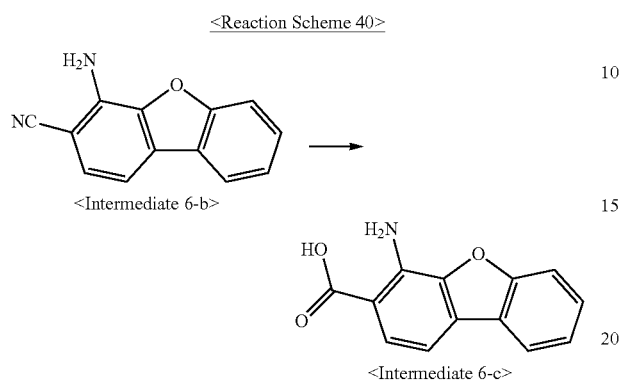

<Reaction Scheme 40>

<Intermediate 6-b>

<Intermediate 6-c>

In a 2-L round-bottom flask reactor, Intermediate 6-b (20.0 g, 0.096 mol), ethanol (600 ml), and an aqueous potassium hydroxide solution (142.26 g, 2.53 mol, 170 ml) were stirred together for 12 hrs under reflux. After completion of the reaction, the reaction mixture was cooled to room temperature and acidified with 6-N HCl (400 ml). The solid thus formed was stirred for 20 min and filtered. The filtrate was washed with ethanol to afford Intermediate 6-c (17.0 g, 88.5%).

Synthesis Example 6-(4): Synthesis of Intermediate 6-d

Intermediate 6-d was synthesized as illustrated in the following Reaction Scheme 41:

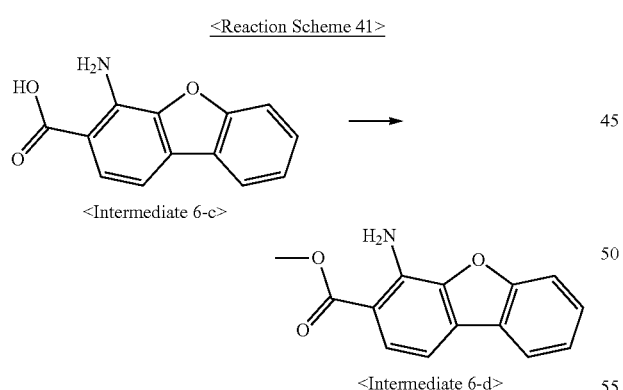

<Reaction Scheme 41>

<Intermediate 6-c>

<Intermediate 6-d>

In a 2-L round-bottom flask reactor, Intermediate 6-c (17.0 g, 0.075 mol) and sulfuric acid (15 ml) were stirred together for 72 hrs under reflux. After completion of the reaction, the reaction mixture was cooled to room temperature and then extracted with ethyl acetate and water. The organic layer was isolated and washed with an aqueous sodium hydrogen carbonate, followed by concentration in a vacuum. The concentrate was crystallized in an excess of methanol and filtered to afford Intermediate 6-d (14.0 g, 77.6%).

Synthesis Example 6-(5): Synthesis of Intermediate 6-e

Intermediate 6-e was synthesized as illustrated in the following Reaction Scheme 42:

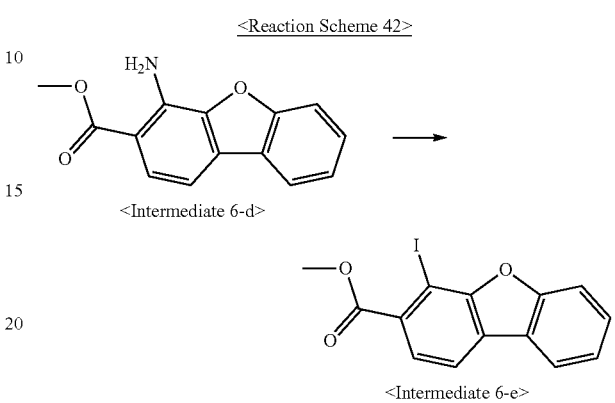

<Reaction Scheme 42>

<Intermediate 6-d>

<Intermediate 6-e>

The same procedure was conducted as in Synthesis Example 5-(1), with the exception of using <Intermediate 6-d> instead of 2-phenoxyaniline, to synthesize Intermediate 6-e (9.1 g, 48%).

Synthesis Example 6-(6): Synthesis of Intermediate 6-f

Intermediate 6-f was synthesized as illustrated in the following Reaction Scheme 43:

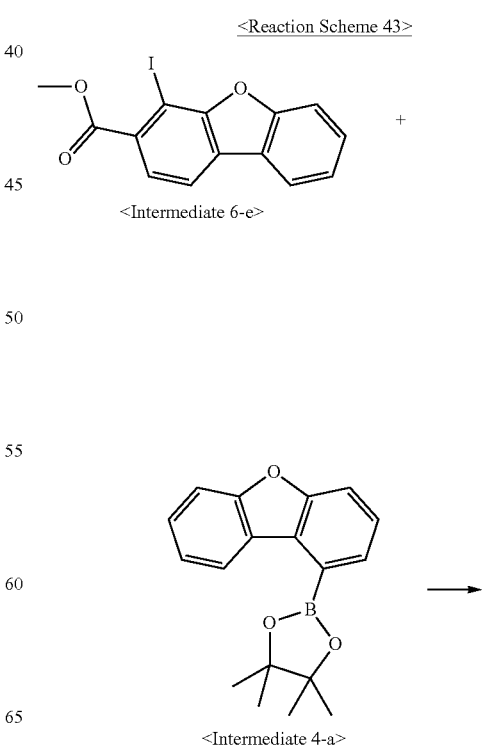

<Reaction Scheme 43>

<Intermediate 6-e>

+

<Intermediate 4-a>

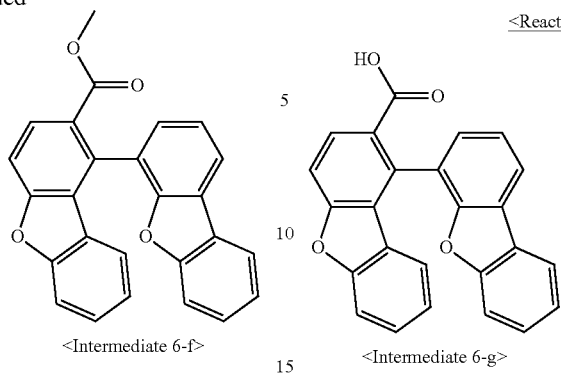

<Intermediate 6-f>

The same procedure was conducted as in Synthesis Example 4-(2), with the exception of using <Intermediate 6-e> instead of methyl 5-bromo-2-iodobenzoate, to synthesize <Intermediate 6-f>. (5.3 g, 52.3%)

Synthesis Example 6-(7): Synthesis of Intermediate 6-g

Intermediate 6-g was synthesized as illustrated in the following Reaction Scheme 44:

<Reaction Scheme 44>

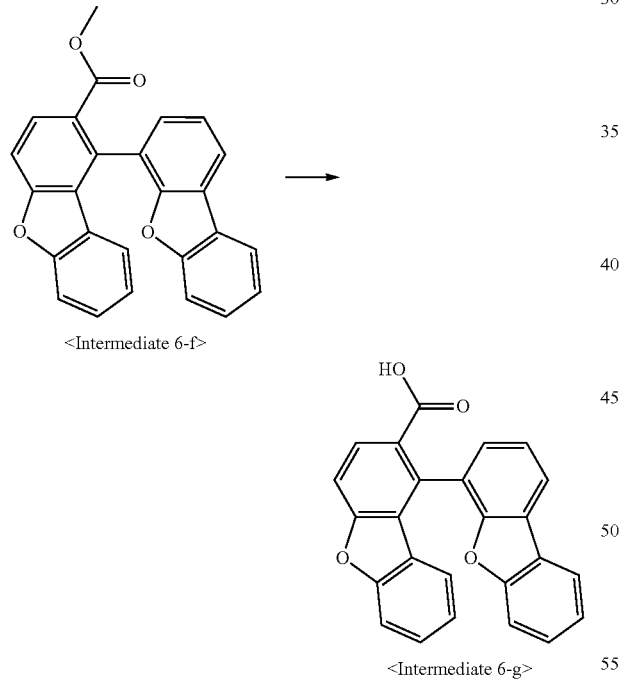

<Intermediate 6-f>

<Intermediate 6-g>

The same procedure was conducted as in Synthesis Example 1-(2), with the exception that <Intermediate 6-f> was used, instead of <Intermediate 1-a>, to produce <Intermediate 6-g>. (4.5 g, 88.1%)

Synthesis Example 6-(8): Synthesis of Intermediate 6-h

Intermediate 6-h was synthesized as illustrated in the following Reaction Scheme 45:

<Reaction Scheme 45>

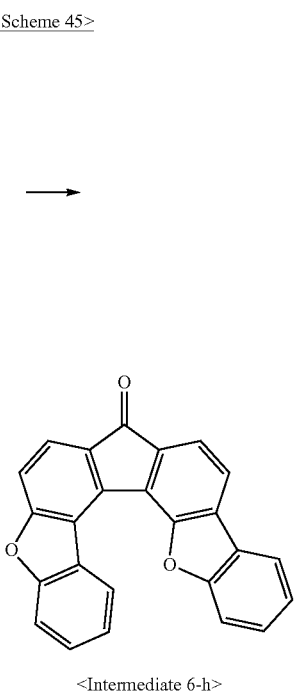

<Intermediate 6-g>

<Intermediate 6-h>

The same procedure was conducted as in Synthesis Example 1-(3), with the exception that <Intermediate 6-g> was used, instead of <Intermediate 1-b>, to produce <Intermediate 6-h>. (3.8 g, 88.8%)

Synthesis Example 6-(9): Synthesis of Intermediate 6-i

Intermediate 6-i was synthesized as illustrated in the following Reaction Scheme 46:

<Reaction Scheme 46>

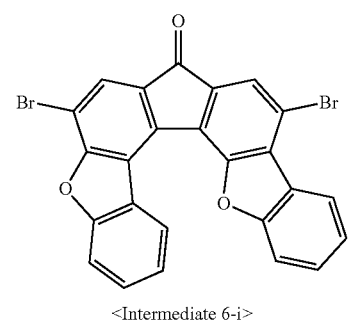

<Intermediate 6-h>

<Intermediate 6-i>

The same procedure was conducted as in Synthesis Example 1-(4), with the exception that <Intermediate 6-h> was used, instead of <Intermediate 1-c>, to produce <Intermediate 6-i> (3 g, 55%)

Synthesis Example 6-(10): Synthesis of Intermediate 6-j

Intermediate 6-j was synthesized as illustrated in the following Reaction Scheme 47:

<Reaction Scheme 47>

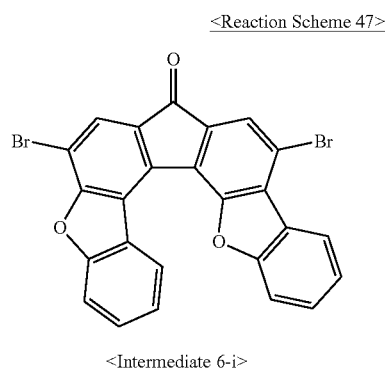

<Intermediate 6-i>

+

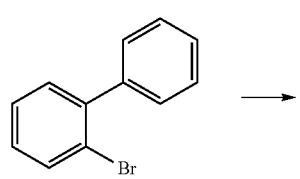

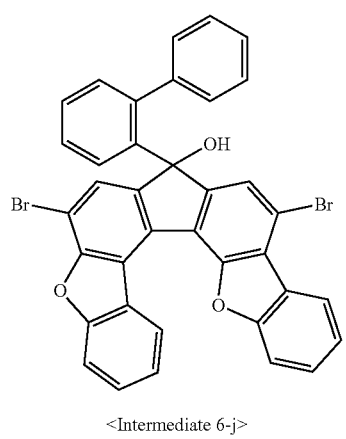

<Intermediate 6-j>

The same procedure was conducted as in Synthesis Example 1-(5), with the exception that <Intermediate 6-i> was used, instead of <Intermediate 1-d>, to produce <Intermediate 6-j>. (2.5 g, 64%)

Synthesis Example 6-(11): Synthesis of Intermediate 6-k

Intermediate 6-k was synthesized as illustrated in the following Reaction Scheme 48:

<Reaction Scheme 48>

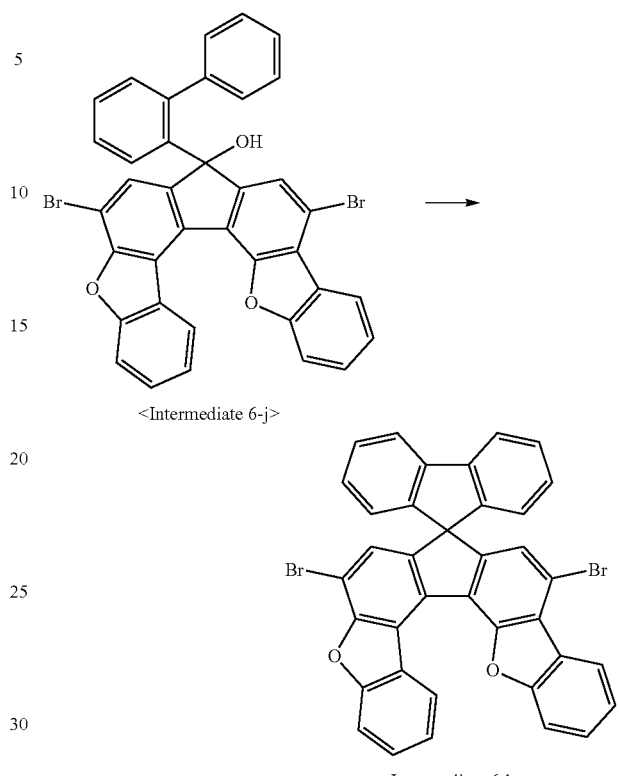

<Intermediate 6-j>

<Intermediate 6-k>

The same procedure was conducted as in Synthesis Example 1-(6), with the exception that <Intermediate 6-j> was used, instead of <Intermediate 1-e>, to produce <Intermediate 6-k>. (2.2 g, 90.4%)

Synthesis Example 6-(12): Synthesis of Compound of Chemical Formula 104

The compound of Chemical Formula 104 was synthesized as illustrated in the following Reaction Scheme 49:

<Reaction Scheme 49>

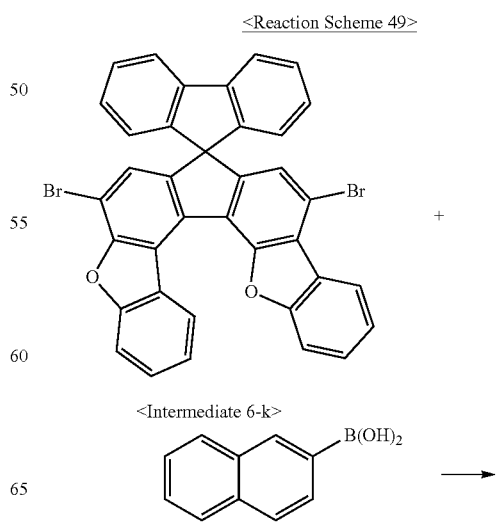

<Intermediate 6-k>

+

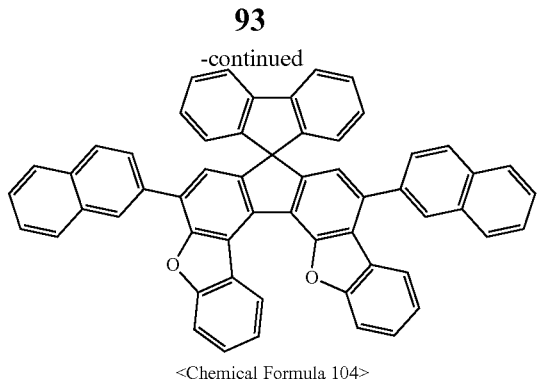

<Chemical Formula 104>

In a 500-ml round bottom flask reactor, <Intermediate 6-k> (10.0 g, 0.015 mol), 2-naphthalene boronic acid (5.16 g, 0.030 mol), tetrakis triphenyl phosphine palladium (0.706 g, 0.001 mol), potassium carbonate (8.45 g, 0.061 mol), toluene (45 ml), dioxane (45 ml), and water (18 ml) were stirred together for 2 hrs under reflux. After completion of the reaction, the reaction mixture was cooled to room temperature and concentrated. The concentrate was dissolved in dichloromethane and recrystallized in methanol, followed by hot filtration with toluene. After isolation and purification by column chromatography, recrystallization in dichloromethane and acetone afforded the compound of Chemical Formula 104. (8.6 g, 77%)

MS (MALDI-TOF): m/z 748.24 [M$^+$]

Synthesis Example 7: Synthesis of Compound of Chemical Formula 115

Synthesis Example 7-(1): Synthesis of Intermediate 7-a

Intermediate 7-a was synthesized as illustrated in the following Reaction Scheme 50:

<Reaction Scheme 50>

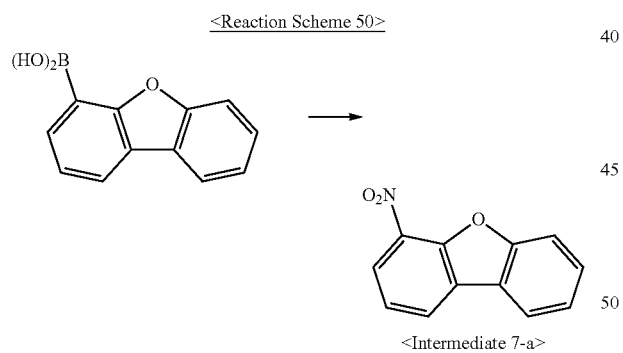

<Intermediate 7-a>

In a 2-L round-bottom flask reactor, 4-dibenzofuranboronic acid (85.0 g, 0.401 mol), bismuth (III) nitrate pentahydrate (99.2 g, 0.200 mol), and toluene (400 ml) were stirred together at 70° C. for 3 hrs under a nitrogen atmosphere. After completion of the reaction, the reaction mixture was cooled to room temperature, and the precipitates thus formed were filtered and washed with toluene to afford Intermediate 7-a (61.5 g, 72%).

Synthesis Example 7-(2): Synthesis of Intermediate 7-b

Intermediate 7-b was synthesized as illustrated in the following Reaction Scheme 51:

<Reaction Scheme 51>

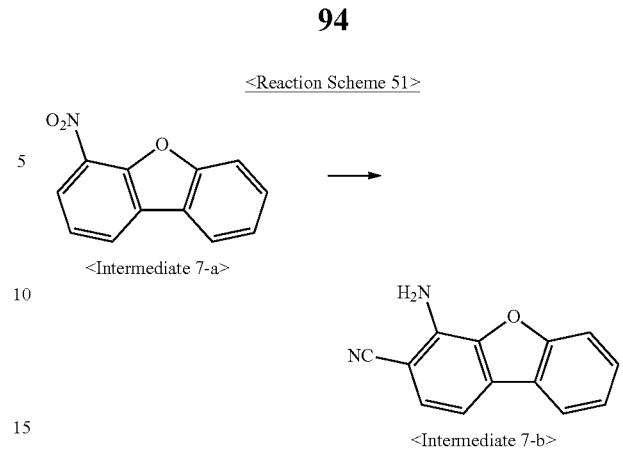

<Intermediate 7-a>

<Intermediate 7-b>

In a 2-L round-bottom flask reactor, ethyl cyanoacetate (202.9 g, 1.794 mol) and dimethylformamide (500 ml) were placed. Potassium hydroxide (67.10 g, 1.196 mol) and potassium cyanide (38.95 g, 0.598 mol) were added thereto, followed by dimethyl formamide (200 ml). The reaction solution was stirred at room temperature. Intermediate 7-a (127.5 g, 0.737 mol) was added little by little to the reaction solution, followed by stirring at 50° C. for 72 hrs. After completion of the reaction, an aqueous sodium hydroxide solution (25%, 200 ml) was added to the reaction solution, which was then stirred for 3 hrs under reflux and cooled to room temperature. Extraction was performed using ethyl acetate and water. The organic layer was isolated and concentrated in a vacuum. Purification through column chromatography afforded Intermediate 7-b (20.0 g, 16%).

Synthesis Example 7-(3): Synthesis of Intermediate 7-c

Intermediate 7-c was synthesized as illustrated in the following Reaction Scheme 52:

<Reaction Scheme 52>

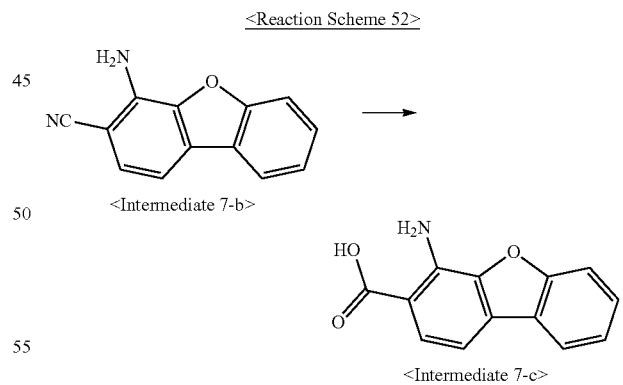

<Intermediate 7-b>

<Intermediate 7-c>

In a 2-L round-bottom flask reactor, Intermediate 7-b (20.0 g, 0.096 mol), ethanol (600 ml), and an aqueous potassium hydroxide solution (142.26 g, 2.53 mol, 170 ml) were stirred together for 12 hrs under reflux. After completion of the reaction, the reaction mixture was cooled to room temperature and acidified with 6-N HCl (400 ml). The solid thus formed was stirred for 20 min and filtered. The filtrate was washed with ethanol to afford Intermediate 7-c (17.0 g, 88.5%).

Synthesis Example 7-(4): Synthesis of Intermediate 7-d

Intermediate 7-d was synthesized as illustrated in the following Reaction Scheme 53:

<Reaction Scheme 53>

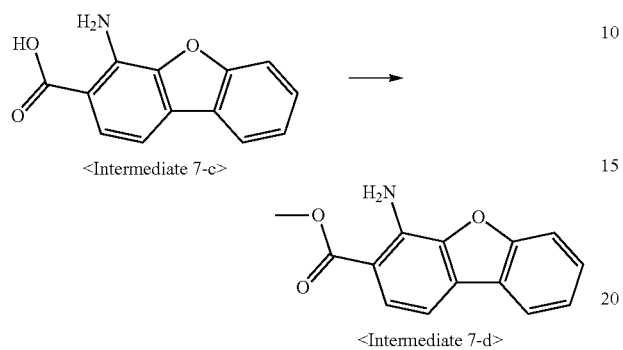

<Intermediate 7-c>

<Intermediate 7-d>

In a 2-L round-bottom flask reactor, Intermediate 7-c (17.0 g, 0.075 mol) and sulfuric acid (15 ml) were stirred together for 72 hrs under reflux. After completion of the reaction, the reaction mixture was cooled to room temperature and then extracted with ethyl acetate and water. The organic layer was isolated and washed with an aqueous sodium hydrogen carbonate, followed by concentration in a vacuum. The concentrate was crystallized in an excess of methanol and filtered to afford Intermediate 7-d (14.0 g, 77.6%).

Synthesis Example 7-(5): Synthesis of Intermediate 7-e

Intermediate 7-e was synthesized as illustrated in the following Reaction Scheme 54:

<Reaction Scheme 54>

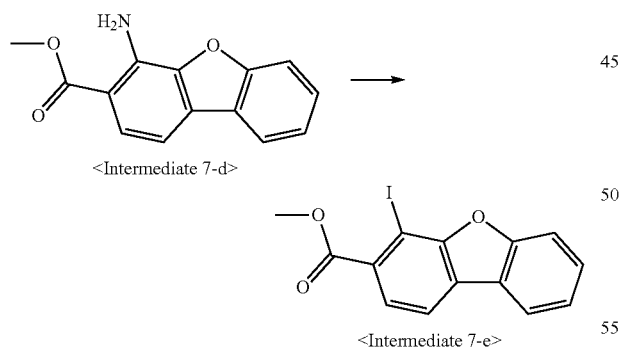

<Intermediate 7-d>

<Intermediate 7-e>

The same procedure was conducted as in Synthesis Example 5-(1), with the exception of using <Intermediate 7-d> instead of 2-phenoxyaniline, to synthesize Intermediate 7-e (9.1 g, 48%).

Synthesis Example 7-(6): Synthesis of Intermediate 7-f

Intermediate 7-f was synthesized as illustrated in the following Reaction Scheme 55:

<Reaction Scheme 55>

<Intermediate 7-e>

+

<Intermediate 4-a>

<Intermediate 7-f>

The same procedure was conducted as in Synthesis Example 1-(1), with the exception that <Intermediate 7-e> and <Intermediate 4-a> were used, instead of methyl 5-bromo-2-iodobenzoate and 4-dibenzofuran boronic acid, respectively, to produce <Intermediate 7-f>. (5.3 g, 52.3%)

Synthesis Example 7-(7): Synthesis of Intermediate 7-g

Intermediate 7-g was synthesized as illustrated in the following Reaction Scheme 56:

<Reaction Scheme 56>

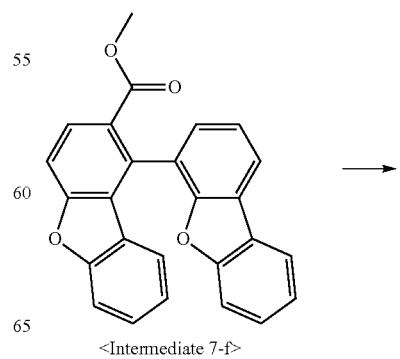

<Intermediate 7-f>

-continued

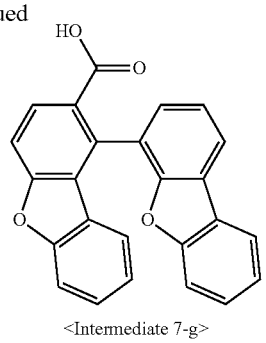

<Intermediate 7-g>

The same procedure was conducted as in Synthesis Example 1-(2), with the exception that <Intermediate 7-f> was used, instead of <Intermediate 1-a>, to produce <Intermediate 7-g>. (4.5 g, 88.1%)

Synthesis Example 7-(8): Synthesis of Intermediate 7-h

Intermediate 7-h was synthesized as illustrated in the following Reaction Scheme 57:

<Reaction Scheme 57>

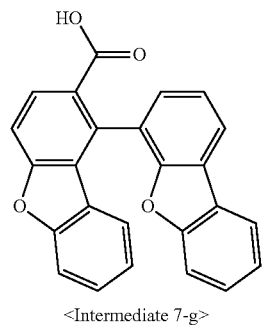 

<Intermediate 7-g>

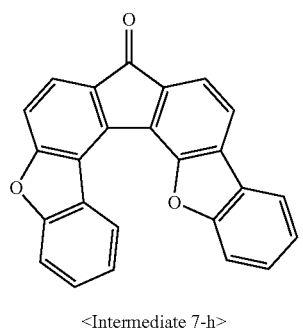

<Intermediate 7-h>

The same procedure was conducted as in Synthesis Example 1-(3), with the exception that <Intermediate 7-g> was used, instead of <Intermediate 1-b>, to produce <Intermediate 7-h>. (3.8 g, 88.8%)

Synthesis Example 7-(9): Synthesis of Intermediate 7-i

Intermediate 7-i was synthesized as illustrated in the following Reaction Scheme 58:

<Reaction Scheme 58>

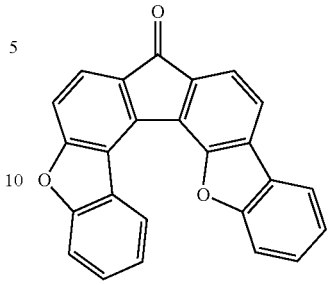

<Intermediate 7-h>

\+

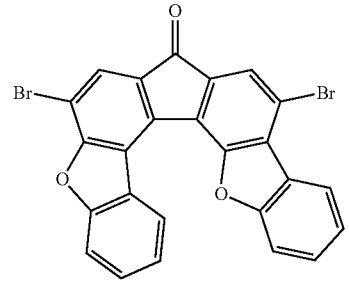

<Intermediate 7-i>

The same procedure was conducted as in Synthesis Example 1-(4), with the exception that <Intermediate 7-h> was used, instead of <Intermediate 1-c>, to produce <Intermediate 7-i>. (3.0 g, 55%)

Synthesis Example 7-(10): Synthesis of Intermediate 7-j

Intermediate 7-j was synthesized as illustrated in the following Reaction Scheme 59:

<Reaction Scheme 59>

\+

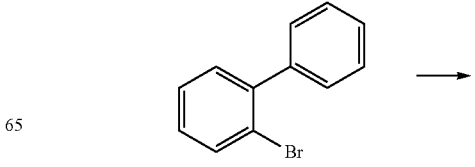

-continued

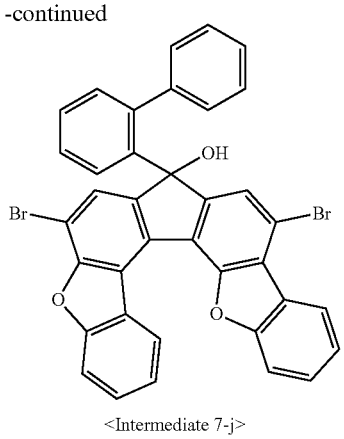

<Intermediate 7-j>

The same procedure was conducted as in Synthesis Example 1-(5), with the exception that <Intermediate 7-i> was used, instead of <Intermediate 1-d>, to produce <Intermediate 7-j> (2.5 g, 64%)

Synthesis Example 7-(11): Synthesis of Intermediate 7-k

Intermediate 7-k was synthesized as illustrated in the following Reaction Scheme 60:

<Reaction Scheme 60>

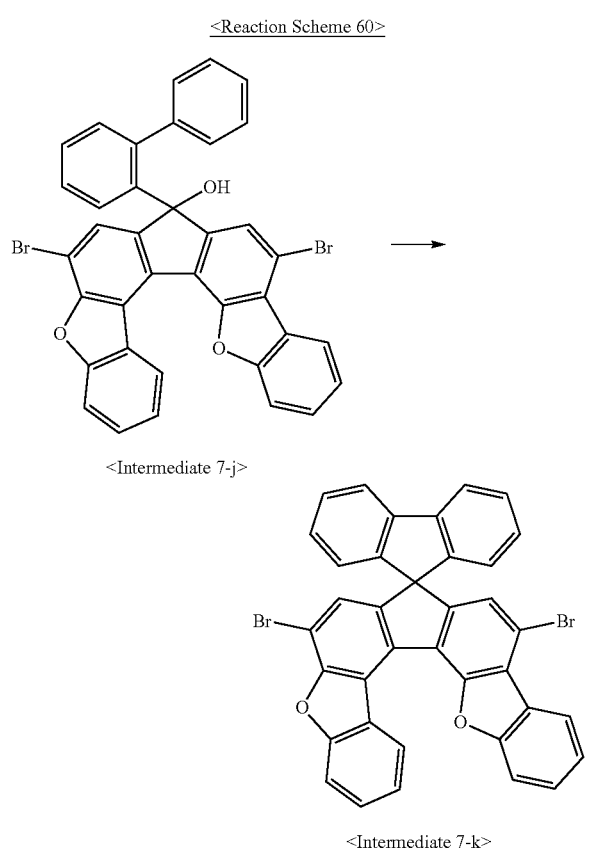

<Intermediate 7-j>

<Intermediate 7-k>

The same procedure was conducted as in Synthesis Example 1-(6), with the exception that <Intermediate 7-j> was used, instead of <Intermediate 1-e>, to produce <Intermediate 7-k>. (2.2 g, 90.4%)

Synthesis Example 7-(12): Synthesis of Compound of Chemical Formula 115

The compound of Chemical Formula 115 was synthesized as illustrated in the following Reaction Scheme 61:

<Reaction Scheme 61>

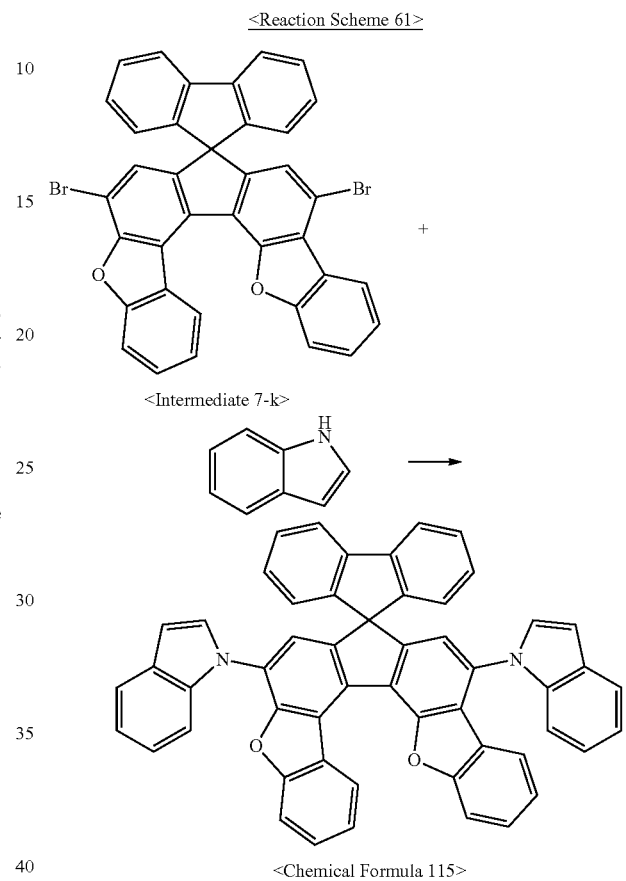

<Intermediate 7-k>

<Chemical Formula 115>

In a 500-ml round-bottom flask reactor, <Intermediate 7-k> (10.0 g, 0.015 mol), indole (3.9 g, 0.033 mol), tri-tert-butylphosphonium tetrafluoroborate (1.4 g, 0.002 mol), phosphonium (0.887 g, 0.003 mol), sodium tert-butoxide (8.45 g, 0.061 mol), and xylene (50 ml) were stirred together for 2 hrs under reflux. After completion of the reaction, the reaction mixture was cooled to room temperature and concentrated. The concentrate was recrystallized in methanol, followed by hot filtration with toluene. After isolation and purification by column chromatography, recrystallization in dichloromethane and acetone afforded the compound of Chemical Formula 115. (8.9 g, 81.5%)

MS (MALDI-TOF): m/z 726.23 [M$^+$]

Example 1 to 7: Fabrication of OLED

An ITO glass substrate was patterned to have a translucent area of 2 mm×2 mm and cleansed. The ITO glass was mounted in a vacuum chamber that was then set to have a base pressure of $1\times10^{-7}$ torr. On the ITO glass substrate, films were formed of DNTPD (700 Å) and α-NPD (300 Å) in that order. A light-emitting layer (250 Å) was formed of a mixture of one of the compounds listed in Table 1 according to the present disclosure and [BD1] at a ratio of 97:3.

Then, [Chemical Formula E-1] and [Chemical Formula E-2] were deposited at a ratio of 1:1 to form an electron transport layer 300 Å thick, on which an electron injection layer of [Chemical Formula E-1] (5 Å thick) was formed and then covered with an Al layer (1000 Å) to fabricate an organic light-emitting diode. The organic light-emitting diodes thus obtained were measured at 0.4 mA for luminescence properties.

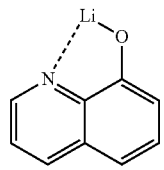

[Chemical FormulaE-1]

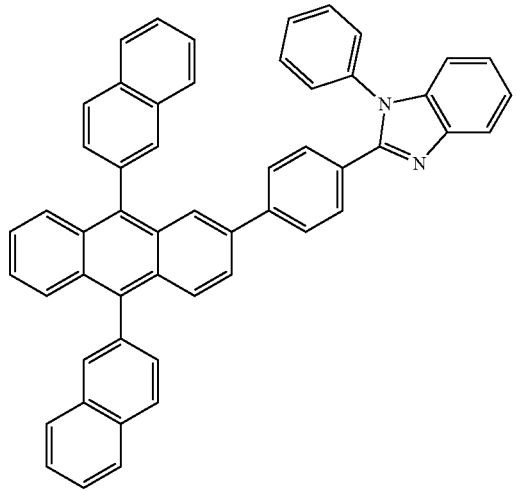

[Chemical FormulaE-2]

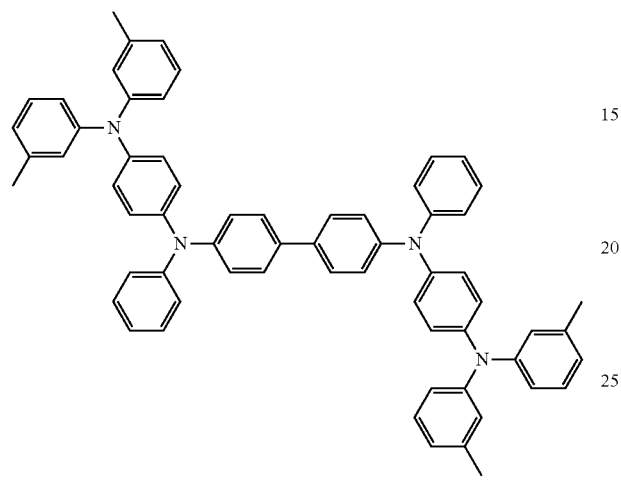

[DNTPD]

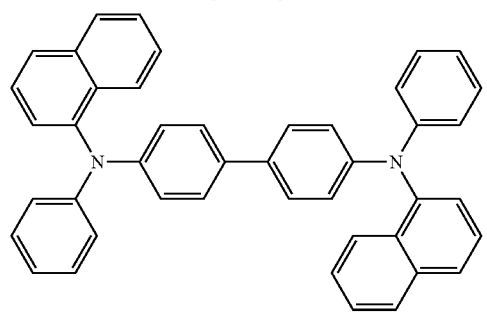

[α-NPD]

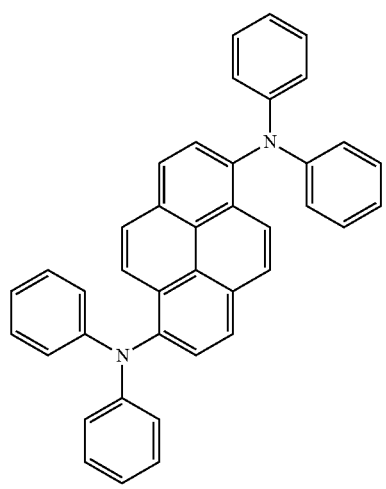

[BD1]

Comparative Example 1

Organic light-emitting diodes were fabricated in the same manner as in Examples 1 to 7, with the exception that [BH1], instead of the compounds used in Examples 1 to 7, was used as a host. The luminescence of the organic light-emitting diodes was measured at 0.4 mA. The structure of [BH1] is as follows.

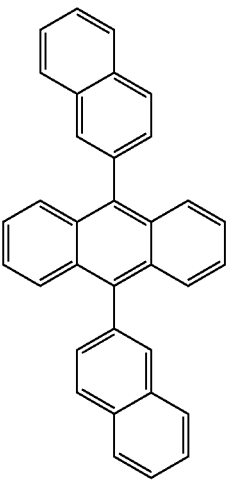

[BH1]

The organic light-emitting diodes fabricated in Examples 1 to 7 and Comparative Example 1 were measured for voltage, current density, Q. E., and color coordinates, and the results are summarized in Table 1, below.

TABLE 1

| | Volt. | Current Density (mA/cm$^2$) | Q.E (%) | CIEx | CIEy |
|---|---|---|---|---|---|
| C. Ex. 1 [BH1] | 4.1 | 10 | 5.2 | 0.143 | 0.150 |
| Ex. 1 [Chemical Formula 1] | 3.5 | 10 | 5.9 | 0.135 | 0.140 |
| Ex. 2 [Chemical Formula 21] | 3.7 | 10 | 7.7 | 0.137 | 0.146 |
| Ex. 3 [Chemical Formula 34] | 3.8 | 10 | 8.6 | 0.135 | 0.146 |
| Ex. 4 [Chemical Formula 52] | 3.3 | 10 | 7.5 | 0.140 | 0.148 |
| Ex. 5 [Chemical Formula 83] | 3.7 | 10 | 7.2 | 0.135 | 0.143 |
| Ex. 6 [Chemical Formula 104] | 3.6 | 10 | 8 | 0.137 | 0.141 |
| Ex. 7 [Chemical Formula 115] | 3.8 | 10 | 6.7 | 0.132 | 0.148 |

As is understood from data of Table 1, the compounds according to the present disclosure exhibited excellent device characteristics including high efficiency (Q. E) and low-voltage operation, compared to those of Comparative Example 1, thus having the high plausibility of applying for organic light-emitting diodes.

INDUSTRIAL APPLICABILITY

Capable of fabricating organic light-emitting diodes that exhibit excellent diode properties including low-voltage operation and high luminous efficiency, the present invention is industrially available.

The invention claimed is:

1. A compound represented by the following Chemical Formula A or Chemical Formula B:

[Chemical Formula A]

[Chemical Formula B]

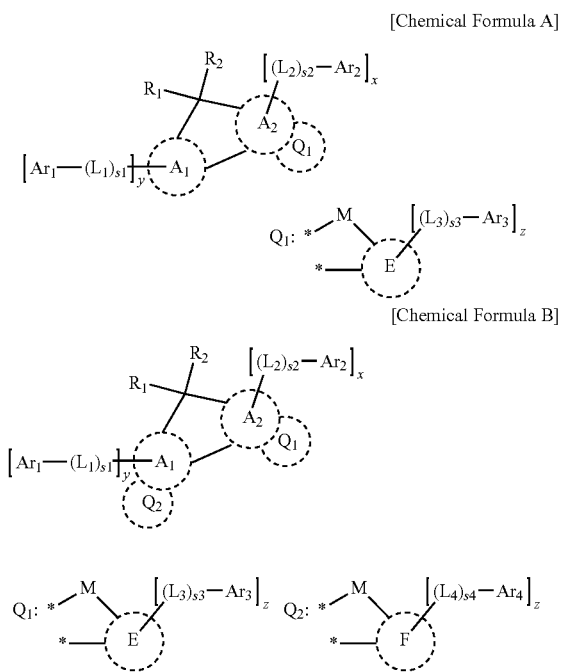

-continued

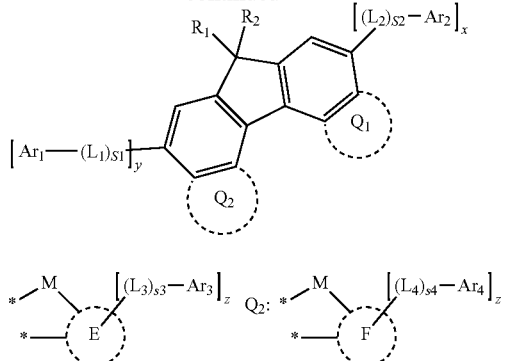

wherein,
$A_1$ is a substituted or unsubstituted aromatic hydrocarbon ring of 6 to 50 carbon atoms,
$A_2$, E, and F may be the same or different, and are each independently a substituted or unsubstituted aromatic hydrocarbon ring of 6 carbon atoms,
wherein two adjacent carbon atoms of the aromatic ring $A_1$ and two adjacent carbon atoms of the aromatic ring $A_2$ form a 5-membered fused ring together with the carbon atom having substituents $R_1$ and $R_2$ linked thereto;
linkers $L_1$ to $L_4$ may be the same or different, and are each independently selected from among a direct bond and a substituted or unsubstituted arylene of 6 to 60 carbon atoms;
M in Chemical Formula A is S;
M in Chemical Formula B is any one selected from among O, and S;
$R_1$ and $R_2$ may be the same or different, and are each independently any one selected from among a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms,
$Ar_1$, $Ar_3$, and $Ar_4$ may be the same or different, and are each independently any one selected from among, a substituted or unsubstituted aryl of 6 to 50 carbon atoms, substituted or unsubstituted heteroaryl of 2 to 50 carbon atoms,
$R_1$ and $R_2$ are bonded to each other to form a mono- or polycyclic aliphatic or aromatic ring in Chemical Formula B;
wherein $Ar_2$ in Chemical Formula A is a substituted or unsubstituted aryl of 6 to 50 carbon atoms, and
$Ar_2$ in Chemical Formula B is selected from among a substituted or unsubstituted aryl of 6 to 50 carbon atoms, or a substituted or unsubstituted heteroaryl of 2 to 50 carbon atoms bearing one to three heteroatom(s) selected from among O and S,
s1 to s4 are each independently an integer of 1,
x is an integer of 1,
y is an integer of 1; and
z is 0; and
two adjacent carbon atoms of the $A_2$ ring moiety of Chemical Formula A may occupy respective positions * of Structural Formula $Q_1$ to form a fused ring, and
two adjacent carbon atoms of the benzene ring moiety of Chemical Formula B may occupy respective positions * of structural Formula $Q_2$ to form a fused ring, and two adjacent carbon atoms of the benzene ring moiety of Chemical Formula B may occupy respective positions * of Structural Formula $Q_1$ to form a fused ring,
wherein the term 'substituted' in the expression 'substituted or unsubstituted' used in Chemical Formulas A and B means having at least one substituent selected from the group consisting of a deuterium atom, a cyano, a halogen, a nitro, an alkyl of 1 to 24 carbon atoms, a halogenated alkyl of 1 to 24 carbon atoms, an aryl of 6 to 24 carbon atoms, and an arylalkyl of 7 to 24 carbon atoms.

2. The compound of claim 1, wherein the substituted or unsubstituted aromatic hydrocarbon rings of 6 to 50 carbon atoms may be the same or different and each be independently selected from among compounds represented by Structural Formulas 10 to 21:

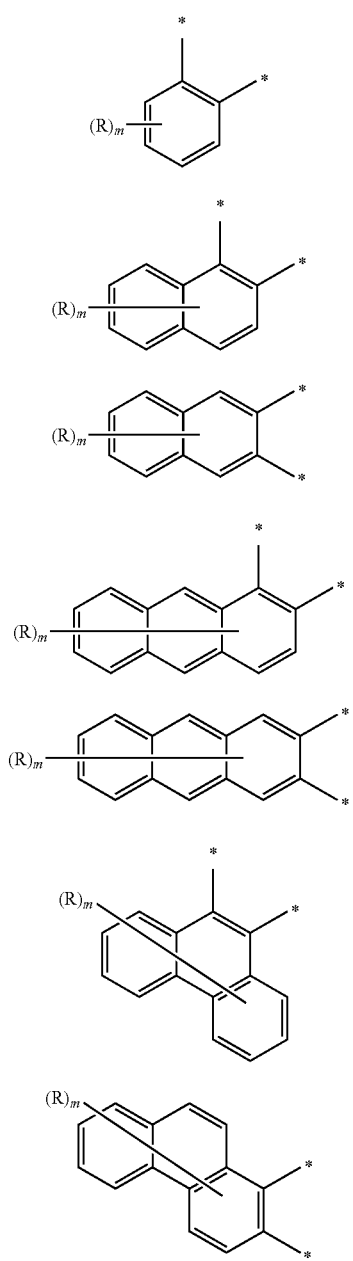

[Structural Formula 10]

[Structural Formula 11]

[Structural Formula 12]

[Structural Formula 13]

[Structural Formula 14]

[Structural Formula 15]

[Structural Formula 16]

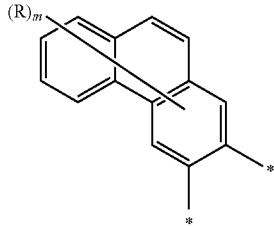

[Structural Formula 17]

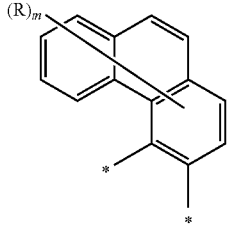

[Structural Formula 18]

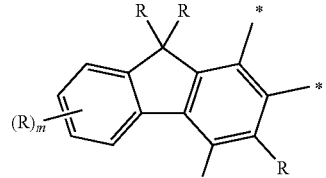

[Structural Formula 19]

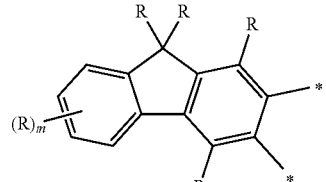

[Structural Formula 20]

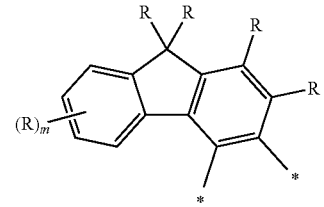

[Structural Formula 21]

wherein

"-*" denotes a bonding site for forming a 5-membered ring bearing the carbon atom connected to the substituents $R_1$ and $R_2$ or a bonding site for forming a 5-membered ring bearing M of Structural Formula $Q_1$ and $Q_2$;

when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring;

R's are the same as defined above for $R_1$ and $R_2$ in claim 1; and m is an integer of 1 to 8, with the proviso that when m is 2 or greater or two or more R's exist, the corresponding R's may be the same or different.

3. The compound of claim 1, wherein the linkers $L_1$ to $L_4$ in Chemical Formula A or B may be a single bond or one selected from among compounds represented by the following Structural Formulas 1, 2, 4, 6, and 7:

[Structural Formula 1]

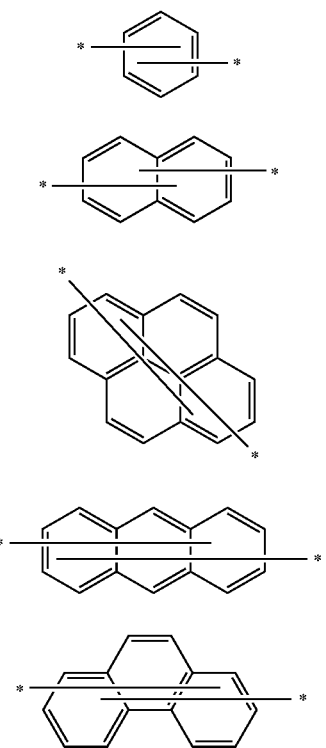

[Structural Formula 2]

[Structural Formula 4]

[Structural Formula 6]

[Sructural Formula 7]

wherein, each of the unsubstituted carbon atoms of the aromatic ring moiety is bound with a hydrogen atom or a deuterium atom.

4. The compound of claim 1, wherein $Ar_1$, $Ar_3$, and $Ar_4$ in Chemical Formulas A and B are each selected from among a substituted or unsubstituted aryl of 6 to 50 carbon atoms, y is 1, and z is 0.

5. The compound of claim 1, wherein $R_1$ and $R_2$ In Chemical Formula A or B may be the same or different and are each independently a substituted or unsubstituted aryl of 6 to 24 carbon atoms.

6. The compound of claim 1, wherein the compound is one selected from the group consisting of compounds represented by the following Chemical Formulas 28, 30, 32, 78-79, 91, 92, 96, 104, 112, 113, 116, 128, and 134:

<Chemical Formula 28>

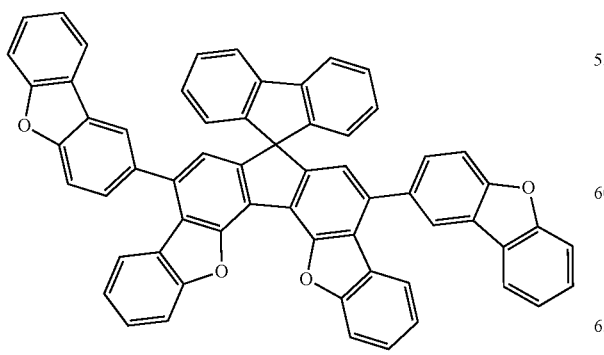

<Chemical Formula 30>

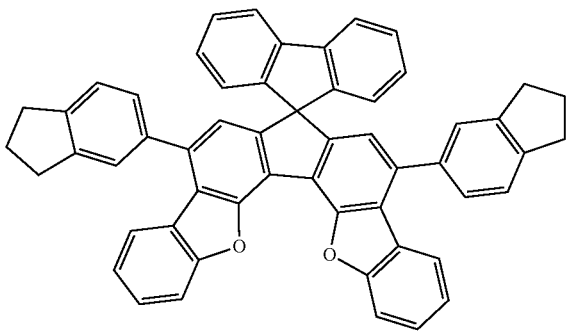

<Chemical Formula 32>

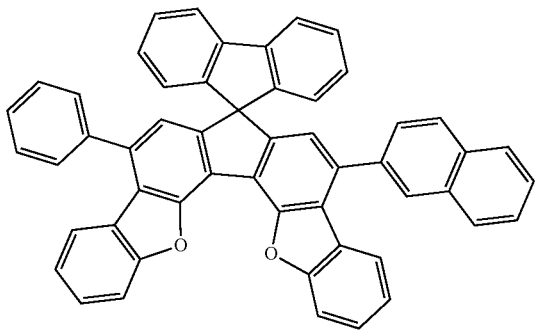

<Chemical Formula 78>

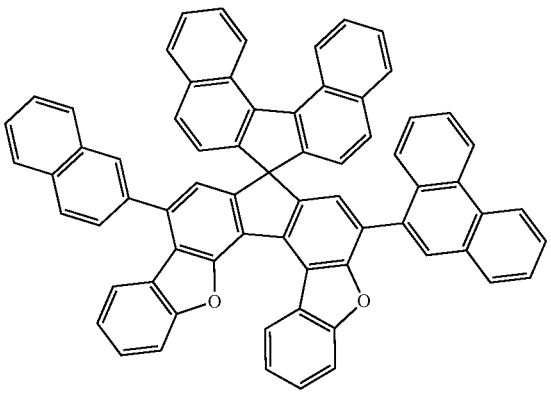

<Chemical Formula 79>

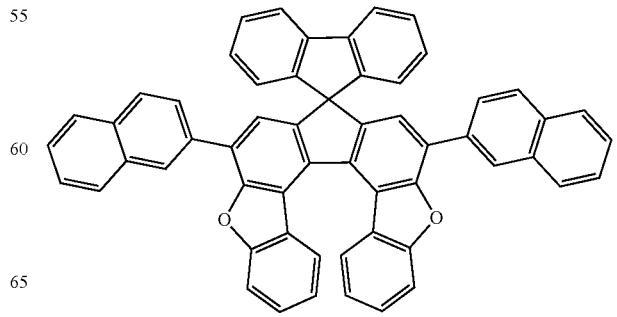

<Chemical Formula 91>
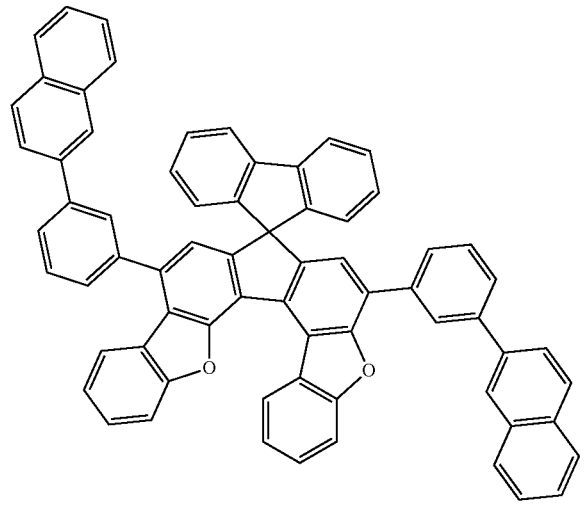
<Chemical Formula 92>
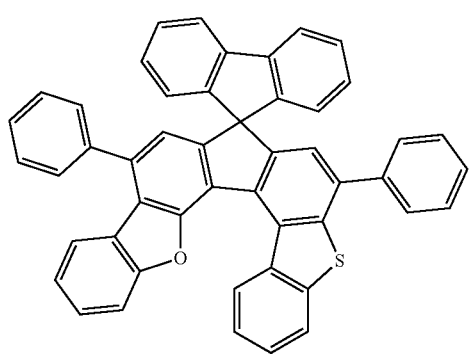
<Chemical Formula 96>
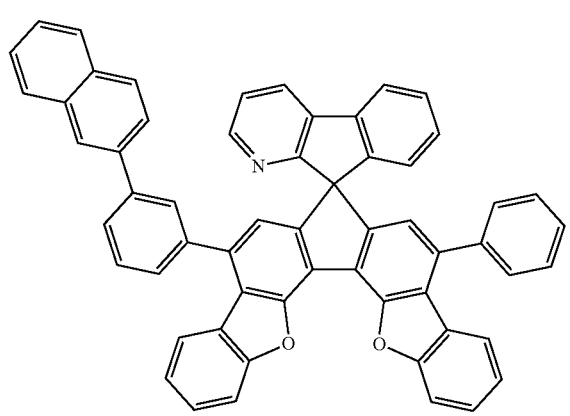
<Chemical Formula 104>
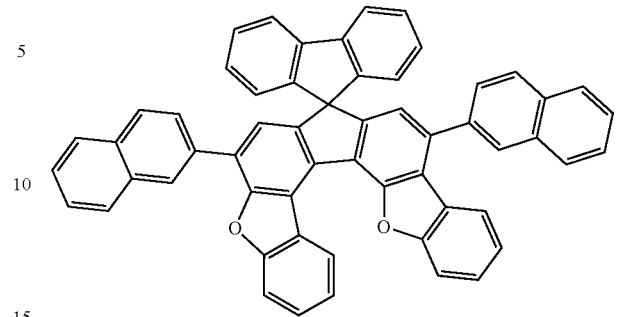
<Chemical Formula 112>
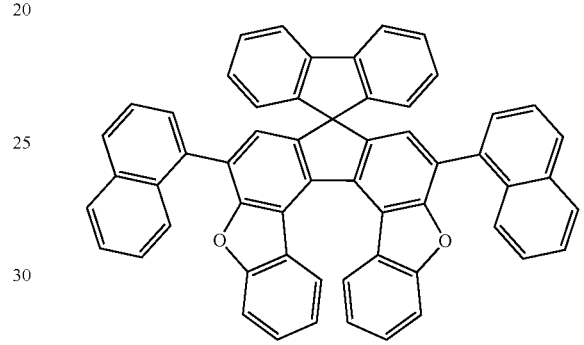
<Chemical Formula 113>
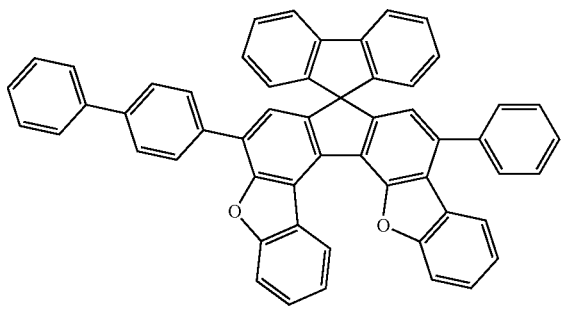
<Chemical Formula 116>
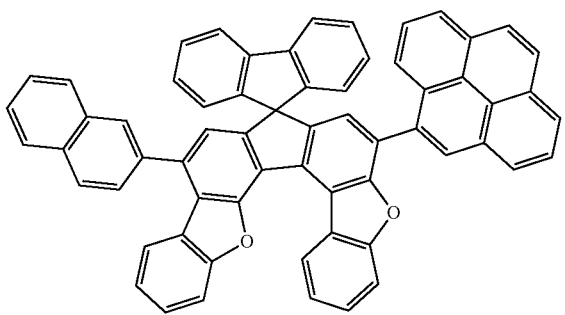

<Chemical Formula 128>

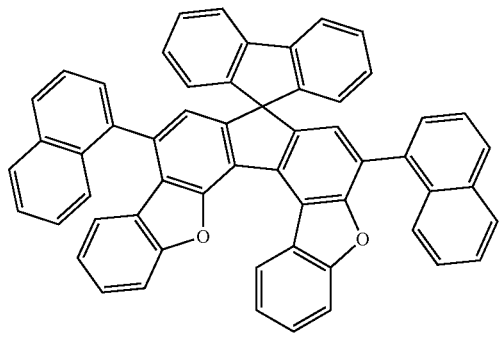

<Chemical Formula 134>

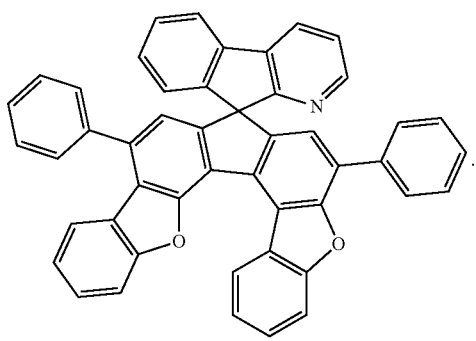

7. An organic light-emitting diode, comprising:
   a first electrode:
   a second electrode; and
   an organic layer interposed between the first and the second electrode,
   wherein the organic layer contains the compound of claim 1.

8. The organic light-emitting diode of claim 7, wherein the organic layer comprises at least one of a hole injecting layer, a hole transport layer, a functional layer capable of both hole injection and hole transport, a light-emitting layer, an electron transport layer, and an electron injecting layer.

9. The organic light-emitting diode of claim 8, wherein the organic layer interposed between the first electrode and the second electrode is a light-emitting layer composed of a host and a dopant, the organic light-emitting compound serving as a host.

10. The organic light-emitting diode of claim 8, wherein at least one selected from among the layers is deposited using a deposition process or a solution process.

11. The organic light-emitting diode of claim 7, wherein the organic light-emitting diode is used for a device selected from among a flat display device, a flexible display device, a monochrome or grayscale flat illumination device, and a monochrome or grayscale flexible illumination device.

* * * * *